(12) United States Patent
Endo et al.

(10) Patent No.: US 10,173,990 B2
(45) Date of Patent: Jan. 8, 2019

(54) URAT1 INHIBITOR

(71) Applicants: Nippon Chemiphar Co., Ltd., Tokyo (JP); J-Pharma Co., Ltd., Kanagawa (JP); DeThree Res. Lab. Inc., Ibaraki (JP)

(72) Inventors: Tsuyoshi Endo, Misato (JP); Kunio Kobayashi, Misato (JP); Hiroto Tanaka, Misato (JP); Daisuke Saito, Misato (JP); Masuharu Hirano, Misato (JP); Hitoshi Endou, Kanagawa (JP); Naohiko Anzai, Tokyo (JP)

(73) Assignees: Nippon Chemiphar Co., Ltd., Tokyo (JP); J-Pharma Co., Ltd., Kanagawa (JP); DeThree Res. Lab. Inc., Ibaraki (JP)

( * ) Notice: Subject to any disclaimer, the term of this patent is extended or adjusted under 35 U.S.C. 154(b) by 0 days.

(21) Appl. No.: 15/507,888

(22) PCT Filed: Dec. 28, 2015

(86) PCT No.: PCT/JP2015/086482
§ 371 (c)(1),
(2) Date: Mar. 1, 2017

(87) PCT Pub. No.: WO2016/108282
PCT Pub. Date: Jul. 7, 2016

(65) Prior Publication Data
US 2017/0290795 A1   Oct. 12, 2017

(30) Foreign Application Priority Data

Dec. 29, 2014 (JP) .................. 2014-267009
Jun. 26, 2015 (JP) .................. 2015-128396

(51) Int. Cl.
C07D 275/04 (2006.01)
C07D 411/04 (2006.01)
(Continued)

(52) U.S. Cl.
CPC .......... *C07D 275/04* (2013.01); *A61K 31/277* (2013.01); *A61K 31/33* (2013.01);
(Continued)

(58) Field of Classification Search
CPC ... C07D 275/04; C07D 411/04; C07D 277/62
See application file for complete search history.

(56) References Cited

U.S. PATENT DOCUMENTS 3,652,646 A * 3/1972 Leigh et al. .......... C07C 51/367
250/396 R
5,614,532 A * 3/1997 Carling ................ A61K 31/47
514/312
2005/0080105 A1   4/2005 Boy et al.

FOREIGN PATENT DOCUMENTS

CN  103819419 A   5/2014
EP  1698348 A1   9/2006
(Continued)

OTHER PUBLICATIONS

National Center for Biotechnology Information. PubChem Compound Database; CID=410066, https://pubchem.ncbi.nlm.nih.gov/compound/410066 (accessed Oct. 1, 2017, created Mar. 26, 2005).*
(Continued)

*Primary Examiner* — Matthew P Coughlin
(74) *Attorney, Agent, or Firm* — Wood Herron & Evans LLP

(57) ABSTRACT

Provided are a compound represented by the following Formula (III), a tautomer or stereoisomer of the compound, or a pharmaceutically acceptable salt or solvate thereof used as a therapeutic agent for gout or hyperuricemia. (In the Formula (III), $R^{1a}$, $R^{2a}$, $R^{6a}$, and $R^{7a}$ represent a hydrogen atom, an alkyl group having 1 to 8 carbon atoms, an alkoxy group having 1 to 8 carbon atoms, or a cyano group, $R^{3a}$ and $R^{8a}$ form a benzene ring or a 5-membered heteroaryl ring containing 1 to 3 heteroatoms, as a ring constituent element, selected from nitrogen atoms, oxygen atoms, and sulfur atoms together with two carbon atoms to which $R^{3a}$ and $R^{8a}$ are bonded, $R^{4a}$ and $R^{5a}$ form a benzene ring together with two carbon atoms to which $R^{4a}$ and $R^{5a}$ are bonded or represent any of the groups represented by $R^{1a}$ described above, $W^a$ represents $CR^{10a}$ or N, and where, $R^{10a}$ represents any of the groups represented by $R^{1a}$, $X^a$ represents an oxygen atom or a sulfur atom, $Y^a$ represents an alkylene chain having 1 to 8 carbon atoms, and where, the alkylene chain may be substituted with an alkyl group having 1 to 8 carbon atoms and the alkylene chain may be a linear or branched alkylene chain, the branched alkylene chain may have a 3- to 7-membered ring formed by side chains bonded to carbon atoms which are the same as or different from each other, together with the carbon atoms to which the side chains are bonded and may have a double bond in the middle thereof, and $Z^a$ represents $CO_2H$).

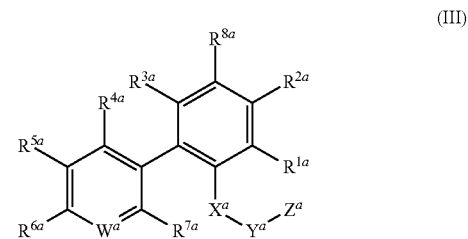

(III)

56 Claims, No Drawings

(51) Int. Cl.
| | |
|---|---|
| C07C 255/54 | (2006.01) |
| C07D 215/20 | (2006.01) |
| C07D 215/36 | (2006.01) |
| C07C 321/24 | (2006.01) |
| C07D 417/12 | (2006.01) |
| C07D 471/04 | (2006.01) |
| C07D 263/54 | (2006.01) |
| C07D 209/08 | (2006.01) |
| C07D 277/62 | (2006.01) |
| C07D 285/14 | (2006.01) |
| C07D 213/30 | (2006.01) |
| A61K 31/277 | (2006.01) |
| A61K 31/404 | (2006.01) |
| A61K 31/423 | (2006.01) |
| A61K 31/428 | (2006.01) |
| A61K 31/433 | (2006.01) |
| A61K 31/437 | (2006.01) |
| A61K 31/4406 | (2006.01) |
| A61K 31/47 | (2006.01) |
| A61K 31/33 | (2006.01) |

(52) U.S. Cl.
CPC .......... *A61K 31/404* (2013.01); *A61K 31/423* (2013.01); *A61K 31/428* (2013.01); *A61K 31/433* (2013.01); *A61K 31/437* (2013.01); *A61K 31/4406* (2013.01); *A61K 31/47* (2013.01); *C07C 255/54* (2013.01); *C07C 321/24* (2013.01); *C07D 209/08* (2013.01); *C07D 213/30* (2013.01); *C07D 215/20* (2013.01); *C07D 215/36* (2013.01); *C07D 263/54* (2013.01); *C07D 277/62* (2013.01); *C07D 285/14* (2013.01); *C07D 411/04* (2013.01); *C07D 417/12* (2013.01); *C07D 471/04* (2013.01)

(56) References Cited

FOREIGN PATENT DOCUMENTS

| | | |
|---|---|---|
| JP | 2008531473 A | 8/2008 |
| JP | 5314123 B2 | 10/2013 |
| WO | 2009070740 A2 | 6/2009 |
| WO | 2010135530 A2 | 11/2010 |
| WO | 2011159839 A2 | 12/2011 |
| WO | 2011159840 A2 | 12/2011 |

OTHER PUBLICATIONS

National Center for Biotechnology Information. PubChem Compound Database; CID=11717064, https://pubchem.ncbi.nlm.nih.gov/compound/11717064 (accessed Oct. 1, 2017, created Oct. 26, 2006).*
CAS Registry Entry for Registry No. 161531-92-6, which entered STN on Mar. 16, 1995.*
CAS Registry Entry No. 1629448-67-4, which entered STN on Oct. 21, 2014.*
National Center for Biotechnology Information. PubChem Compound Database; CID=68780855, https://pubchem.ncbi.nlm.nih.gov/compound/68780855 (accessed Oct. 2, 2017, created Nov. 30, 2012).*
National Center for Biotechnology Information. PubChem Compound Database; CID=68777470, https://pubchem.ncbi.nlm.nih.gov/compound/68777470 (accessed Feb. 26, 2018, created Nov. 30, 2012) (Year: 2012).*
Sheridan, R. J. Chem. Inf. Comput. Sci. 2002, 42, 103-108 (Year: 2002).*
Tue Heesgaard Jepsen et al., Synthesis of Functionalized Dibenzothiophenes—An Efficient Three-Step Approach Based on Pd-Catalyzed C—C and C—S Bond Formations, European Journal of Organic Chemistry, 2011, vol. 1, pp. 53-57.
M.F. El-Newaihy et al., Condensation of Aryl Benzyl Ketones with Dimethyl Diglycollate, Journal Fuer Praktissche Chemie (Leipzing), 1980, vol. 322, pp. 42-48.
John B. Bremner et al., Synthesis and antibacterial studies of binaphthyl-based tripeptoids. Part 2, Bioorganic & Medicinal Chemistry, 2010, vol. 18, No. 13, pp. 4793-4800.
PCT Office, International Search Report issued in corresponding PCT Application No. PCT/JP2015/086482 dated Apr. 5, 2016, 6 pages.
Guideline for the Management of Hyperuricemia and Gout, Second Edition, edited by The Guideline Revising Committee of Japanese Society of Gout and Nucleic Acid Metabolism published by Medical Review Co., Ltd. (2010).
Has Hyperuricemia Been Increasing? Focusing on Gender in Gout and Nucleic Acid Metabolism vol. 30; pp. 1-4, 2006, written by Masako Tomita and Shouichi Mizuno.
Fini MA, Elias A, Johnson RJ, Wright RM; Contribution of Uric Acid to Cancer Risk, Recurrence, and Mortality. Clin Transl Med., 2012, 1, 1-15.
Hyperuricemia and Gout written by Masafumi Kurajoh, 2014, 22, 29-33.
Lipkowitz MS; Regulation of Uric Acid Excretion by the Kidney. Curr. Rheumatol. Rep., 2012, 14, 179-188.
Enomoto A et al., Molecular Identification of a Renal Urate-Anion Exchanger that Regulates Blood Urate Levels. Nature. 2002, 417, 447-452.
Hyperuricemia and Gout written by Ichiro Hisatome, 2014, 22, 16-22.
So A, Thorens B; Uric Acide Transport and Disease. J. Clin. Invest., 2010, 120, 1791-1799.
Qinying Deng et al., American Laboratory (Shelton, Connecticut) 1999, 31, 43 and 44, 46 and 47.
European Patent Office, Search Report issued in European Patent Application No. 15875408.5 dated Apr. 16, 2018, 11 pages.
Li Xiaohong et al., "Synthesis, Characterization of Chiral Eu(III) Complexes and Study of Chiral Fluorescence Probe to ct-DNA", Chinese journal of rare metals, vol. 37, No. 1, pp. 97-103, 2013.
Xie Zhengfeng et al., "Synthesis and Crystal Structure of the Bis-Schiff Base Compounds", Chinese journal of organic chemistry, vol. 31, No. 4, pp. 548-552, 2011.
John B. Bremner, et al., "Binaphthyl-Based Dicationic Peptoids with Therapeutic Potential", Angew. Chem. Int. Ed. 2010, 49, 537-540.
Toshiyuki Itoh, et al., "Linker-Oriented Design of Binaphthol Derivatives for Optical Resolution Using Lipase-Catalyzed Reaction", J. Org. Chem., 2008, 73, 3875-3884.
Atsushi Yoshizawa, et al., "Host-guest effect on chirality transfer from a binaphthyl derivative to a host nematic liquid crystal", Chem. Commun, 2007, 257-259.
Zhu Quanhong et al., "Chiral Separation of Binaphthalene Enantiomers by Thin-layer Chromatography", Chinese journal of analytical chemistry, vol. 27, No. 11, 1320-1323, 1999.
Zhong Shizhou et al., "NMR Study of 2,2'-Disubstituted-1,1'-binaphthyl Compounds", Journal of Instrumental Analysis, vol. 17, No. 1, 9-13, 1998.
"2D Structure", FEJAIZRKRIVRRC-UHFFFAOYSA-N, Pubchem, p. 1.
Chinese Patent Office, Office Action issued in Chinese Patent Application No. 201580071302.0 dated Aug. 3, 2018, 31 pages.

* cited by examiner

URAT1 INHIBITOR

TECHNICAL FIELD

The present invention relates to a compound that inhibits re-absorption of uric acid and promotes excretion of the uric acid through a uric acid transporter URAT1.

BACKGROUND ART

Hyperuricemia is the cause of urate deposition diseases including gouty arthritis and renal disorder (NPL 1). The prevalence of hyperuricemia in Japan has been reported as 21.5% in adult males. The prevalence in adult males by age is highest in the 30s and 40s, and approximately reaches 30% (NPL 2). Meanwhile, it has been known that the serum uric acid level increases post menopause, and the prevalence of hyperuricemia in females is reported as 1.3% and 3.7% in those under and over 50 years old, respectively. The results suggest that the incidence of this disease is high in men. The number of gout patients tends to be increasing year by year (NPL 3) and the number of patients with asymptomatic hyperuricemia, as the potential patients, has been estimated as 8,000,000 in Japan.

In the past, hyperuricemia has been attracting attention as the cause of urate deposition diseases such as gout arthritis, gouty tophus, and urinary calculus as described above. However, in recent years, the clinical report that overturns this concept, in other words, a possibility of suggesting that uric acid itself regardless of deposition is deeply involved in onset and progression of chronic kidney disease, cardiovascular disease, and metabolic syndrome as a causative factor has been reported (NPL 4). Further, allopurinol serving as a therapeutic agent of hyperuricemia not only decrease the uric acid level, it has also shown the possibility that allopurinol suppresses cardiovascular disorders such as hypertension, ischemic disease, and heart failure (NPL 5).

Control of the serum uric acid level is involved in re-absorption and secretion of uric acid in the proximal tubule of the kidney (NPL 6). In the re-absorption of uric acid, Urate Transporter 1 (URAT1) existing in the proximal tubule plays an important role (NPL 7). URAT1 is an organic anion transporter-like molecule identified from both of gene database analysis and expression function analysis using oocytes (NPL 7). URAT1 was identified on the brush border membrane side of the proximal tubular epithelial cells as 12-transmembrane protein and shown to transport uric acid by exchanging with a chloride ion or organic anions. Since lactic acid and pyrazine carboxylic acid serving as an uricosuric agent promote activity of URAT1, the re-absorption of uric acid in the kidney is promoted (NPL 9). On the other hand, URAT1 is inhibited by benzbromarone, probenecid, and losartan. In some patients with renal hypouricemia, it has been reported that the function of re-absorbing uric acid in the kidney is significantly degraded due to mutations of URAT1 and the serum uric acid level is low (NPL 9). Therefore, since the inhibition of URAT1 decreases the serum uric acid level, probenecid or benzbromarone has been used as a therapeutic agent of hyperuricemia.

Hyperuricemia has been largely classified into three types, such as a uric acid overproduction type, a uric acid underexcretion type, and a combined type. Among them, the number of patients is the highest in underexcretion type and an uricosuric agent such as probenecid or benzbromarone is selected as a therapeutic agent for these patients (NPL 1). Further, hyperuricemia with complications of lifestyle related diseases is mainly uric acid underexcretion type and re-absorption of uric acid in the proximal tubule of the kidney is believed to be a factor of the onset of hyperuricemia (NPL 8). Therefore, it makes sense to treat hyperuricemia patients having complications of lifestyle related diseases using a drug which inhibits re-absorption of uric acid in the kidney and promotes excretion of uric acid. However, probenecid is a drug which is highly interactive with drugs so that probenecid is required to be cautious when used in combination and it is known that the effects of probenecid is significantly decreased when it is used for hyperuricemia patients having complications of renal disorder (NPL 1). Meanwhile, benzbromarone is considered to be effective for hyperuricemia patients with somewhat reduced kidney functions, but it is reported that benzbromarone causes severe side effects such as fulminant hepatitis (NPL 1). For this reason, in overseas there are some countries that prohibit the use of benzbromarone. Accordingly, a highly safe URAT1 inhibitor is expected to be widely used, as the best-in-class, for the most common hyperuricemia patients having uric acid underexcretion type.

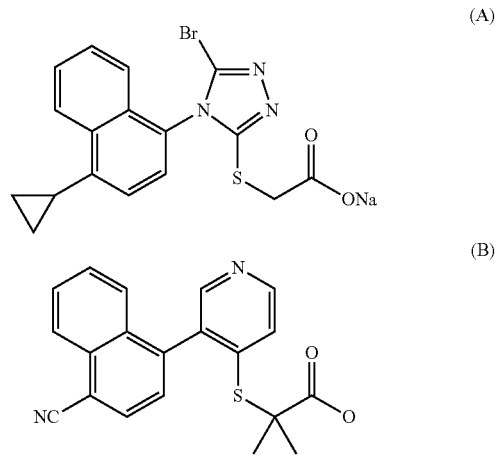

Further, recently, PTLs 1 and 2 describe that a naphthyl-substituted triazole thioacetate derivative or pyridyl thioacetate derivative represented by Formula (A) or (B) exhibits excellent hURAT1 inhibitory actions in uric acid uptake assays using a hURAT1 transporter and thus is useful as a therapeutic agent for hyperuricemia.

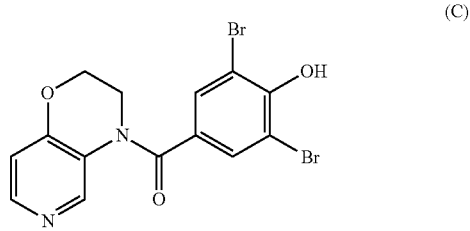 [SMILES: O=C(c1cc(Br)c(O)c(Br)c1)N1CCOc2ccncc21]

Further, PTL 3 describes that a benzbromarone derivative represented by Formula (C) exhibits hURAT1 inhibitory activity, is not interactive between drugs with respect to cytochrome P450 (CYP450), exhibits selectivity between organic anion transporters, and thus has higher solubility and metabolic stability.

The compound represented by the following Formula (I) and the compound represented by Formula (A) or (B) are different from each other in terms that a ring to which thioalkanoic acid is bonded is a bicyclic compound in the former one and a ring to which thioalkanoic acid is bonded is monocyclic in the latter one.

Further, the compound represented by the following Formula (I) and the benzbromarone derivative represented by Formula (C) are clearly different from each other in terms of a structure.

On the other hand, PTL 4 and NPLs 10 and 11 describe compounds represented by the following Formulae (D), (E), and (F) as examples of compounds in which a quinoline ring or a naphthalene ring is substituted with a phenyl group, thioalkanoic acid, or oxyalkanoic acid.

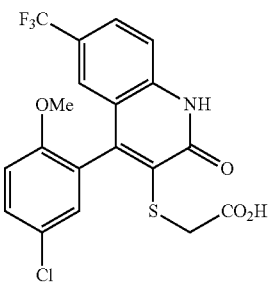
(D)

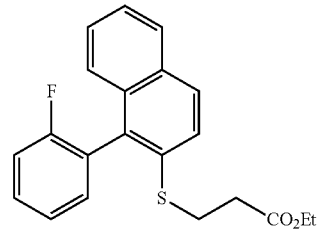
(E)

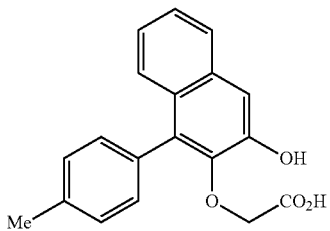
(F)

On the other hand, NPLs 12 and 13 describe compounds represented by the following Formulae (G) and (H) as examples of compounds which have a 1,1'-binaphthalene structure and in which a 2-position of naphthalene has oxyacetic acid and the other 2'-position is substituted with a hydroxy group or a methoxy group.

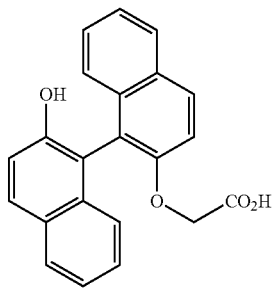
(G)

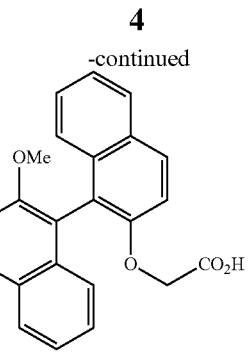
(H)

However, in NPLs 12 and 13, there is no description that any of the compounds represented by Formulae (D) to (H) has a hURAT1 inhibitory action.

CITATION LIST

Patent Literature

[PTL 1] WO2009/070740
[PTL 2] WO2011/159839
[PTL 3] Japanese Patent No. 5314123
[PTL 4] US2005/0080105

Non-Patent Literature

[NPL 1] Guideline for the management of hyperuricemia and gout, $2^{nd}$ edition, edited by The Guideline Revising Committee of Japanese Society of Gout and Nucleic Acid Metabolism published by Medical Review Co., Ltd. (2010)
[NPL 2] Has Hyperuricemia Been Increasing? Focusing on Gender in Gout and Nucleic Acid Metabolism Vol. 30; pp. 1 to 4, 2006, written by Masako Tomita and Shouichi Mizuno
[NPL 3] Future Estimated Population of Japan (estimated in December 2006) investigated by Ministry of Health, Labor and Welfare and National Institute of Population and Social Security Research (total number of health care injuries)
[NPL 4] Fini M A1, Elias A, Johnson R J, Wright R M; Contribution of uric acid to cancer risk, recurrence, and mortality. Clin Transl Med., 2012, 1, 1 to 15.
[NPL 5] Hyperuricemia and Gout written by Masafumi Kurajoh, 2014, 22, 29 to 33.
[NPL 6] Lipkowitz M S.; Regulation of Uric Acid Excretion by the Kidney. Curr. Rheumatol. Rep., 2012, 14, 179 to 188.
[NPL 7] Enomoto A, Kimura H, Chairoungdua A, Shigeta Y, Jutabha P, Cha S H, Hosoyamada M, Takeda M, Sekine T, Igarashi T, Matsuo H, Kikuchi Y, Oda T, Ichida K, Hosoya T, Shiomokata K, Niwa T, Kanai Y, Endou H.; Molecular identification of a renal urate anion exchanger that regulates blood urate levels. Nature. 2002, 417, 447 to 452.
[NPL 8] Hyperuricemia and Gout written by Ichiro Hisatome, 2014, 22, 16 to 22.
[NPL 9] So A, Thorens B.; Uric acid transport and disease. J. Clin. Invest., 2010, 120, 1791 to 1799.
[NPL 10] European Journal of Organic Chemistry 2011, 1, 53 to 57, S53/1 to S53/65.
[NPL 11] Journal fuer Praktische Chemie (Leipzig) 1980, 322, 42 to 48.
[NPL 12] Americal Laboratory (Shelton, Conn.) 1999, 31, 43 and 44, 46 and 47.

[NPL 13] Bioorganic & Medicinal Chemistry 2010, 18, 4793 to 4800.

SUMMARY OF INVENTION

Technical Problem

An object of the present invention is to provide an agent for treating or preventing gout or hyperuricemia which has an excellent uric acid excretion promoting action, does not cause severe side effects such as liver failure and cardiac toxicity, and has high safety.

Further, another object of the present invention is to provide an agent for treating or preventing gout or hyperuricemia which has an excellent uric acid excretion promoting action and has further excellent solubility and metabolic stability.

Solution to Problem

In other words, the present invention relates to a compound represented by the following Formula (I), a tautomer or stereoisomer of the compound, or a pharmaceutically acceptable salt or solvate thereof.

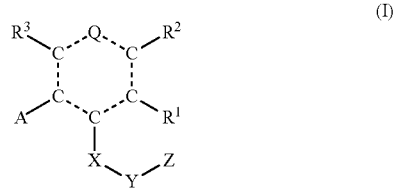

(In the formula, a dotted line represents a single bond or a double bond,

Q represents $CR^8$, $NR^9$, or N, in a case where Q represents $CR^8$, $R^3$ and $R^8$ are bonded to each other to form a naphthalene ring or a quinoline ring together with a ring formed of dotted lines, or a combination of $R^1$ and $R^2$, $R^2$ and $R^8$, or $R^3$ and $R^8$ are bonded to each other to form a 5-membered heteroaryl ring containing 1 to 3 heteroatoms, as a ring constituent element, selected from a nitrogen atom, an oxygen atom, and a sulfur atom together with two carbon atoms to which the combination is bonded, and the heteroaryl ring forms a fused ring together with the ring formed of dotted lines, where, the ring formed of dotted lines is a ring in which the number of double bonds in the ring is the maximum, in a case where Q represents N, $R^1$ and $R^2$ are bonded to each other to form a quinoline ring together with the ring formed of dotted lines, in a case where Q represents $NR^9$, $R^3$ and $R^9$ or $R^2$ and $R^9$ are bonded to each other to form an imidazo[1,2-a]pyridine ring together with the ring formed of dotted lines, in a case where $R^1$, $R^2$, $R^3$, and $R^8$ do not constitute a ring, $R^1$, $R^2$, $R^3$, and $R^8$ may be the same as or different from each other and represent a hydrogen atom, a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, an alkenyl group having 2 to 8 carbon atoms, an alkynyl group having 2 to 8 carbon atoms, an alkylamino group having 1 to 8 carbon atoms, a dialkylamino group having 2 to 12 carbon atoms, an alkyloxycarbonyl group in which the number of carbon atoms of the alkyl group is in a range of 1 to 8, a hydroxy group, an amino group, a carboxyl group, a nitro group, a cyano group, CONR'R", SR', or $SO_2NR'R"$, where, R' and R" may be the same as or different from each other and represent a hydrogen atom or an alkyl group having 1 to 8 carbon atoms, in a case where $R^1$, $R^2$, $R^3$, and $R^8$ constitute a ring, the ring may have 1 to 4 substituents which are the same as the substituent for $R^1$ in the case where $R^1$, $R^2$, $R^3$, and $R^8$ do not constitute a ring, the substituents being the same or different from each other, A represents a phenyl group, a naphthyl group, a pyridyl group, a pyrimidyl group, a pyrazyl group, a pyridazyl group, a quinolyl group, or an isoquinolyl group which may have 1 to 5 substituents same as that of $R^1$ in the case where $R^1$ does not form a ring, the substituents may be the same as or different from each other, where, A is bonded to the ring formed of dotted lines through a carbon atom constituting the ring of the A group, X represents $NR^{11}$, an oxygen atom, or a sulfur atom, where, $R^{11}$ represents a hydrogen atom, an alkyl group having 1 to 8 carbon atoms, or an alkyl group having 1 to 8 carbon atoms substituted with 1 to 3 halogen atoms, Y represents an alkylene chain having 1 to 8 carbon atoms, where, the alkylene chain may be substituted with 1 to 4 same or different groups selected from an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a 3- to 7-membered cycloalkyl group, or a 4- to 7-membered saturated hetero ring having one or two heteroatoms, as a ring constituent element, selected from an oxygen atom, a sulfur atom, and a nitrogen atom, the alkylene chain may be a linear or branched alkylene chain, the branched alkylene chain may have a 3- to 7-membered ring formed by side chains bonded to same carbon atom or different carbon atoms, together with the or each carbon atom to which the side chains are bonded, and the alkylene chain may have a double bond in the chain thereof in a case where the alkylene chain is an alkylene chain having 2 to 8 carbon atoms, Z represents $CO_2H$, $CON(R^{12})(R^{13})$, $CO_2(R^{14})$, $SO_2N(R^{15})(R^{16})$, or a tetrazolyl group, where, $R^{12}$, $R^{14}$, and $R^{15}$ represent a hydrogen atom, an alkyl group having 1 to 8 carbon atoms, an alkyl group having 1 to 8 carbon atoms substituted with 1 to 3 halogen atoms, $R^{13}$ and $R^{16}$ represent a hydrogen atom, an alkyl group having 1 to 8 carbon atoms, an alkyl group having 1 to 8 carbon atoms substituted with 1 to 3 halogen atoms, a phenyl group which may have a substituent, a pyridyl group which may have a substituent, a pyridazyl group, a pyrimidyl group, or a pyrazyl group, or a 5-membered heteroaryl ring contains 1 to 3 heteroatoms, as a ring constituent element, selected from a nitrogen atom which may have a substituent, an oxygen atom, and a sulfur atom, and where, in a case where $R^3$ and $R^8$ are bonded to each other to form a naphthalene ring together with the ring formed of dotted lines, X represents an oxygen atom, A represents naphthalene, and the 1-position of A is bonded to the ring formed of dotted lines, the 2-position of A does not represent any of an alkoxy group having 1 to 8 carbon atoms, a hydroxy group, and ethyl 3-[[1-(2-fluorophenyl)naphthalen-2-yl]thio]propanoate.)

Further, the present invention relates to a compound represented by the following Formula (III), a tautomer or stereoisomer of the compound, or a pharmaceutically acceptable salt or solvate thereof.

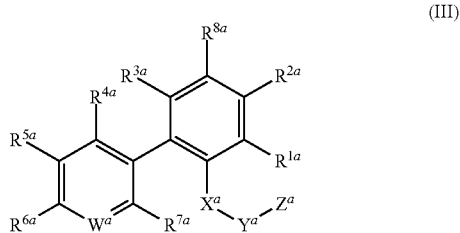

(III)

(In the formula, $R^{1a}$, $R^{2a}$, $R^{6a}$, and $R^{7a}$ may be the same as or different from each other and represent a hydrogen atom, a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group, $R^{3a}$ and $R^{8a}$ form a benzene ring or a 5-membered heteroaryl ring containing 1 to 3 heteroatoms, as a ring constituent element, selected from a nitrogen atom, an oxygen atom, and a sulfur atom together with two carbon atoms to which $R^{3a}$ and $R^{8a}$ are bonded, where, the benzene ring and the heteroaryl ring may have 1 to 4 same or different substituents selected from a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, and a cyano group, $R^{4a}$ and $R^{5a}$ form a benzene ring together with two carbon atoms to which $R^{4a}$ and $R^{5a}$ are bonded or represent any of the groups represented by $R^{1a}$ described above, where, the benzene ring may have 1 to 4 same or different substituents selected from a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, and a cyano group, $W^a$ represents $CR^{10a}$ or N, where, $R^{10a}$ represents any of the groups represented by $R^{1a}$, $X^a$ represents $NR^{11a}$, an oxygen atom or a sulfur atom, where, $R^{11a}$ represents a hydrogen atom, an alkyl group having 1 to 8 carbon atoms, or an alkyl group having 1 to 8 carbon atoms substituted with 1 to 3 halogen atoms, $Y^a$ represents an alkylene chain having 1 to 8 carbon atoms, where, the alkylene chain may be substituted with 1 to 4 groups selected from an alkyl group having 1 to 8 carbon atoms, an alkoxy group having 1 to 8 carbon atoms, an alkyl group having 1 to 8 carbon atoms substituted with 1 to 3 halogen atoms, or an alkoxy group having 1 to 8 carbon atoms substituted with 1 to 3 halogen atoms, the alkylene chain may be a linear or branched alkylene chain, and the branched alkylene chain may have a 3- to 7-membered ring formed by side chains bonded to same carbon atom or different carbon atoms, together with the or each carbon atom to which the side chains are bonded and may have a double bond in the chain thereof in a case where the alkylene chain is an alkylene chain having 2 to 8 carbon atoms, $Z^a$ represents $CO_2H$, a tetrazolyl group, or $SO_2NR^{15a}R^{16a}$, where, $R^{15a}$ and $R^{16a}$ may be the same as or different from each other and represent a hydrogen atom, an alkyl group having 1 to 8 carbon atoms, or an alkyl group having 1 to 8 carbon atoms substituted with 1 to 3 halogen atoms, and in a case where $R^{3a}$ and $R^{8a}$ form a benzene ring together with two carbon atoms to which $R^{3a}$ and $R^{8a}$ are bonded, $X^a$ represents an oxygen atom, and $R^{4a}$ and $R^{5a}$ form a benzene ring together with two carbon atoms to which $R^{4a}$ and $R^{5a}$ are bonded, $R^{7a}$ does not represent an alkoxy group having 1 to 8 carbon atoms or a hydroxy group.)

Further, the present invention relates to a compound represented by the following Formula (IV), a tautomer or stereoisomer of the compound, or a pharmaceutically acceptable salt or solvate thereof.

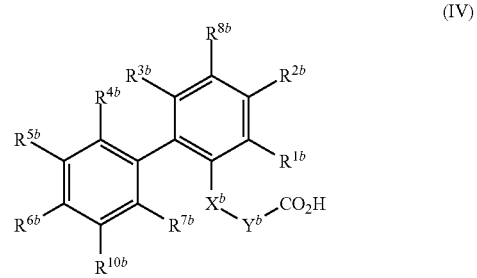

(IV)

(In the formula, $R^{1b}$, $R^{2b}$, $R^{4b}$, $R^{5b}$, $R^{6b}$, $R^{7b}$, and $R^{10b}$ may be the same as or different from each other and represent a hydrogen atom, a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group, $R^{3b}$ and $R^{8b}$ represent a 5-membered heteroaryl ring containing, as ring constituent elements, two heteroatoms which are one nitrogen atom and one oxygen atom or one nitrogen atom and one sulfur atom, together with two carbon atoms to which $R^{3b}$ and $R^{8b}$ are bonded, where, the heteroaryl ring may have a substituent selected from a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, and a cyano group, $X^b$ represents an oxygen atom or a sulfur atom, $Y^b$ represents an alkylene chain having 1 to 8 carbon atoms, and where, the alkylene chain may be substituted with 1 to 4 groups selected from an alkyl groups having 1 to 8 carbon atoms, an alkoxy group having 1 to 8 carbon atoms, an alkyl group having 1 to 8 carbon atoms substituted with 1 to 3 halogen atoms, or an alkoxy group having 1 to 8 carbon atoms substituted with 1 to 3 halogen atoms, the alkylene chain may be a linear or branched alkylene chain, and the branched alkylene chain may have a 3- to 7-membered ring formed by side chains bonded to same carbon atom or different carbon atoms, together with the or each carbon atom to which the side chains are bonded and may have a double bond in the chain thereof in a case where the alkylene chain is an alkylene chain having 2 to 8 carbon atoms.)

Further, the present invention relates to a pharmaceutical composition which contains the compound represented by Formula (I), (III), or (IV), a tautomer or stereoisomer of the compound, or a pharmaceutically acceptable salt or solvate thereof as active components.

Further, the present invention relates to a URAT1 inhibitor which contains the compound represented by Formula (I), (III), or (IV), a tautomer or stereoisomer of the compound, or a pharmaceutically acceptable salt or solvate thereof as active components.

Further, the present invention relates to a therapeutic agent for gout or hyperuricemia which contains the compound represented by Formula (I), (III), or (IV), a tautomer or stereoisomer of the compound, or a pharmaceutically acceptable salt or solvate thereof as active components.

Further, the present invention relates to use of the compound represented by Formula (I), (III), or (IV), a tautomer or stereoisomer of the compound, or a pharmaceutically acceptable salt or solvate thereof for treating gout or hyperuricemia.

Further, the present invention relates to a method of treating gout or hyperuricemia in humans including: a process of administering an effective amount of the compound represented by Formula (I), (III), or (IV), a tautomer or stereoisomer of the compound, or a pharmaceutically acceptable salt or solvate thereof to humans.

Further, the present invention relates to a method of screening a substance having a URAT1 inhibitory action including: culturing URAT1 stably expressed HEK293 cells or HEK293 cells transfected with empty vector, at 37±1° C., adding an uptake solution pH7.4±0.1 at 37±1° C., the uptake solution containing [$^{14}$C] uric acid with or without a test compound, further incubating the cells at 37±1° C. for 2 to 10 minutes, stopping the reaction, washing the cells, lysing the cells, and measuring the radioactivity.

DESCRIPTION OF EMBODIMENTS

Next, the present invention will be described in detail.

In the present specification, examples of the alkyl group having 1 to 8 carbon atoms include a methyl group, an ethyl group, a propyl group, an isopropyl group, a butyl group, an i-butyl group, a t-butyl group, a pentyl group, and a hexyl group.

Examples of the $C_1$-$C_3$ alkyl include a methyl group and an ethyl group.

Examples of the 3- to 7-membered ring cycloalkyl group include a cyclopentyl ring and a cyclohexyl ring.

Examples of the alkenyl group having 2 to 8 carbon atoms include an allyl group.

Examples of the alkynyl group having 2 to 8 carbon atoms include a propargyl group.

Examples of the alkoxy group having 1 to 8 carbon atoms include a methoxy group, an ethoxy group, a propoxy group, an isopropoxy group, a butoxy group, an i-butoxy group, a t-butoxy group, a pentyloxy group, and a hexyloxy group.

Examples of the alkyl group having 1 to 8 carbon atoms substituted with 1 to 3 halogen atoms include a methyl group, an ethyl group, a propyl group, an isopropyl group, a butyl group, and a t-butyl group substituted with 1 to 3 halogen atoms such as fluorine atoms, chlorine atoms, or bromine atoms and preferred examples thereof include a trifluoromethyl group, a chloromethyl group, a 2-chloroethyl group, a 2-bromoethyl group, and a 2-fluoroethyl group.

Examples of the alkoxy group having 1 to 8 carbon atoms substituted with 1 to 3 halogen atoms include a methoxy group, an ethoxy group, a propoxy group, an isopropoxy group, a butoxy group, and a t-butoxy group substituted with 1 to 3 halogen atoms such as fluorine atoms, chlorine atoms, or bromine atoms and preferred examples thereof include a trifluoromethoxy group, a chloromethoxy group, a 2-chloroethoxy group, a 2-bromoethoxy group, and a 2-fluoroethoxy group.

Examples of the halogen atom include a fluorine atom, a chlorine atom, and a bromine atom.

Examples of the alkylamino group having 1 to 8 carbon atoms include a methylamino group and an ethylamino group.

Examples of the dialkylamino group having 2 to 12 carbon atoms include a dimethylamino group and a diethylamino group.

Examples of the alkyloxycarbonyl group in which the number of carbon atoms of the alkyl group is in a range of 1 to 8 include a methoxycarbonyl group and an ethoxycarbonyl group.

In Formula (I), when Q represents $CR^8$, $R^1$ and $R^2$, $R^2$ and $R^8$, or $R^3$ and $R^8$ are bonded to each other to form a 5-membered heteroaryl ring containing 1 to 3 heteroatoms, as a ring constituent element, selected from nitrogen atoms, oxygen atoms, and sulfur atoms together with two carbon atoms to which the combination is bonded, examples of the 5-membered heteroaryl ring include thiazole, isothiazole, oxazole, isoxazole, and 2,1,3-thiadiazole.

In Formula (I), examples of the 4- to 7-membered saturated hetero ring having one or two heteroatoms selected from oxygen atoms, sulfur atoms, and nitrogen atoms as a ring constituent element which is a substituent that may be included in the alkylene chain having 1 to 8 carbon atoms as Y include a pyrrolidine ring, a piperidine ring, a tetrahydrofuran ring, and a morpholine ring.

In Z of Formula (I), in a case where $R^{13}$ and $R^{16}$ represent a phenyl group which may have a substituent, a pyridyl group which may have a substituent, a pyridazyl group, a pyrimidyl group, or a pyrazyl group, or a 5-membered heteroaryl ring which may have a substituent and contains 1 to 3 heteroatoms, as a ring constituent element, selected from nitrogen atoms which may have a substituent, oxygen atoms, and sulfur atoms, examples of the substituent include 1 to 4 halogen atoms which may be the same as or different from each other, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, and a cyano group.

In Z of Formula (I), in a case where $R^{13}$ or $R^{16}$ represents a 5-membered heteroaryl ring which contains 1 to 3 heteroatoms, as a ring constituent element, selected from nitrogen atoms which may have a substituent, oxygen atoms, and sulfur atoms, examples of the heteroaryl ring include thiazole and isothiazole.

In Formula (III), examples of the heteroaryl ring in a case where $R^{3a}$ and $R^{8a}$ form a 5-membered heteroaryl ring containing 1 to 3 heteroatoms, as a ring constituent element, selected from nitrogen atoms, oxygen atoms, and sulfur atoms together with two carbon atoms to which $R^{3a}$ and $R^{8a}$ are bonded include thiazole, isothiazole, oxazole, isoxazole, and 2,1,3-thiadiazole.

In Formula (IV), examples of the 5-membered heteroaryl ring in a case where $R^{3b}$ and $R^{8b}$ represent a 5-membered heteroaryl ring containing, as a ring constituent element, two heteroatoms which are one nitrogen atom and one oxygen atom or sulfur atom together with two carbon atoms to which $R^{3b}$ and $R^{8b}$ are bonded include thiazole, isothiazole, oxazole, and isoxazole.

Examples of the 3- to 7-membered ring in which the alkylene chain as Y, $Y^a$, and $Y^b$ in Formulae (I), (III), and (IV) is a branched alkylene chain and which may be formed by side chains bonded to carbon atoms which are the same as or different from each other, together with the carbon atoms to which the side chains are bonded include cyclopropane, cyclobutane, and cyclopentane.

As the compound of the present invention represented by Formula (I), compounds shown below are preferable.

(1)

The compound represented by Formula (I), a tautomer or stereoisomer of the compound, or a pharmaceutically acceptable salt or solvate thereof, in which A represents a phenyl group, a naphthyl group, or a pyridyl group which may have a substituent selected from a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a nitro group, and a cyano group.

(2)

The compound represented by Formula (I), a tautomer or stereoisomer of the compound, or a pharmaceutically acceptable salt or solvate thereof, in which A is represented by the following Formula (II).

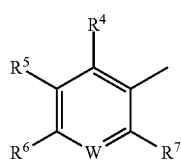

(II)

(Where, $R^4$ and $R^5$ may form a benzene ring together with two carbon atoms to which $R^4$ and $R^5$ are bonded or may be the same as or different from each other and represent a hydrogen atom, a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, a carboxyl group, a mercapto group, an alkylsulfanyl group having 1 to 8 carbon atoms, a nitro group, or a cyano group, where, the benzene ring may have 1 to 4 same or different substituents selected from a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, and a cyano group, $R^6$ and $R^7$ may be the same as or different from each other and represent a hydrogen atom, a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group, W represents $CR^{10}$ or N, where, $R^{10}$ represents any of the groups represented by $R^6$ described above, and "—" represents a bond.)

(3)

The compound, a tautomer or stereoisomer of the compound, or a pharmaceutically acceptable salt or solvate thereof according to (2), in which $R^4$ and $R^5$ may form a benzene ring together with two carbon atoms to which $R^4$ and $R^5$ are bonded or may be the same as or different from each other and represent a hydrogen atom, a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, or a cyano group, where, the benzene ring may have 1 to 4 same as or different substituents selected from a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, and a cyano group, and $R^6$ and $R^7$ may be the same as or different from each other and represent a hydrogen atom, a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, or a cyano group, (4)

The compound represented by Formula (I), and a tautomer or a stereoisomer of the compound, or a pharmaceutically acceptable salt or solvate thereof according to any one of (1) to (3), in which Q represents $CR^8$, the ring formed of dotted lines represents a benzene ring, and $R^3$ and $R^8$ are bonded to each other to form a naphthalene ring together with two carbon atoms to which $R^3$ and $R^8$ are bonded.

(5)

The compound represented by Formula (I), and a tautomer or a stereoisomer of the compound, or a pharmaceutically acceptable salt or solvate thereof according to any one of (1) to (3), in which Q represents $CR^8$, the ring formed of dotted lines represents a benzene ring, and $R^3$ and $R^8$ are bonded to each other to form a 5-membered heteroaryl ring containing 1 to 3 heteroatoms, as a ring constituent element, selected from a nitrogen atom, an oxygen atom, and a sulfur atom together with two carbon atoms to which $R^3$ and $R^8$ are bonded.

(6)

The compound represented by Formula (I), and a tautomer or a stereoisomer of the compound, or a pharmaceutically acceptable salt or solvate thereof according to any one of (1) to (3), in which Q represents $CR^8$, the ring formed of dotted lines represents a benzene ring, and $R^3$ and $R^8$ are bonded to each other to form thiazole or isothiazole together with two carbon atoms to which $R^3$ and $R^8$ are bonded.

(7)

The compound represented by Formula (I), a tautomer or stereoisomer of the compound, or a pharmaceutically acceptable salt or solvate thereof according to any one of (1) to (3), in which, in a case where $R^1$, $R^2$, $R^3$, and $R^8$ do not constitute a ring, $R^1$, $R^2$, $R^3$, and $R^8$ may be the same as or different from each other and represent a hydrogen atom, a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group.

(8)

The compound represented by Formula (I), a tautomer or stereoisomer of the compound, or a pharmaceutically acceptable salt or solvate thereof according to any one of (1) to (3), in which, in a case where $R^1$, $R^2$, $R^3$, and $R^8$ do not constitute a ring, $R^1$, $R^2$, $R^3$, and $R^8$ may be the same as or different from each other and represent a hydrogen atom, a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, or a cyano group.

(9)

The compound represented by Formula (I), a tautomer or stereoisomer of the compound, or a pharmaceutically acceptable salt or solvate thereof according to any one of (1) to (3), in which, in a case where $R^1$, $R^2$, $R^3$, and $R^8$ do not constitute a ring, $R^1$, $R^2$, $R^3$, and $R^8$ may be the same as or different from each other and represent a hydrogen atom, a halogen atom, an alkyl group having 1 to 8 carbon atoms, or an alkyl group having 1 to 8 carbon atoms substituted with 1 to 3 halogen atoms.

(10)

The compound represented by Formula (I), a tautomer or stereoisomer of the compound, or a pharmaceutically acceptable salt or solvate thereof according to any one of (1) to (3), in which the substituent in a case where $R^1$, $R^2$, $R^3$, and $R^8$ constitute a ring represents a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group.

(11)

The compound represented by Formula (I), a tautomer or stereoisomer of the compound, or a pharmaceutically acceptable salt or solvate thereof according to any one of (1) to (3), in which the substituent in a case where $R^1$, $R^2$, $R^3$, and $R^8$ constitute a ring represents a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, or a cyano group.

(12)

The compound represented by Formula (I), a tautomer or stereoisomer of the compound, or a pharmaceutically acceptable salt or solvate thereof according to any one of (1) to (3), in which the substituent in a case where $R^1$, $R^2$, $R^3$, and $R^8$ constitute a ring represents same or different groups selected from a halogen atom, an alkyl group having 1 to 8 carbon atoms, or an alkyl group having 1 to 8 carbon atoms substituted with 1 to 3 halogen atoms.

(13)

The compound, a tautomer or stereoisomer of the compound, or a pharmaceutically acceptable salt or solvate thereof according to any one of (2) to (12), in which $R^4$ and $R^5$ may be the same as or different from each other and represent a hydrogen atom, a halogen atom, or an alkyl group having 1 to 8 carbon atoms.

(14)

The compound, a tautomer or stereoisomer of the compound, or a pharmaceutically acceptable salt or solvate thereof according to any one of (2) to (13), in which $R^6$ and $R^7$ may be the same as or different from each other and represent a hydrogen atom, a halogen atom, an alkyl group having 1 to 8 carbon atoms, or a cyano group.

(15)

The compound, a tautomer or stereoisomer of the compound, or a pharmaceutically acceptable salt or solvate thereof according to any one of (2) to (13), in which $R^6$ represents a cyano group.

(16)

The compound, a tautomer or stereoisomer of the compound, or a pharmaceutically acceptable salt or solvate thereof according to any one of (2) to (15), in which W represents $CR^{10}$.

(17)

The compound, a tautomer or stereoisomer of the compound, or a pharmaceutically acceptable salt or solvate thereof according to (16), in which $R^{10}$ represents a hydrogen atom, a halogen atom, or an alkyl group having 1 to 8 carbon atoms.

(18)

The compound represented by Formula (I), a tautomer or stereoisomer of the compound, or a pharmaceutically acceptable salt or solvate thereof according to any one of (1) to (17), in which X represents an oxygen atom or a sulfur atom.

(19)

The compound represented by Formula (I), a tautomer or stereoisomer of the compound, or a pharmaceutically acceptable salt or solvate thereof according to any one of (1) to (17), in which X represents a sulfur atom.

(20)

The compound represented by Formula (I), a tautomer or stereoisomer of the compound, or a pharmaceutically acceptable salt or solvate thereof according to any one of (1) to (19), in which Y represents an alkylene chain having 1 to 8 carbon atoms, and where, the alkylene chain may be substituted with 1 to 4 same or different groups selected from an alkyl group having 1 to 8 carbon atoms, an alkoxy group having 1 to 8 carbon atoms, an alkyl group having 1 to 8 carbon atoms substituted with 1 to 3 halogen atoms, or an alkoxy group having 1 to 8 carbon atoms substituted with 1 to 3 halogen atoms.

(21)

The compound represented by Formula (I), a tautomer or stereoisomer of the compound, or a pharmaceutically acceptable salt or solvate thereof according to any one of (1) to (19), in which Y represents $C(C_{1-3}$ alkyl$)_2$.

(22)

The compound represented by Formula (I), a tautomer or stereoisomer of the compound, or a pharmaceutically acceptable salt or solvate thereof according to any one of (1) to (19), in which Y represents CH=CH.

(23)

The compound represented by Formula (I), a tautomer or stereoisomer of the compound, or a pharmaceutically acceptable salt or solvate thereof according to any one of (1) to (19), in which Y represents $C(C_{1-3}$ alkyl$)$=CH.

(24)

The compound represented by Formula (I), a tautomer or stereoisomer of the compound, or a pharmaceutically acceptable salt or solvate thereof according to any one of (1) to (19), in which Y is represented by the following Formula (V).

(In the formula, $R^{01}$ and $R^{02}$ may be the same as or different from each other and represent an alkyl group having 1 to 8 carbon atoms or $R^{01}$ and $R^{02}$ are bonded to each other to form a 3- to 7-membered ring together with carbon atoms to which $R^{01}$ and $R^{02}$ are bonded, and "—" represents a bond.)

(25)

The compound represented by Formula (I), a tautomer or stereoisomer of the compound, or a pharmaceutically acceptable salt or solvate thereof according to any one of (1) to (24), in which Z represents $CO_2H$, $CON(R^{12})(R^{13})$, $CO_2(R^{14})$, $SO_2N(R^{15})(R^{16})$, or a tetrazolyl group, where, $R^{12}$, $R^{14}$, and $R^{15}$ represent a hydrogen atom, an alkyl group having 1 to 8 carbon atoms, or an alkyl group having 1 to 8 carbon atoms substituted with 1 to 3 halogen atoms, and $R^{13}$ and $R^{16}$ represent a hydrogen atom, an alkyl group having 1 to 8 carbon atoms, an alkyl group having 1 to 8 carbon atoms substituted with 1 to 3 halogen atoms, a phenyl group which may have a substituent, or a pyridyl group which may have a substituent.

(26)

The compound represented by Formula (I), a tautomer or stereoisomer of the compound, or a pharmaceutically acceptable salt or solvate thereof according to any one of (1) to (24), in which Z represents $CO_2H$.

As the compound of the present invention represented by Formula (II), compounds shown below are preferable.

(27)

A compound represented by Formula (III), a tautomer or stereoisomer of the compound, or a pharmaceutically acceptable salt or solvate thereof, in which $R^{1a}$, $R^{2a}$, $R^{6a}$, and $R^{7a}$ may be the same as or different from each other and represent a hydrogen atom, a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, or a cyano group, $R^{3a}$ and $R^{8a}$ form a benzene ring or a 5-membered heteroaryl ring containing 1 to 3 heteroatoms, as a ring constituent element, selected from a nitrogen atom, an oxygen atom, and a sulfur atom together with two carbon atoms to which $R^{3a}$ and $R^{8a}$ are bonded, where, the benzene ring and the heteroaryl ring may have 1 to 4 same or different substituents selected from a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, and a cyano group, $R^{4a}$ and $R^{5a}$ form a benzene ring together with two carbon atoms to which $R^{4a}$ and $R^{5a}$ are bonded or represent any of the groups represented by $R^{1a}$ described above, and where, the benzene ring may have 1 to 4 same or different substituents selected from a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, and a cyano group.

(28)

The compound represented by Formula (III), a tautomer or stereoisomer of the compound, or a pharmaceutically acceptable salt or solvate thereof according to (27), in which $R^{1a}$, $R^{2a}$, $R^{6a}$, and $R^{7a}$ may be the same as or different from each other and represent a hydrogen atom, an alkyl group having 1 to 8 carbon atoms, an alkoxy group having 1 to 8 carbon atoms, or a cyano group, (29)

The compound represented by Formula (III), a tautomer or stereoisomer of the compound, or a pharmaceutically acceptable salt or solvate thereof according to (27), in which $R^{6a}$ represents a cyano group.

(30)

The compound represented by Formula (III), a tautomer or stereoisomer of the compound, or a pharmaceutically acceptable salt or solvate thereof according to any one of (27) to (29), in which $R^{3a}$ and $R^{8a}$ form a benzene ring together with two carbon atoms to which $R^{3a}$ and $R^{8a}$ are bonded.

(31)
The compound represented by Formula (III), a tautomer or stereoisomer of the compound, or a pharmaceutically acceptable salt or solvate thereof according to any one of (27) to (29), in which the benzene ring formed by $R^{3a}$ and $R^{8a}$ together with two carbon atoms to which $R^{3a}$ and $R^{8a}$ are bonded may be substituted with 1 to 4 groups selected from an alkyl group having 1 to 8 carbon atoms, an alkoxy group having 1 to 8 carbon atoms, or a cyano group.

(32)
The compound represented by Formula (III), a tautomer or stereoisomer of the compound, or a pharmaceutically acceptable salt or solvate thereof according to any one of (27) to (29), in which $R^{3a}$ and $R^{8a}$ form a 5-membered heteroaryl ring containing 2 heteroatoms, as a ring constituent element, selected from a nitrogen atom, an oxygen atom, and a sulfur atom together with two carbon atoms to which $R^{3a}$ and $R^{8a}$ are bonded.

(33)
The compound represented by Formula (III), a tautomer or stereoisomer of the compound, or a pharmaceutically acceptable salt or solvate thereof according to any one of (27) to (29), in which $R^{3a}$ and $R^{8a}$ form thiazole or isothiazole together with two carbon atoms to which $R^{3a}$ and $R^{8a}$ are bonded.

(34)
The compound, a tautomer or stereoisomer of the compound, or a pharmaceutically acceptable salt or solvate thereof according to (33), in which the thiazole or isothiazole formed by $R^{3a}$ and $R^{8a}$ together with two carbon atoms to which $R^{3a}$ and $R^{8a}$ are bonded may be substituted with an alkyl group having 1 to 8 carbon atoms, an alkoxy group having 1 to 8 carbon atoms, or a cyano group.

(35)
The compound represented by Formula (III), a tautomer or stereoisomer of the compound, or a pharmaceutically acceptable salt or solvate thereof according to any one of (27) to (34), in which $R^{4a}$ and $R^{5a}$ may be the same as or different from each other and represent a hydrogen atom, an alkyl group having 1 to 8 carbon atoms, an alkoxy group having 1 to 8 carbon atoms, or a cyano group.

(36)
The compound represented by Formula (III), a tautomer or stereoisomer of the compound, or a pharmaceutically acceptable salt or solvate thereof according to any one of (27) to (35), in which $W^a$ represents $CR^{10a}$.

(37)
The compound represented by Formula (III), a tautomer or stereoisomer of the compound, or a pharmaceutically acceptable salt or solvate thereof according to any one of (27) to (36), in which $X^a$ represents an oxygen atom or a sulfur atom.

(38)
The compound represented by Formula (III), a tautomer or stereoisomer of the compound, or a pharmaceutically acceptable salt or solvate thereof according to any one of (27) to (36), in which $X^a$ represents a sulfur atom.

(39)
The compound represented by Formula (III), a tautomer or stereoisomer of the compound, or a pharmaceutically acceptable salt or solvate thereof according to any one of (27) to (38), in which $Y^a$ represents $C(C_{1-3}\text{ alkyl})_2$.

(40)
The compound represented by Formula (III), a tautomer or stereoisomer of the compound, or a pharmaceutically acceptable salt or solvate thereof according to any one of (27) to (38), in which $Y^a$ is represented by the following Formula (VI).

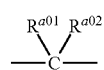

(VI)

(In the formula, $R^{a01}$ and $R^{a02}$ may be the same as or different from each other and represent an alkyl group having 1 to 8 carbon atoms or $R^{a01}$ and $R^{a02}$ are bonded to each other to form a 3- to 7-membered ring together with carbon atoms to which $R^{a01}$ and $R^{a02}$ are bonded, and "—" represents a bond.)

(41)
The compound represented by Formula (III), a tautomer or stereoisomer of the compound, or a pharmaceutically acceptable salt or solvate thereof according to any one of (27) to (40), in which $Z^a$ represents $CO_2H$.

As the compound of the present invention represented by Formula (IV), compounds shown below are preferable.

(42)
The compound represented by Formula (IV), a tautomer or stereoisomer of the compound, or a pharmaceutically acceptable salt or solvate thereof,
in which $R^{1b}$, $R^{2b}$, $R^{4b}$, $R^{5b}$, $R^{6b}$, $R^{7b}$, and $R^{10b}$ may be the same as or different from each other and represent a hydrogen atom, a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, or a cyano group,
$R^{3b}$ and $R^{8b}$ represent a 5-membered heteroaryl ring containing, as ring constituent elements, two heteroatoms which are one nitrogen atom and one oxygen atom or one nitrogen atom and one sulfur atom, together with two carbon atoms to which $R^{3b}$ and $R^{8b}$ are bonded, and
where, the heteroaryl ring may have a substituent selected from a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, and a cyano group.

(43)
The compound represented by Formula (IV), a tautomer or stereoisomer of the compound, or a pharmaceutically acceptable salt or solvate thereof according to (42), in which $R^{1b}$, $R^{2b}$, $R^{4b}$, $R^{5b}$, $R^{6b}$, $R^{7b}$, and $R^{10b}$ may be the same as or different from each other and represent a hydrogen atom, an alkyl group having 1 to 8 carbon atoms, an alkoxy group having 1 to 8 carbon atoms, or a cyano group.

(44)
The compound represented by Formula (IV), a tautomer or stereoisomer of the compound, or a pharmaceutically acceptable salt or solvate thereof according to (42), in which $R^{6b}$ represents a cyano group.

(45)
The compound represented by Formula (III), a tautomer or stereoisomer of the compound, or a pharmaceutically acceptable salt or solvate thereof according to any one of (42) to (44), in which $R^{3b}$ and $R^{8b}$ form thiazole or isothiazole together with two carbon atoms to which $R^{3b}$ and $R^{8b}$ are bonded.

(46)
The compound, a tautomer or stereoisomer of the compound, or a pharmaceutically acceptable salt or solvate thereof according to (45), in which the thiazole or isothiazole formed by $R^{3b}$ and $R^{8b}$ together with two carbon atoms to which $R^{3b}$ and $R^{8b}$ are bonded may be substituted with a substituent selected from an alkyl group having 1 to 8 carbon atoms, an alkoxy group having 1 to 8 carbon atoms, and a cyano group.

(47)
The compound represented by Formula (IV), a tautomer or stereoisomer of the compound, or a pharmaceutically acceptable salt or solvate thereof according to any one of (42) to (46), in which $X^b$ represents a sulfur atom.

(48)
The compound represented by Formula (IV), a tautomer or stereoisomer of the compound, or a pharmaceutically acceptable salt or solvate thereof according to any one of (42) to (47), in which $Y^b$ represents $C(C_{1-3}$ alkyl$)_2$.

(49)
The compound represented by Formula (IV), a tautomer or stereoisomer of the compound, or a pharmaceutically acceptable salt or solvate thereof according to any one of (42) to (47),
in which $Y^b$ is represented by the following Formula (VII).

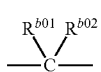

(VII)

(In the formula, $R^{b01}$ and $R^{b02}$ may be the same as or different from each other and represent an alkyl group having 1 to 8 carbon atoms or $R^{b01}$ and $R^{b02}$ are bonded to each other to form a 3- to 7-membered ring together with carbon atoms to which $R^{b01}$ and $R^{b02}$ are bonded.)

As the compounds of the present invention represented by Formulae (I), (III), and (IV), compounds shown below are preferable.

(50)
A compound selected from the following compounds, a tautomer or stereoisomer of the compound, or a pharmaceutically acceptable salt or solvate thereof,
ethyl 2-[[4'-cyano-(1,1'-binaphthalene)-2-yl]oxy]-2-methylpropanoate,
2-[[4'-cyano-(1,1'-binaphthalene)-2-yl]oxy]-2-methylpropanoic acid,
ethyl 2-[[4'-cyano-(1,1'-binaphthalene)-2-yl]thio]-2-methylpropanoate,
2-[[4'-cyano-(1,1'-binaphthalene)-2-yl]thio]-2-methylpropanoic acid,
t-butyl (E)-3-[[1-(4-cyanophenyl)naphthalen-2-yl]oxy]acrylate,
(E)-3-[[1-(4-cyanophenyl)naphthalen-2-yl]oxy]acrylic acid,
(Z)-3-[[1-(4-cyanophenyl)naphthalen-2-yl]oxy]acrylic acid,
2-methyl-2-[[1-(pyridin-3-yl)naphthalen-2-yl]oxy]propanoic acid,
methyl (E)-3-[[1-(pyridin-3-yl)naphthalen-2-yl]oxy]acrylate,
(E)-3-[[1-(pyridin-3-yl)naphthalen-2-yl]oxy]acrylic acid,
(Z)-3-[[1-(pyridin-3-yl)naphthalen-2-yl]oxy]acrylic acid,
ethyl 2-[[5-(4-cyanophenyl)quinolin-6-yl]oxy]-2-methylpropanoate,
2-[[5-(4-cyanophenyl)quinolin-6-yl]oxy]-2-methylpropanoic acid,
ethyl 2-[[5-(4-cyanophenyl)quinolin-6-yl]thio]-2-methylpropanoate,
2-[[5-(4-cyanophenyl)quinolin-6-yl]thio]-2-methylpropanoic acid,
ethyl 2-[[7-(4-cyanophenyl)benzo[d]oxazol-6-yl]oxy]-2-methylpropanoate,
2-[[7-(4-cyanophenyl)benzo[d]oxazol-6-yl]oxy]-2-methylpropanoic acid,
ethyl 2-[[7-(4-cyanophenyl)benzo[d]thiazol-6-yl]oxy]-2-methylpropanoate,
2-[[7-(4-cyanophenyl)benzo[d]thiazol-6-yl]oxy]-2-methylpropanoic acid,
t-butyl (E)-3-[[7-(4-cyanophenyl)benzo[d]thiazol-6-yl]oxy]acrylate,
(E)-3-[[7-(4-cyanophenyl)benzo[d]thiazol-6-yl]oxy]acrylic acid,
ethyl 2-[[7-(4-cyanophenyl)benzo[d]thiazol-6-yl]thio]-2-methylpropanoate,
t-butyl 2-[[7-(4-cyanophenyl)benzo[d]thiazol-6-yl]thio]-2-methylpropanoate,
2-[[7-(4-cyanophenyl)benzo[d]thiazol-6-yl]thio]-2-methylpropanoic acid,
ethyl 2-[[7-(4-cyanophenyl)benzo[d]isothiazol-6-yl]oxy]-2-methylpropanoate,
2-[[7-(4-cyanophenyl)benzo[d]isothiazol-6-yl]oxy]-2-methylpropanoic acid,
ethyl 2-[[7-(4-cyanophenyl)benzo[d]isothiazol-6-yl]thio]-2-methylpropanoate,
2-[[7-(4-cyanophenyl)benzo[d]isothiazol-6-yl]thio]-2-methyl propanoic acid,
ethyl 2-[[4-(4-cyanophenyl)benzo[c][1,2,5]thiadiazol-5-yl]oxy]-2-methylpropanoate,
2-[[4-(4-cyanophenyl)benzo[c][1,2,5]thiadiazol-5-yl]oxy]-2-methylpropanoic acid,
ethyl 2-[[4-(4-cyanophenyl)benzo[c][1,2,5]thiadiazol-5-yl]thio]-2-methylpropanoate,
2-[[4-(4-cyanophenyl)benzo[c][1,2,5]thiadiazol-5-yl]thio]-2-methylpropanoic acid,
2-[[4-(4-cyanophenyl)-1H-indol-5-yl]oxy]-2-methylpropanoic acid,
ethyl 2-[[6-(4-cyanophenyl)benzo[d]thiazol-5-yl]oxy]-2-methylpropanoate,
2-[[6-(4-cyanophenyl)benzo[d]thiazol-5-yl]oxy]-2-methylpropanoic acid,
ethyl 2-[[6-(4-cyanophenyl)benzo[d]thiazol-7-yl]oxy]-2-methylpropanoate,
2-[[6-(4-cyanophenyl)benzo[d]thiazol-7-yl]oxy]-2-methylpropanoic acid,
ethyl 2-[[6-(4-cyanophenyl)benzo[d]thiazol-7-yl]thio]-2-methylpropanoate,
2-[[6-(4-cyanophenyl)benzo[d]thiazol-7-yl]thio]-2-methylpropanoic acid,
ethyl 2-[[8-(4-cyanophenyl)imidazo[1,2-a]pyridin-7-yl]thio]-2-methylpropanoate,
2-[[8-(4-cyanophenyl)imidazo[1,2-a]pyridin-7-yl]thio]-2-methylpropanoic acid,
ethyl 2-[[6-(4-cyanophenyl)imidazo[1,2-a]pyridin-7-yl]oxy]-2-methylpropanoate,
2-[[6-(4-cyanophenyl)imidazo[1,2-a]pyridin-7-yl]oxy]-2-methylpropanoic acid,
ethyl 2-[[3-(4-cyanophenyl)quinolin-4-yl]thio]-2-methylpropanoate,
2-[[3-(4-cyanophenyl)quinolin-4-yl]thio]-2-methylpropanoic acid,
ethyl (E)-3-[[1-(4-cyanophenyl)naphthalen-2-yl]oxy]-2-butenoate, (E)-3-[[1-(4-cyanophenyl)naphthalen-2-yl]oxy]-2-butenoic acid,
t-butyl 2-[[1-(4-cyanophenyl)naphthalen-2-yl]thio]-2-methylpropanoate,
2-[[1-(4-cyanophenyl)naphthalen-2-yl]thio]-2-methylpropanoic acid,
t-butyl (E)-3-[[1-(4-cyanophenyl)naphthalen-2-yl]thio]acrylate,
(E)-3-[[1-(4-cyanophenyl)naphthalen-2-yl]thio]acrylic acid,
2-[[7-(4-cyanophenyl)benzo[d]thiazol-6-yl]thio]-2-methylpropanamide,
2-[[7-(4-cyanophenyl)benzo[d]thiazol-6-yl]thio]-N-(5-fluoropyridin-2-yl)-2-methylpropanamide,
2-[[7-(4-cyanophenyl)benzo[d]thiazol-6-yl]thio]-2-methyl-N-(1,3,4-thiadiazol-2-yl)propanamide,
t-butyl 2-[[4-(4-cyanophenyl)benzo[d]thiazol-5-yl]oxy]-2-methylpropanoate, and
2-[[4-(4-cyanophenyl)benzo[d]thiazol-5-yl]oxy]-2-methylpropanoic acid.

(51)
A compound selected from the following compounds, a tautomer or stereoisomer of the compound, or a pharmaceutically acceptable salt or solvate thereof,
ethyl (E)-3-[[1-(4-cyanophenyl)naphthalen-2-yl]oxy]-2-pentenoate,
(E)-3-[[1-(4-cyanophenyl)naphthalen-2-yl]oxy]-2-pentenoic acid,
t-butyl 2-[[7-(4-cyanophenyl)-2-(trifluoromethyl)benzo[d]thiazol-6-yl]thio]-2-methylpropanoic acid,
2-[[7-(4-cyanophenyl)-2-(trifluoromethyl)benzo[d]thiazol-6-yl]thio]-2-methylpropanoic acid,
ethyl 2-[[7-(4-cyanophenyl)-2-methylbenzo[d]thiazol-6-yl]thio]-2-methylpropanoate,
2-[[7-(4-cyanophenyl)-2-methylbenzo[d]thiazol-6-yl]thio]-2-methylpropanoic acid,
t-butyl 2-methyl-2-[[7-[4-(trifluoromethoxy)phenyl]benzo[d]thiazol-6-yl]thio]propanoate,
2-methyl-2-[[7-[4-(trifluoromethoxy)phenyl]benzo[d]thiazol-6-yl]thio]propanoic acid,
ethyl 1-[[7-(4-cyanophenyl)benzo[d]isothiazol-6-yl]thio]cyclobutan-1-carboxylate,
1-[[7-(4-cyanophenyl)benzo[d]isothiazol-6-yl]thio]cyclobutan-1-carboxylic acid,
methyl 1-[[7-(4-cyanophenyl)benzo[d]isothiazol-6-yl]thio]cyclopentan-1-carboxylate,
1-[[7-(4-cyanophenyl)benzo[d]isothiazol-6-yl]thio]cyclopentan-1-carboxylic acid,
methyl 2-[[7-(4-cyanophenyl)benzo[d]isothiazol-6-yl]thio]-3-methylbutanoate,
2-[[7-(4-cyanophenyl)benzo[d]isothiazol-6-yl]thio]-3-methylbutanoic acid,
ethyl 2-methyl-2-[[7-(4-nitrophenyl)benzo[d]isothiazol-6-yl]thio]propanoate,
2-methyl-2-[[7-(4-nitrophenyl)benzo[d]isothiazol-6-yl]thio]propanoic acid,
t-butyl 2-methyl-2-[[7-(p-tolyl)benzo[d]isothiazol-6-yl]thio]propanoate,
2-methyl-2-[[7-(p-tolyl)benzo[d]isothiazol-6-yl]thio]propanoic acid,
t-butyl 2-methyl-2-[[7-(4-isopropylphenyl)benzo[d]isothiazol-6-yl]thio]-2-methylpropanoate,
2-[[7-(4-isopropylphenyl)benzo[d]isothiazol-6-yl]thio]-2-methylpropanoic acid,
t-butyl 2-methyl-2-[[7-[4-(trifluoromethyl)phenyl]benzo[d]isothiazol-6-yl]thio]propanoate,
2-methyl-2-[[7-[4-(trifluoromethyl)phenyl]benzo[d]isothiazol-6-yl]thio]propanoic acid,
t-butyl 2-methyl-2-[[7-[4-(trifluoromethoxy)phenyl]benzo[d]isothiazol-6-yl]thio]propanoate,
2-methyl-2-[[7-[4-(trifluoromethoxy)phenyl]benzo[d]isothiazol-6-yl]thio]propanoic acid,
t-butyl 2-methyl-2-[[7-(4-chlorophenyl)benzo[d]isothiazol-6-yl]thio]-2-methylpropanoate,
2-[[7-(4-chlorophenyl)benzo[d]isothiazol-6-yl]thio]-2-methylpropanoic acid,
t-butyl 2-[[7-(3-cyanophenyl)benzo[d]isothiazol-6-yl]thio]-2-methylpropanoate,
2-[[7-(3-cyanophenyl)benzo[d]isothiazol-6-yl]thio]-2-methylpropanoic acid,
ethyl 2-[[7-(4-cyano-2-methylphenyl)benzo[d]isothiazol-6-yl]thio]-2-methylpropanoate,
2-[[7-(4-cyano-2-methylphenyl)benzo[d]isothiazol-6-yl]thio]-2-methylpropanoic acid,
t-butyl 2-[[7-(4-cyano-3-methylphenyl)benzo[d]isothiazol-6-yl]thio]-2-methyl propanoate,
2-[[7-(4-cyano-3-methylphenyl)benzo[d]isothiazol-6-yl]thio]-2-methylpropanoic acid,
t-butyl 2-[[7-(4-cyano-3-fluorophenyl)benzo[d]isothiazol-6-yl]thio]-2-methylpropanoate,
2-[[7-(4-cyano-3-fluorophenyl)benzo[d]isothiazol-6-yl]thio]-2-methylpropanoic acid,
t-butyl 2-[[7-(4-fluoronaphthalen-1-yl)benzo[d]isothiazol-6-yl]thio]-2-methylpropanoate,
2-[[7-(4-fluoronaphthalen-1-yl)benzo[d]isothiazol-6-yl]thio]-2-methylpropanoic acid,
t-butyl 2-[[7-(4-cyanonaphthalen-1-yl)benzo[d]isothiazol-6-yl]thio]-2-methylpropanoate,
2-[[7-(4-cyanonaphthalen-1-yl)benzo[d]isothiazol-6-yl]thio]-2-methylpropanoic acid,
t-butyl 2-methyl-2-[[7-(pyridin-3-yl)benzo[d]isothiazol-6-yl]thio]propanoate,
2-methyl-2-[[7-(pyridin-3-yl)benzo[d]isothiazol-6-yl]thio]propanoic acid,
ethyl 2-methyl-2-[[7-(pyridin-4-yl)benzo[d]isothiazol-6-yl]thio]propanoate,
2-methyl-2-[[7-(pyridin-4-yl)benzo[d]isothiazol-6-yl]thio]propanoic acid,
ethyl 2-methyl-2-[[7-[6-(methylthio)pyridin-3-yl]benzo[d]isothiazol-6-yl]thio]propanoate,
2-methyl-2-[[7-[6-(methylthio)pyridin-3-yl]benzo[d]isothiazol-6-yl]thio]propanoic acid,
t-butyl 2-[[7-(4-cyanophenyl)-4-fluorobenzo[d]isothiazol-6-yl]thio]-2-methylpropanoate,
2-[[7-(4-cyanophenyl)-4-fluorobenzo[d]isothiazol-6-yl]thio]-2-methyl propanoic acid,
t-butyl 2-[[7-(4-cyanophenyl)-5-fluorobenzo[d]isothiazol-6-yl]thio]-2-methylpropanoate,
2-[[7-(4-cyanophenyl)-5-fluorobenzo[d]isothiazol-6-yl]thio]-2-methylpropanoic acid,
ethyl 2-[[7-(4-cyanophenyl)-3-methylbenzo[d]isothiazol-6-yl]oxy]-2-methylpropanoate,
2-[[7-(4-cyanophenyl)-3-methylbenzo[d]isothiazol-6-yl]oxy]-2-methylpropanoic acid,
ethyl 2-[[7-(4-cyanophenyl)-3-methylbenzo[d]isothiazol-6-yl]thio]-2-methylpropanoate,
2-[[7-(4-cyanophenyl)-3-methylbenzo[d]isothiazol-6-yl]thio]-2-methylpropanoic acid,
t-butyl 5-[6-[[1-(t-butoxy)-2-methyl-1-oxopropan-2-yl]thio]-3-methylbenzo[d]isothiazol-7-yl]picolinate, and
2-[[7-[6-(ethoxycarbonyl)pyridin-3-yl]-3-methylbenzo[d]isothiazol-6-yl]thio]-2-methylpropanoic acid.

(52)

A compound selected from the following compounds, a tautomer or stereoisomer of the compound, or a pharmaceutically acceptable salt or solvate thereof, ethyl 5-[6-[[1-(t-butoxy)-2-methyl-1-oxopropan-2-yl]thio]-3-methylbenzo[d]isothiazol-7-yl]picolinate, ethyl 1-[[7-(4-cyanophenyl)-3-methylbenzo[d]isothiazol-6-yl]thio]cyclobutan-1-carboxylate, 1-[[7-(4-cyanophenyl)-3-methylbenzo[d]isothiazol-6-yl]thio]cyclobutan-1-carboxylic acid, 2-[[7-(4-cyanophenyl)benzo[d]isothiazol-6-yl]thio]-2-ethylbutanoic acid, 2-[[7-(4-cyanophenyl)benzo[d]isothiazol-6-yl]thio]-3,3-dimethylbutanoic acid, t-butyl (E)-3-[[1-(4-cyanophenyl)naphthalen-2-yl]thio]-2-butenoate, (E)-3-[[1-(4-cyanophenyl)naphthalen-2-yl]thio]-2-butenoic acid, and 1-[[7-(4-cyanophenyl)benzo[d]isothiazol-6-yl]thio]cyclohexan-1-carboxylic acid.

Examples of the pharmacologically acceptable salt of the compound represented by Formula (I), (III), or (IV) include acid addition salts with mineral acid such as hydrochloric acid, sulfuric acid, or phosphoric acid, acid addition salts with organic acid such as formic acid, acetic acid, citric acid, tartaric acid, or methanesulfonic acid, salts with an inorganic base such as a sodium salt, a potassium salt, a lithium salt, or calcium salt, and base addition salts with an organic base such as arginine or piperazine.

Further, cis-trans isomers or stereoisomers such as optically active substance or a racemic body may be present in the compound of the present invention and all of these are included in the range of the present invention.

In addition, the compound of the present invention may be a tautomer, a solvate with an organic solvent such as a hydrate or alcohol, a derivative substituted with a stable isotope such as deuterium, or a prodrug.

Hereinafter, synthesis schemes of the compound of the present invention which is represented by Formula (I), (III), or (IV) will be described.

(1) In case where X represents oxygen atom, Y represents $C(CH_3)_2$, and Z represents $CO_2H$ or $CO_2(R_{14})$

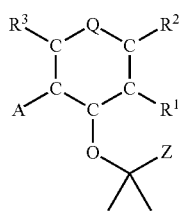

<Method A>
(First Process)

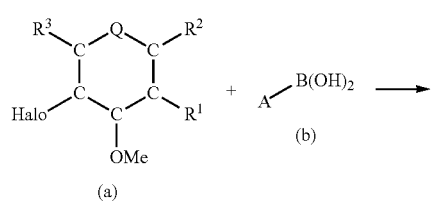

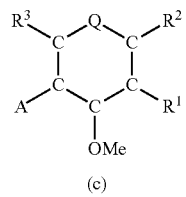

(Second Process)

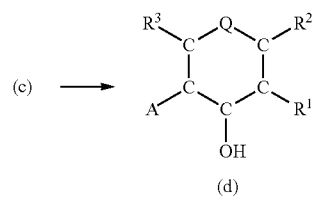

(Third Process)

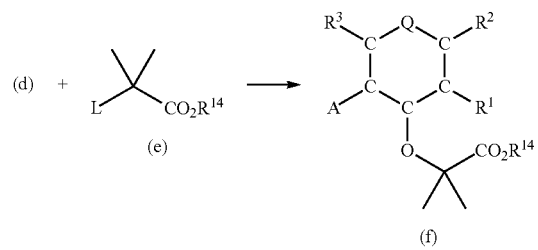

(Fourth Process)

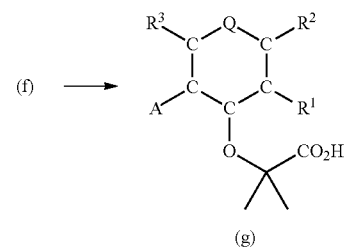

(In the formula, Halo represents halogen such as chlorine, bromine, or iodine, L represents a halogen atom or a leaving group such as a methanesulfonyloxy group, and $R^1$, $R^2$, $R^3$, $R^{14}$, Q, A, and dotted lines represent the same as those described above.)

1) A starting material (a) can be synthesized by a known method (WO2012/145728, WO2007/121484, or the like) or a method similar to those known methods. Further, a starting material (b) can be synthesized by a known method (Glen J. Pernia et al., J. Am. Chem. Soc., 1996, 118, 10220, WO2001/021606, or the like) or a method similar to those known methods.

2) First Process

In a coupling reaction of the starting material (a) and the starting material (b), a compound of Formula (c) can be obtained by a reaction using a catalyst such as tetrakis(triphenylphosphine)palladium, [1,1'-bis(diphenylphosphino)ferrocene]palladium (II) dichloride dichloromethane complex, tris(dibenzylideneacetone)dipalladium, or the like in the presence of a base such as potassium carbonate, cesium carbonate, sodium carbonate, potassium phosphate, potassium t-butoxide, sodium t-butoxide, or the like, and in the presence or absence of an additive such as triphenylphosphino, cesium fluoride, or the like in a solvent which is not involved in a reaction such as toluene, tetrahydrofuran, dioxane, 1,2-dimethoxyethane, ethanol water, or the like. In this case, the reaction temperature is in a range of 60° C. to 110° C.

3) Second Process

In a demethylation reaction of a compound of Formula (c), a compound of Formula (d) can be obtained by a method of using boron tribromide in a solvent which is not involved in a reaction such as dichloromethane, or the like, or a method of conducting a reaction in a temperature range of 130° C. to 200° C. using lithium bromide in the presence of an additive such as p-toluenesulfonic acid monohydrate, or the like in a solvent which is not involved in a reaction such as N,N-dimethylformamide, or the like, or a method of conducting a reaction using pyridine hydrochloride, or the like in the absence of a solvent in a temperature range of 200° C. to 230° C.

4) Third Process

In an alkylation reaction of compounds of Formulae (d) and (e), a compound (f) of the present invention can be obtained by conducting a reaction in the presence of a base such as potassium carbonate, sodium carbonate, cesium carbonate, or the like in a solvent which is not involved in a reaction such as acetonitrile, N,N-dimethylformamide, or the like. In this case, the reaction temperature is in a range of room temperature to 80° C.

5) Fourth Process

A compound (g) of the present invention can be obtained by a method of treating the compound of Formula (f) serving as the compound of the present invention and a production intermediate with lithium hydroxide, sodium hydroxide aqueous solution, potassium hydroxide aqueous solution, or the like in a solvent such as methanol, ethanol water, or the like, or with trifluoroacetic acid, or the like in a solvent which is not involved in a reaction such as dichloromethane, or the like, or in the absence of a solvent.

Further, a compound of Formula (c) can be produced by the following method B.

<Method B>

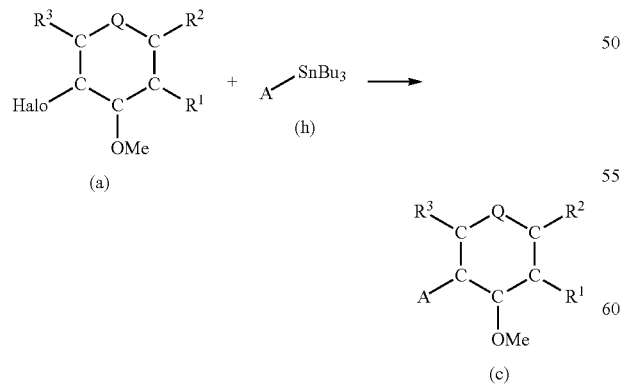

(In the formula, Halo represents halogen such as chlorine, bromine, or iodine and $R^1$, $R^2$, $R^3$, Q, A, and dotted lines represent the same as those described above.)

A starting material (h) can be synthesized by a known method (Pingping Tang et al., J. Am. Chem. Soc., 2010, 132, 12150, WO2001/055146, or the like) or a method similar to those known methods. Further, a coupling reaction of the starting material (a) and the starting material (h) can be performed using the same method as the method A described above.

Further, a compound of Formula (c) can be produced by the following method C.

<Method C>

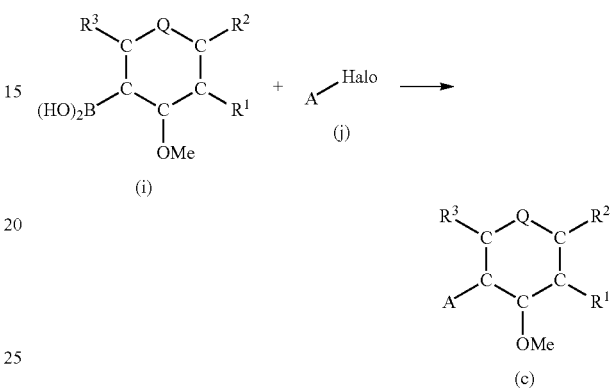

(In the formula, Halo represents halogen such as chlorine, bromine, or iodine and $R^1$, $R^2$, $R^3$, Q, and A represent the same as those described above.)

A starting material (i) can be synthesized by a known method (WO2002/0019527, or the like) or a method similar to those known methods. A starting material (j) can be synthesized by a known method (Lei Yu et al., Org. Lett., 2014, 16, 1346, or the like) or a method similar to those known methods. Further, a coupling reaction of the starting material (i) and the starting material (j) can be performed using the same method as the A method described above.

(2) In case where X represents sulfur atom, Y represents $C(CH_3)_2$, and Z represents $CO_2H$ or $CO_2(R^{14})$

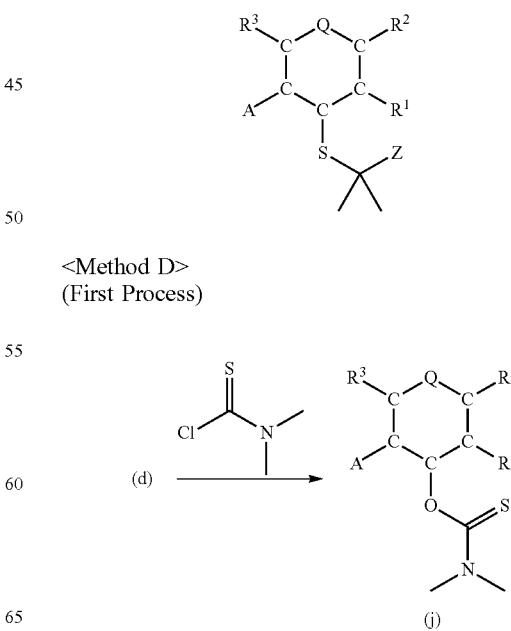

<Method D>
(First Process)

(Second Process)

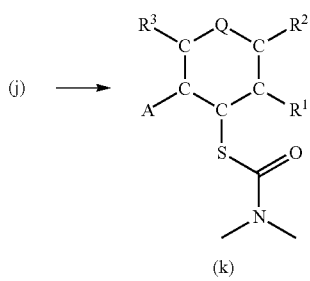

(Third Process)

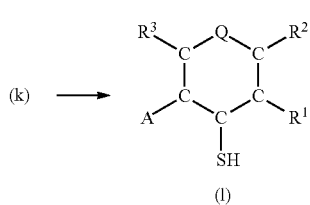

(Fourth Process)

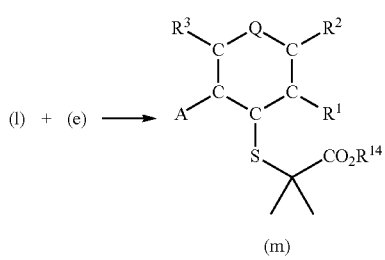

(Fifth Process)

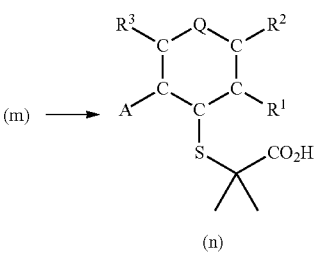

(In the formula, L represents a halogen atom or a leaving group such as a methanesulfonyloxy group and $R^1$, $R^2$, $R^3$, $R^{14}$, Q, A, and dotted lines represent the same as those described above.)

1) First Process

In a thiocarbamoylation reaction of a compound of Formula (d), a compound of Formula (j) can be obtained using dimethylthiocarbamoyl chloride, or the like in the presence of a base such as triethylamine, pyridine, 1,4-diazabicyclo[2.2.2]octane, or the like in the presence of an additive such as dimethylaminopyridine, or the like in a solvent which is not involved in a reaction such as tetrahydrofuran, dioxane, 1,2-dimethoxyethane, or the like.

In this case, the reaction temperature is in a range of 60° C. to 80° C.

2) Second Process

In a rearrangement reaction of a compound of Formula (j), a compound of Formula (k) can be obtained by conducting a reaction in a solvent which is not involved in a reaction such as diphenyl ether, tetradecane, or the like or in the absence of a solvent. In this case, the reaction temperature is in a range of 200° C. to 250° C.

3) Third Process

In a solvolytic reaction of a compound of Formula (k), a compound of Formula (l) can be obtained using sodium methoxide, sodium ethoxide, sodium hydroxide, or the like in a solvent such as methanol, ethanol, water, or the like. In this case, the reaction temperature is in a range of 20° C. to 70° C.

4) Fourth Process

An alkylation reaction of compounds of Formulae (l) and (e) can be performed using the same method as described in the third process of the method A.

5) Fifth Process

In a reaction of a compound of Formula (m) serving as the compound of the present invention and a production intermediate, a compound (n) of the present invention can be obtained using the same method as described in the fourth process of the method A.

Further, the compound of Formula (I) can be produced using the following method E.

<Method E>

(First Process)

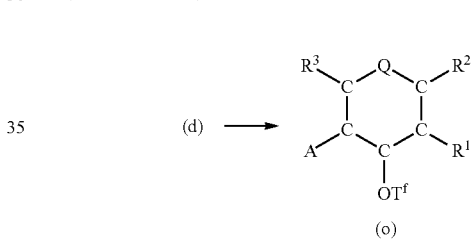

(Second Process)

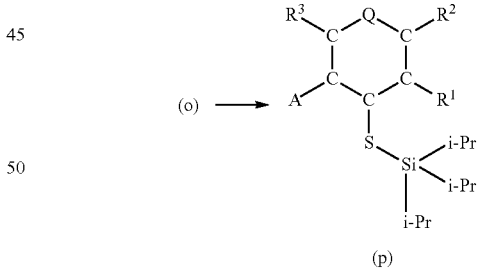

(Third Process)

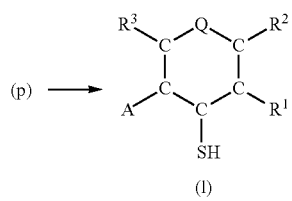

(In the formula, $R^1$, $R^2$, $R^3$, Q, A, and dotted lines represent the same as those described above.)

1) First Process

In a trifluoromethanesulfonate reaction of a compound of Formula (d), a compound of Formula (o) can be obtained using a trifluoromethanesulfonic anhydride, N-phenylbis(trifluoromethanesulfonimide), or the like in the presence of a base such as triethylamine, potassium carbonate, or the like and in the presence of an additive such as dimethylaminopyridine, or the like in a solvent which is not involved in a reaction such as dichloromethane, N,N-dimethylformamide, or the like.

2) Second Process

In a coupling reaction of a compound of Formula (o), a compound of Formula (p) by a method of using a catalyst such as palladium acetate, or the like in the presence of a base such as potassium carbonate, cesium carbonate, sodium carbonate, potassium t-butoxide, sodium t-butoxide, lithiumbis(trimethylsilyl)amide, or the like and in the presence or absence of an additive such as triphenylphosphine, (2R)-1-[(1R)-1-[bis(1,1-dimethylethyl)phosphino]ethyl]-2-(dicyclohexylphosphino)ferrocene, or the like in a solvent which is not involved in a reaction such as toluene, dioxane, 1,2-dimethoxyethane, or the like or by a method of using a catalyst such as palladium acetate, or the like in the presence of a base such as potassium carbonate, cesium carbonate, sodium carbonate, or the like and in the presence of an additive such as 2-dicyclohexylphosphino-2',4',6'-triisopropylbiphenyl, or the like in a solvent which is not involved in a reaction such as t-butanol, water, or the like. In this case, the reaction temperature is in a range of 70° C. to 110° C.

3) Third Process

In a desilylation reaction of a compound of Formula (p), a compound of Formula (I) can be obtained by a method of using tetrabutyl ammonium fluoride or the like in a solvent which is not involved in a reaction such as tetrahydrofuran or the like, or a method of using an acidic aqueous solution such as hydrochloric acid, sulfuric acid, or the like.

(3) In case where X represents oxygen atom or sulfur atom, Y represents CH=CH, and Z represents $CO_2H$ or $CO_2(R^{14})$

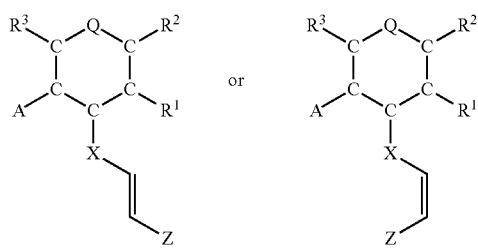

<Method F>

(First Process)

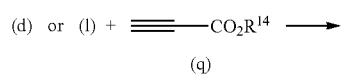

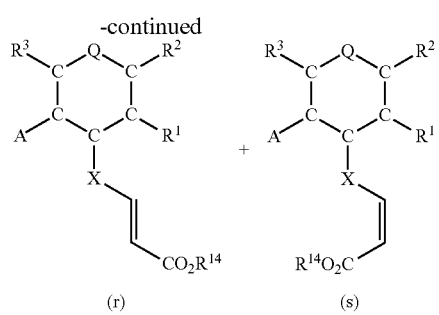

(Second Process)

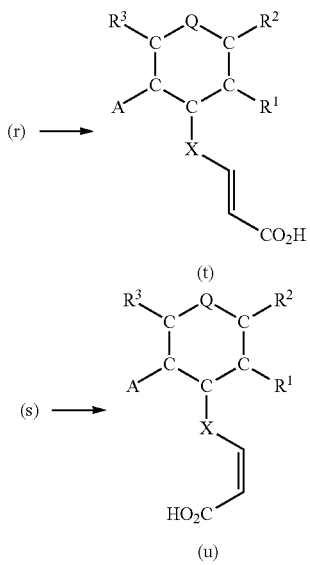

(In the formula, $R^1$, $R^2$, $R^3$, $R^{14}$, X, Q, A, and dotted lines represent the same as those described above.)

(First Process)

In an alkenylation reaction of compounds of Formula (d) or (I) and Formula (q), a compound (r) or (s) of the present invention can be obtained in the presence of a base such as potassium carbonate, sodium carbonate, 1,4-diazabicyclo[2.2.2]octane, or the like in a solvent which is not involved in a reaction such as dichloromethane, N,N-dimethylformamide, acetonitrile, tetrahydrofuran, or the like.

(Second Process)

In a reaction of a compound of Formula (r) or (s) serving as the compound of the present invention and a synthetic intermediate, a compound (t) or (u) of the present invention can be obtained using the same method as described in the fourth process of the method A.

(4) In case where X represents oxygen atom or sulfur atom, Y represents $C(CH_3)_2$ or CH=CH, and Z represents $CON(R^{12})(R^{13})$

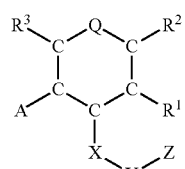

<Method G>
(First Process)

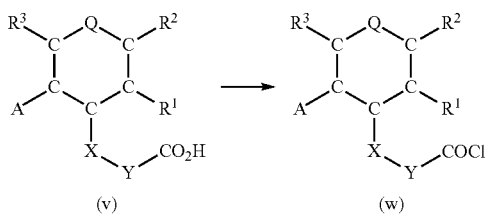

(Second Process)

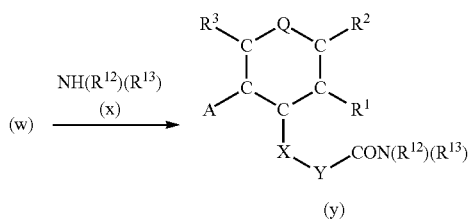

(In the formula, $R^1$, $R^2$, $R^3$, $R^{12}$, $R^{13}$, X, Y, Q, A, and dotted lines represent the same as those described above.)

(First Process)

In an acid chloridization reaction of a compound of Formula (v), a compound of Formula (w) serving as an intermediate can be obtained by conducting the reaction in the presence of thionyl chloride, oxalyl chloride, or the like in a solvent which is not involved in a reaction such as toluene, dichloromethane, or the like.

(Second Process)

In an amidation reaction of compounds of Formulae (w) and (x), a compound (y) of the present invention can be obtained by a method of conducting the reaction in a solvent which is not involved in a reaction such as tetrahydrofuran, 1,2-dimethoxyethane, or the like or by a method of reacting the compound represented by Formula (w) with an ammonia aqueous solution in a case where $R^{12}$ and $R^{13}$ represent hydrogen.

Further, the compound (y) of the present invention can be produced by the following method H.

<Method H>

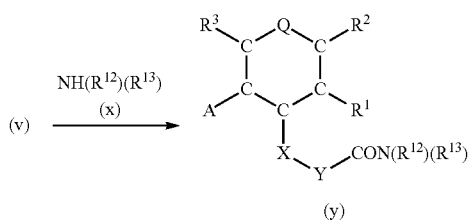

In an amidation reaction of compounds of Formulae (v) and (x), a compound (y) of the present invention can be obtained using a dehydrative condensation agent such as 1-(3-dimethylaminopropyl)-3-ethylcarbodiimide hydrochloride, N,N,N',N'-tetramethyl-O-(7-azabenzotriazol-1-yl) uranium hexafluorophosphate, or the like in the presence of a base such as triethylamine, diisopropyl ethyl amine, or the like in a solvent which is not involved in a reaction such as dichloromethane, N,N-dimethylformamide, tetrahydrofuran, or the like.

Other compounds of the presents invention represented by Formula (I), (III), or (IV) can be produced by referring to the above-described synthetic schemes, synthesis examples described below, and the above-described patent literatures.

The pharmacological action of the compound of the present invention will be described below.

The present inventors tested the action on URAT1 which is a uric acid transporter that is involved in the uptake of uric acid in the kidney.

More specifically, the test is performed by culturing URAT1 stably expressed HEK293 cells (HEK-URAT1) or HEK293 cells transfected with empty vector (HEK-mock) in a DMEM culture medium in an incubator. Subsequently, $1\times10^5$ cells are respectively seeded in 24-well culture plate coated with poly D-lysine and the uptake test is started after the culturing.

The cells are washed with a solution for a test warmed to 37° C. and equilibrated. After a buffer solution is removed from the cells, 0.5 mL of an uptake solution containing 5 µM [$^{14}$C] uric acid with or without a test compound is respectively added and the cells are incubated. The cell uptake is stopped by adding a Hanks buffer solution and the cells are washed. The cells are lysed with 0.1 N sodium hydroxide and the radioactivity is measured using LSC6100 (Aloka Co., Ltd. Tokyo). Each uptake into HEK-URAT1 is acquired by subtracting uptake into HEK-mock cells from the value of HEK-URAT1, converting the result to per mg protein of cells, and setting the values from the uptake without the test compound as 100%.

As listed in Tables 1 to 3 of Examples 118 and 119 described below, it is evident that the compound of the present invention has an excellent URAT1 inhibitory action.

Accordingly, the compound of the present invention represented by Formula (I), (III), or (IV) is expected to serve as an agent for treating or preventing hyperuricemia which has an excellent uric acid excretion promoting action, does not cause severe side effects such as liver failure and cardiac toxicity (hERG), and has high safety.

Further, the compound of the present invention is expected to serve as an agent for treating or preventing gout or hyperuricemia which has an excellent uric acid excretion promoting action, excellent solubility, and excellent metabolic stability in liver microsomes (MS).

However, PLT 1 has a description of "uric acid is a result of xanthine oxidation. Uric acid metabolism disorders are not limited to the following examples and include erythrocytosis, myeloid metaplasia, gout, recurrent gout attack, gouty arthritis, hyperuricemia, hypertension, heart disease, coronary heart disease, Lesch-Nyhan syndrome, Kelly-Siegmiller syndrome, kidney disease, kidney stone, kidney failure, joint inflammation, arthritis, urinary calculi, lead poisoning, hyperparathyroidism, psoriasis, and sarcoidosis". Therefore, there is a possibility that the compound of the present invention having an excellent URAT1 inhibitory action is used for similar diseases.

Further, the compound of the present invention can be used as an agent for treating or preventing gout or hyperuricemia by combining with a XOD inhibitor such as febuxostat, allopurinol, or topiraxostat or a urine alkaline agent such as URALYT (registered trademark) or sodium hydrogen carbonate.

The compound of the present invention can be administered to humans according to a suitable administration method such as oral administration or parenteral administration, but oral administration is preferable.

For formulation, the compound can be produced in dosage forms such as tablets, granules, powders, capsules, suspensions, injections, and suppositories according to a conventional method in the technical field of formulation.

For the preparation, in a case of tablets, typical excipients, disintegrants, binders, lubricants, and dyes are used. Here, examples of the excipients include lactose, D-mannitol, crystalline cellulose, and glucose; examples of the disintegrants include starch and carboxy methyl cellulose calcium (CMC-Ca); examples of the lubricants include magnesium stearate and talc; and examples of the binders include hydroxy propyl cellulose (HPC), gelatin, and polyvinyl pyrrolidone (PVP). For preparation of injections, a solvent, a stabilizer, a solubilizing agent, a suspension, an emulsifier, a soothing agent, a buffer agent, and a preservative are used.

The dosage, for a normal adult, of the compound of the present invention serving as an injection and an active component is in approximately 0.01 mg to 100 mg per day and the dosage for oral administration is in a range of 1 mg to 2000 mg per day. The dosage can be increased or decreased depending on the age, symptoms, and the like.

Next, the present invention will be described in detail with reference to examples, but the present invention is not limited thereto.

EXAMPLE 1

Ethyl 2-[[4'-cyano-(1,1'-binaphthalene)-2-yl]oxy]-2-methyl propanoate

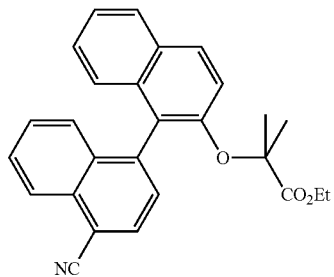 [SMILES: CCOC(=O)C(C)(C)Oc1ccc2ccccc2c1-c1ccc(C#N)c2ccccc12]

(1) 2'-Methoxy-(1,1'-binaphthalene)-4-carbonitrile 4-bromo-1-naphthonitrile (200 mg, 0.86 mmol), (2-methoxynaphthalen-1-yl)boronic acid (260 mg, 1.29 mmol), [1,1'-bis(diphenylphosphino)ferrocene]palladium (II) dichloride dichloromethane adduct (70 mg, 0.09 mmol), potassium t-butoxide (145 mg, 1.92 mmol), and cesium fluoride (196 mg, 1.29 mmol) were dissolved in dioxane (9 mL), and the solution was stirred at 80° C. in a nitrogen atmosphere. After 16 hours, the reaction solution was allowed to be cooled to room temperature, diluted with ethyl acetate, and washed with water and brine. The organic layer was dried over sodium sulfate and filtered, and then the solvent was distilled off under reduced pressure. The obtained residue was purified by silica gel column chromatography (ethyl acetate:hexane=1:2) to obtain a title compound (200 mg, yield of 76%).

$^1$H NMR (CDCl$_3$, 400 MHz): δ=3.77 (s, 3H), 7.03 (d, 1H, J=9Hz), 7.2-7.3 (m, 1H), 7.3-7.5 (m, 3H), 7.44 (d, 1H, J=9Hz), 7.48 (d, 1H, J=7Hz), 7.6-7.7 (m, 1H), 7.88 (d, 1H, J=8Hz), 8.0-8.1 (m, 2H), 8.34 (d, 1H, J=9Hz).

(2) 2'-Hydroxy-(1,1'-binaphthalene)-4-carbonitrile

2'-Methoxy-[1,1'-binaphthalene]-4-carbonitrile (200 mg, 0.65 mmol) obtained in the above-described example was dissolved in dichloromethane (7 mL), 1.0 M boron tribromide solution in dichloromethane (3.25 ml, 3.25 mmol) was added thereto in an ice bath, and the solution was stirred at room temperature in a nitrogen atmosphere. After 3 hours, 7 mL of a 25% ammonia aqueous solution was added to the reaction solution in an ice bath and extraction was carried out using chloroform. The organic layer was dried over sodium sulfate and filtered, and then the solvent was distilled off under reduced pressure. The obtained residue was purified by silica gel column chromatography (ethyl acetate:hexane=1:1) to obtain a title compound (158 mg, yield of 82%).

$^1$H NMR (CDCl$_3$, 400 MHz): δ=6.99 (d, 1H, J=8Hz), 7.2-7.4 (m, 3H), 7.4-7.6 (m, 2H), 7.61 (d, 1H, J=7Hz), 7.7-7.8 (m, 1H), 7.87 (d, 1H, J=8Hz), 7.93 (d, 1H, J =9Hz), 8.10 (d, 1H, J=8Hz), 8.38 (d, 1H, J=8Hz), (3) Ethyl 2-[[4'-cyano-(1,1'-binaphthalene]-2-yl)oxy]-2-methyl propanoate 2'-Hydroxy-[1,1'-binaphthalene]-4-carbonitrile (78 mg, 0.26 mmol) obtained in the above-described example and potassium carbonate (108 mg, 0.78 mmol) were dissolved in dimethylformamide (3 mL), ethyl 2-bromoisobutyrate (58 μL, 0.39 mmol) was added thereto, and the solution was stirred at 60° C. After 16 hours, the reaction solution was allowed to be cooled to room temperature, diluted with ethyl acetate, and washed with water and brine. The organic layer was dried over sodium sulfate and filtered, and then the solvent was distilled off under reduced pressure. The obtained residue was purified by silica gel column chromatography (ethyl acetate:hexane=1:4) to obtain a title compound (108 mg, yield of 100%).

$^1$H NMR (CDCl$_3$, 400 MHz): δ=1.2-1.3 (m, 9H), 4.20 (q, 2H, J=7Hz), 7.08 (d, 1H, J=9Hz), 7.23 (d, 1H, J=9Hz), 7.3-7.6 (m, 5H), 7.68 (t, 1H, J=9Hz), 7.8-8.0 (m, 2H), 8.05 (d, 1H, J=7Hz), 8.34 (d, 1H, J=8Hz).

EXAMPLE 2

2-[(4'-Cyano-(1,1'-binaphthalene)-2-yl]oxy]-2-methylpropanoic acid

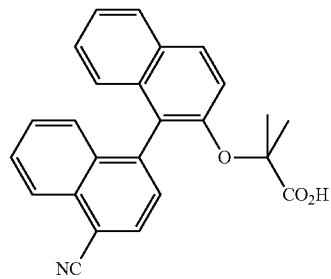 [SMILES: CC(C)(Oc1ccc2ccccc2c1-c1ccc(C#N)c2ccccc12)C(=O)O]

Ethyl 2-[(4'-cyano-[1,1'-binaphthalene]-2-yl)oxy]-2-methyl propanoate (108 mg, 0.26 mmol) obtained in Example 1 was dissolved in methanol (1 mL) and tetrahydrofuran (1 mL), 2 M sodium hydroxide aqueous solution (0.5 mL) was added thereto, and the solution was stirred at room temperature. After 1 hour, 1 M hydrochloric acid (1 mL) was added to the reaction solution to adjust to pH 7 and then the solvent was distilled off under reduced pressure. The obtained residue was purified by silica gel column chromatography (methanol:chloroform=1:10) to obtain a title compound (light yellow crystal, 65 mg, yield of 63%).

$^1$H NMR (CDCl$_3$, 400 MHz): δ=1.24 (s, 6H), 7.08 (d, 1H, J=8Hz), 7.2-7.5 (m, 5H), 7.51 (d, 1H, J=7Hz), 7.68 (t, 1H, J=6Hz), 7.87 (t, 2H, J=6Hz), 8.03 (d, 1H, J=7Hz), 8.34 (d, 1H, J=8Hz).

EXAMPLE 3

Ethyl 2-[(4'-cyano[1,1'-binaphthalene]-2-yl)thio]-2-methyl propanoate

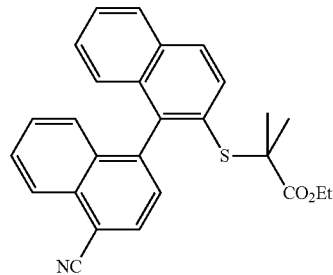 [SMILES: CCOC(=O)C(C)(C)Sc1ccc2ccccc2c1-c1ccc(C#N)c2ccccc12]

(1) Dimethylcarbamothioic acid O-(4'-cyano[1,1'-binaphthalene]-2-yl)

2'-Hydroxy-[1,1'-binaphthalene]-4-carbonitrile (158 mg, 0.53 mmol) obtained in Example 1 (2) and 1,4-diazabicyclo[2.2.2]octane (119 mg, 1.06 mmol) were dissolved in dimethylformamide (5 mL), dimethylthiocarbamoyl chloride (98 mg, 0.80 mmol) was added thereto, and the solution was stirred at 80° C. in a nitrogen atmosphere. After 16 hours, the reaction solution was allowed to be cooled to room temperature, diluted with ethyl acetate, and washed with water and brine. The organic layer was dried over sodium sulfate and filtered, and then the solvent was distilled off under reduced pressure. The obtained residue was purified by silica gel column chromatography (ethyl acetate:hexane=1:2) to obtain a title compound (63 mg, yield of 31%).

$^1$H NMR (CDCl$_3$, 400 MHz): δ=2.55 (s, 3H), 3.17 (s, 3H), 7.17 (d, 1H, J=8Hz), 7.3-7.4 (m, 1H), 7.4-7.6 (m, 4H), 7.66 (d, 1H, J=7Hz), 7.6-7.8 (m, 1H), 7.97 (d, 1H, J=8Hz), 8.0-8.1 (m, 2H), 8.25 (d, 1H, J=8Hz).

(2) Dimethylcarbamothioic acid S-(4'-cyano[1,1'-binaphthalene]-2-yl)

Dimethylcarbamothioic acid O-(4'-cyano[1,1'-binaphthalene]-2-yl) (63 mg, 0.17 mmol) obtained in the above-described example was stirred at 200° C. After 24 hours, the solution was allowed to be cooled to room temperature and the obtained residue was purified by silica gel column chromatography (ethyl acetate:hexane=1:2) to obtain a title compound (25 mg, yield of 40%).

$^1$H NMR (CDCl$_3$, 400 MHz): 2.77 (br s, 3H), 2.90 (br s, 3H), 7.05 (d, 1H, J=8Hz), 7.2-7.8 (m, 6H), 7.76 (d, 1H, J=9Hz), 7.95 (d, 1H, J=8Hz), 8.0-8.1 (m, 2H), 8.36 (d, 1H, J=8Hz).

(3) 2'-Mercapto-[1,1'-binaphthalene]-4-carbonitrile

To dimethylcarbamothioic acid S-(4'-cyano[1,1'-binaphthalene]-2-yl) (25 mg, 0.065 mmol) obtained in the above-described example was added 2 M sodium hydroxide aqueous solution (0.5 mL) and the solution was stirred at room temperature. After 16 hours, 1 M hydrochloric acid (1 mL) was added to the reaction solution to adjust to pH 7 and then the solvent was distilled off under reduced pressure. The obtained residue was purified by silica gel column chromatography (hexane:ethyl acetate=4:1) to obtain a title compound (11 mg, yield of 54%).

$^1$H NMR (CDCl$_3$, 400 MHz): 3.19 (s, 1H), 6.95 (d, 1H, J=8Hz), 7.2-7.3 (m, 1H), 7.35 (d, 1H, J=8Hz), 7.4-7.5 (m, 2H), 7.5-7.6 (m, 2H), 7.7-7.8 (m, 1H), 7.8-8.0 (m, 2H), 8.10 (d, 1H, J=7Hz), 8.39 (d, 1H, J=8Hz).

(4) Ethyl 2-[(4'-cyano-[1,1'-binaphthalene]-2-yl)thio]-2-methyl propanoate

A title compound (12 mg, yield of 80%) was obtained according to the same method as in Example 1 (3) using 2'-mercapto-[1,1'-binaphthalene]-4-carbonitrile (11 mg, 0.035 mmol) obtained in the above-described example.

$^1$H NMR (CDCl$_3$, 400 MHz): δ=1.2-1.3 (m, 9H), 4.11 (q, 2H, J=7Hz), 7.2-7.3 (m, 3H), 7.3-7.5 (m, 3H), 7.63 (d, 1H, J=9Hz), 7.6-7.7 (m, 1H), 7.8-8.0 (m, 2H), 8.04 (d, 1H, J=7Hz), 8.35 (d, 1H, J=9Hz).

EXAMPLE 4

2-[(4'-Cyano[1,1'-binaphthalene]-2-yl)thio]-2-methylpropanoic acid

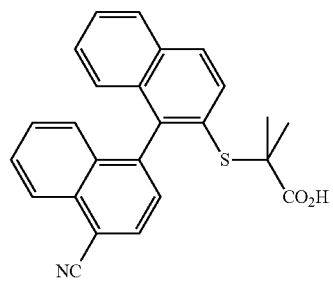 [SMILES: CC(C)(Sc1ccc2ccccc2c1-c1ccc(C#N)c2ccccc12)C(=O)O]

A title compound (white crystal, 9 mg, yield of 81%) was obtained according to the same method as in Example 2 using ethyl 2-[(4'-cyano-[1,1'-binaphthalene]-2-yl)thio]-2-methyl propanoate (12 mg, 0.03 mmol) obtained in Example 3.

$^1$H NMR (CDCl$_3$, 400 MHz): δ=1.34 (s, 3H), 1.35 (s, 3H), 7.03 (d, 1H, J=8Hz), 7.2-7.3 (m, 2H), 7.40-7.45 (m, 2H), 7.49 (t, 1H, J=7Hz), 7.68 (t, 1H, J=8Hz), 7.72 (d, 1H, J=9Hz), 7.91 (t, 2H, J=8Hz), 8.02 (d, 1H, J=7Hz), 8.35 (d, 1H, J=9Hz).

EXAMPLE 5 t-Butyl (E)-3-[[1-(4-cyanophenyl)naphthalen-2-yl]oxy]acrylate

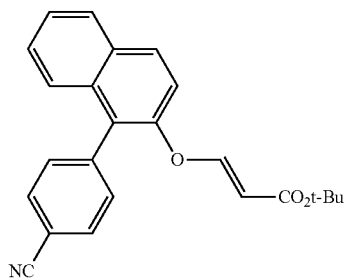 [SMILES: CC(C)(C)OC(=O)/C=C/Oc1ccc2ccccc2c1-c1ccc(C#N)cc1]

t-Butyl (Z)-3-[[1-(4-cyanophenyl)naphthalen-2-yl]oxy]acrylate

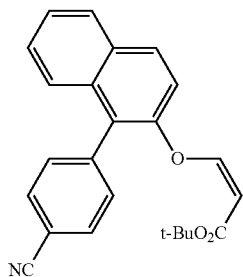

4-(2-Hydroxynaphthalen-1-yl)benzonitrile (83 mg, 0.34 mmol) was dissolved in dimethylformamide (4 mL), potassium carbonate (94 mg, 0.68 mmol) and t-butyl propiolate (70 μL, 0.51 mmol) were added thereto, and the solution was stirred at 120° C. After 5 hours, the reaction solution was allowed to be cooled to room temperature, diluted with ethyl acetate, and washed with water and brine. The organic layer was dried over sodium sulfate and filtered, and then the solvent was distilled off under reduced pressure. The obtained residue was purified by silica gel column chromatography (ethyl acetate:hexane=1:2) to obtain t-butyl (E)-3-[[1-(4-cyanophenyl)naphthalen-2-yl]oxy]acrylate (colorless oil material, 32 mg, yield of 25%) and t-butyl (Z)-3-[[1-(4-cyanophenyl)naphthalen-2-yl]oxy]acrylate (colorless oil material, 28 mg, yield of 22%).

$^1$H NMR (t-butyl (E)-3-[[1-(4-cyanophenyl)naphthalen-2-yl]oxy]acrylate, CDCl$_3$, 400 MHz): δ=1.45 (s, 9H), 5.20 (d, 1H, J=12Hz), 7.34 (d, 1H, J=9Hz), 7.4-7.5 (m, 5H), 7.57 (d, 1H, J=12Hz), 7.80 (d, 2H, J=8Hz), 7.92 (d, 1H, J=8Hz), 7.97 (d, 1H, J=9Hz).

$^1$H NMR (t-butyl (Z)-3-[[1-(4-cyanophenyl)naphthalen-2-yl]oxy]acrylate, CDCl$_3$, 400 MHz): δ=1.40 (s, 9H), 4.90 (d, 1H, J=7Hz), 6.60 (d, 1H, J=7Hz), 7.38 (d, 1H, J=9Hz), 7.4-7.6 (m, 5H), 7.79 (d, 2H, J=8Hz), 7.91 (d, 1H, J=8Hz), 7.95 (d, 1H, J=9Hz).

EXAMPLE 6

(E)-3-[[1-(4-Cyanophenyl)naphthalen-2-yl]oxy]acrylic acid

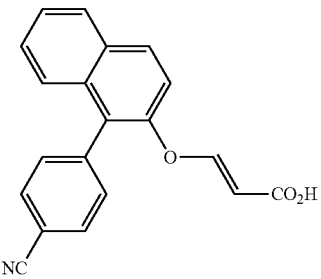 [SMILES: N#Cc1ccc(-c2c(O/C=C/C(=O)O)ccc3ccccc23)cc1]

t-Butyl (E)-3-[[1-(4-cyanophenyl)naphthalen-2-yl]oxy]acrylate (32 mg, 0.086 mmol) obtained in Example 5 was dissolved in dichloromethane (2 mL), trifluoroacetic acid (2 mL) was added thereto, and the solution was stirred at room temperature. After 4 hours, the solution was adjusted to pH 6 using 2 M sodium hydroxide aqueous solution in an ice bath and then the solvent was distilled off under reduced pressure. The obtained residue was purified by silica gel column chromatography (chloroform:methanol=5:1) to obtain a title compound (brown powder, 8 mg, yield of 67%).

$^1$H NMR (CD$_3$OD, 400 MHz): δ=5.17 (d, 1H, J=12Hz), 7.43 (d, 1H, J=9Hz), 7.5-7.6 (m, 5H), 7.69 (d, 1H, J=12Hz), 7.8-7.9 (m, 2H), 7.98 (d, 1H, J=8Hz), 8.06 (d, 1H, J=9Hz).

EXAMPLE 7

(Z)-3-[[1-(4-Cyanophenyl)naphthalen-2-yl]oxy]acrylic acid

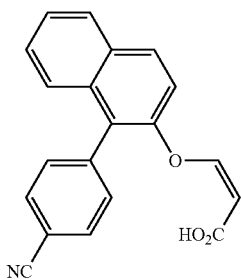 [SMILES: N#Cc1ccc(-c2c(O/C=C\C(=O)O)ccc3ccccc23)cc1]

A title compound (pale brown powder, 10 mg, yield of 42%) was obtained according to the same method as in Example 6 using t-butyl (Z)-3-[[1-(4-cyanophenyl)naphthalen-2-yl]oxy]acrylate (28 mg, 0.075 mmol) obtained in Example 5.

$^1$H NMR (CD$_3$OD, 400 MHz): δ=4.95 (d, 1H, J=7Hz), 6.95 (d, 1H, J=7Hz), 7.4-7.5 (m, 4H), 7.5-7.6 (m, 2H), 7.8-7.9 (m, 2H), 7.94 (dd, 1H, J=2Hz, 7Hz), 8.03 (d, 1H, J=9Hz).

EXAMPLE 8

2-Methyl-2-[[1-(pyridin-3-yl)naphthalen-2-yl]oxy]propanoic acid

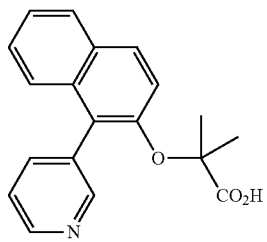 [SMILES: CC(C)(Oc1ccc2ccccc2c1-c1cccnc1)C(=O)O]

(1) 1-(Pyridin-3-yl)naphthalen-2-ol

A title compound (423 mg, yield of 100%) was obtained according to the same method as in Example 1 (2) using 3-(2-methoxynaphthalen-1-yl)pyridine (450 mg, 1.91 mmol) as a starting material.

$^1$H NMR (DMSO-$d_6$, 400 MHz): δ=7.3-7.4 (m, 4H), 7.90 (d, 1H, J=9Hz), 7.92 (d, 1H, J=9Hz), 7.99 (dd, 1H, J=5Hz, 8Hz), 8.36 (d, 1H, J=8Hz), 8.84 (d, 1H, J=5Hz), 8.87 (s, 1H), 10.06 (br s, 1H).

(2) 2-Methyl-2-[[1-(pyridin-3-yl)naphthalen-2-yl]oxy]propanoic acid

A title compound (white powder, 8 mg, yield of 41%) was obtained according to the same method as in Examples 1 (3) and 2 using 1-(pyridin-3-yl)naphthalen-2-ol (50 mg, 0.23 mmol) obtained in the above-described example.

$^1$H NMR (CD$_3$OD, 400 MHz): δ=1.37 (s, 3H), 1.38 (s, 3H), 7.3-7.4 (m, 4H), 7.60 (dd, 1H, J=5Hz, 8Hz), 7.8-7.9 (m, 3H), 8.5-8.6 (m, 2H).

EXAMPLE 9

Methyl (E)-3-[[1-(pyridin-3-yl)naphthalen-2-yl]oxy]acrylate

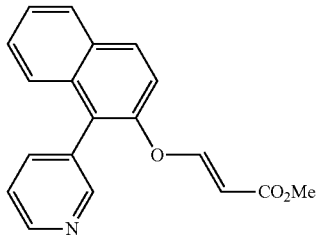 [SMILES: COC(=O)/C=C/Oc1ccc2ccccc2c1-c1cccnc1]

1-(Pyridin-3-yl)naphthalen-2-ol (80 mg, 0.26 mmol) obtained in Example 8 (1) was dissolved in dimethylformamide (2 mL), sodium hydride (16 mg, 0.4 mmol) was added thereto in an ice bath, and the solution was stirred at room temperature. After 10 minutes, methyl propiolate (91 μL, 1.1 mmol) was added to the reaction solution and the reaction solution was further stirred at 110° C. After 16 hours, water was added to the reaction solution in an ice bath, extraction was carried out using chloroform, the organic layer was dried over sodium sulfate and filtered, and then the solvent was distilled off under reduced pressure. The obtained residue was purified by silica gel column chromatography (ethyl acetate:hexane=1:2) to obtain a crude material of methyl (E)-3-[[1-(pyridin-3-yl)naphthalen-2-yl]oxy]acrylate (25 mg, yield of 22%) and methyl (Z)-3-[[1-(pyridin-3-yl)naphthalen-2-yl]oxy]acrylate.

$^1$H NMR (methyl (E)-3-[[1-(pyridin-3-yl)naphthalen-2-yl]oxy]acrylate, CDCl$_3$, 400 MHz): δ=3.65 (s, 3H), 5.25 (d, 1H, J=12Hz), 7.32 (d, 1H, J=9Hz), 7.4-7.5 (m, 4H), 7.6-7.7 (m, 2H), 7.90 (d, 1H, J=7Hz), 7.95 (d, 1H, J=9Hz), 8.60 (dd, 1H, J=1Hz, 2Hz), 8.68 (dd, 1H, J=2Hz, 5Hz).

EXAMPLE 10

(E)-3-[[1-(Pyridin-3-yl)naphthalen-2-yl]oxy]acrylic acid

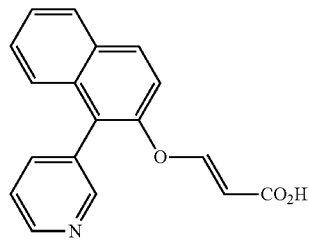 [SMILES: O=C(O)/C=C/Oc1ccc2ccccc2c1-c1cccnc1]

A title compound (white powder, 11 mg, yield of 73%) was obtained according to the same method as in Example 2 using methyl (E)-3-[[1-(pyridin-3-yl)naphthalen-2-yl]oxy]acrylate (16 mg, 0.05 mmol) obtained in Example 9.

$^1$H NMR (CDCl$_3$, 400 MHz): δ=5.22 (d, 1H, J=12Hz), 7.33 (d, 1H, J=9Hz), 7.4-7.5 (m, 4H), 7.7-7.8 (m, 2H), 7.91 (d, 1H, J=9Hz), 7.96 (d, 1H, J=9Hz), 8.61 (s, 1H), 8.69 (d, 1H, J=5Hz).

EXAMPLE 11

(Z)-3-[[1-(Pyridin-3-yl)naphthalen-2-yl]oxy]acrylic acid

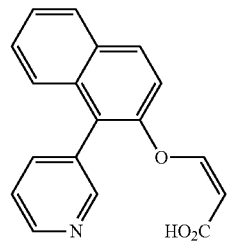 [SMILES: O=C(O)/C=C\Oc1ccc2ccccc2c1-c1cccnc1]

A title compound (white powder, 2.6 mg, yield of 84%) was obtained according to the same method as in Example 2 using the crude material of methyl (Z)-3-[[1-(pyridin-3-yl)naphthalen-2-yl]oxy]acrylate obtained in Example 9.

$^1$H NMR (CDCl$_3$, 400 MHz): δ=5.04 (d, 1H, J=7Hz), 6.81 (d, 1H, J=7Hz), 7.39 (d, 1H, J=9Hz), 7.4-7.5 (m, 3H), 7.59 (d, 1H, J=9Hz), 7.81 (d, 1H, J=8Hz), 7.91 (d, 1H, J=9Hz), 7.97 (d, 1H, J=9Hz), 8.73 (d, 1H, J=4Hz), 8.78 (s, 1H).

EXAMPLE 12

Ethyl 2-[[5-(4-cyanophenyl)quinolin-6-yl]oxy]-2-methyl propanoate

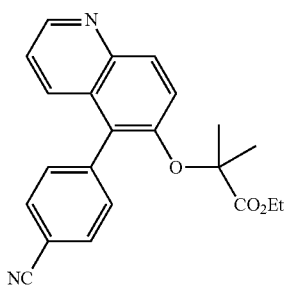 [SMILES: CCOC(=O)C(C)(C)Oc1ccc2ncccc2c1-c1ccc(C#N)cc1]

(1) 4-(6-Methoxyquinolin-5-yl)benzonitrile

A title compound (pale brown crystal, 160 mg, yield of 48%) was obtained according to the same method as in Example 1 (1) using 5-bromo-6-methoxyquinoline (300 mg, 1.26 mmol) and (4-cyanophenyl)boronic acid.

$^1$H NMR (CDCl$_3$, 400 MHz): δ=3.89 (s, 3H), 7.29 (dd, 1H, J=4Hz, 9Hz), 7.49 (d, 2H, J=9Hz), 7.60 (d, 1H, J=9Hz), 7.7-7.8 (m, 1H), 7.80 (d, 2H, J=8Hz), 8.21 (d, 1H, J=9Hz), 8.81 (dd, 1H, J=1Hz, 4Hz).

(2) Ethyl 2-[[5-(4-cyanophenyl)quinolin-6-yl]oxy]-2-methylpropanoate 4-(6-Methoxyquinolin-5-yl)benzonitrile (160 mg, 0.61 mmol) obtained in the above-described example was dissolved in dimethylformamide (6 mL), lithium bromide (1.06 g, 12.2 mmol) and p-toluenesulfonic acid monohydrate (116 mg, 0.61 mmol) were added thereto, and the solution was stirred at 180° C. in a nitrogen atmosphere. After 2 hours, the reaction solution was allowed to be cooled at room temperature and adjusted to 10 pH 8 by a saturated sodium hydrogen carbonate aqueous solution, and extraction was carried out using chloroform. The organic layer was dried over sodium sulfate and filtered, and then the solvent was distilled off under reduced pressure. Next, toluene (10 mL) was added to the obtained residue and dimethylformamide was distilled off by azeotrope to obtain a crude material of 4-(6-hydroxyquinolin-5-yl)benzonitrile.

A title compound (23 mg, yield of 75%) was obtained according to the same method as in Example 1 (3) using a part of the crude material of 4-(6-hydroxyquinolin-5-yl)benzonitrile (82 mg, 0.33 mmol) obtained in the above-described example.

$^1$H NMR (CDCl$_3$, 400 MHz): δ=1.27 (t, 3H, J=7Hz), 1.41 (s, 6H), 4.26 (q, 2H, J=7H), 7.31 (dd, 1H, J=4Hz, 9Hz), 7.41 (d, 1H, J=9Hz), 7.52 (d, 2H, J=9Hz), 7.7-7.9 (m, 3H), 8.80 (d, 1H, J=9Hz), 8.83 (dd, 1H, J=4Hz, 1Hz).

EXAMPLE 13

2-[[5-(4-Cyanophenyl)quinolin-6-yl]oxy]-2-methyl-propanoic acid

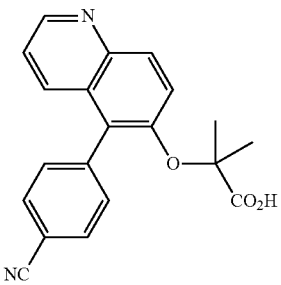

A title compound (light yellow crystal, 6 mg, yield of 22%) was obtained according to the same method as in Example 2 using ethyl 2-[[5-(4-cyanophenyl)quinolin-6-yl]oxy]-2-methyl propanoate (30 mg, 0.08 mmol) obtained in Example 12.

$^1$H NMR (CDCl$_3$, 400 MHz): δ=1.38 (s, 6H), 7.3-7.4 (m, 1H), 7.51 (d, 2H, J=8Hz), 7.60 (d, 1H, J=9Hz), 7.7-7.9 (m, 3H), 8.00 (d, 1H, J=9Hz), 8.74 (dd, 1H, J=1Hz, 4Hz).

EXAMPLE 14

Ethyl 2-[[5-(4-cyanophenyl)quinolin-6-yl]thio]-2-methylpropanoate

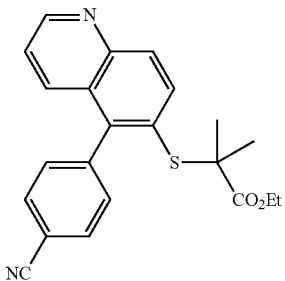 [SMILES: CCOC(=O)C(C)(C)Sc1ccc2ncccc2c1-c1ccc(C#N)cc1]

(1) Dimethylcarbamothioic acid O-[5-(4-cyanophenyl)quinolin-6-yl]

A title compound (yellow crystal, 23 mg, yield of 21%) was obtained according to the same method as in Example 3 (1) using the crude material of 4-(6-hydroxyquinolin-5-yl)benzonitrile (82 mg) obtained in Example 12 (2) as a starting material.

$^1$H NMR (CDCl$_3$, 400 MHz): δ=3.04 (s, 3H), 3.34 (s, 3H), 7.36 (dd, 1H, J=5Hz, 9Hz), 7.5-7.6 (m, 3H), 7.7-7.8 (m, 3H), 8.20 (d, 1H, J=9Hz), 8.93 (dd, 1H, J=2Hz, 4Hz).

(2) Dimethylcarbamothioic acid S-[5-(4-cyanophenyl)quinolin-6-yl]

A title compound (yellow amorphous, 4.5 mg, yield of 20%) was obtained according to the same method as in Example 3 (2) using dimethylcarbamothioic acid O-[5-(4- cyanophenyl)quinolin-6-yl] (23 mg, 0.07 mmol) obtained in the above-described example.

$^1$H NMR (CDCl$_3$, 400 MHz): δ=2.96 (s, 6H), 7.34 (dd, 1H, J=4Hz, 9Hz), 7.44 (d, 2H, J=8Hz), 7.6-7.7 (m, 1H), 7.79 (d, 2H, J=8Hz), 7.90 (d, 1H, J=9Hz), 8.18 (d, 1H, J=9Hz), 8.95 (dd, 1H, J=2Hz, 4Hz).

(3) Ethyl 2-[[5-(4-cyanophenyl)quinolin-6-yl]thio]-2-methylpropanoate

A title compound (light yellow amorphous, 4.5 mg, yield of 85%) was obtained according to the same method as in Examples 3 (3) and 1 (3) using dimethylcarbamothioic acid S-[5-(4-cyanophenyl)quinolin-6-yl] (4.5 mg, 0.01 mmol) obtained in the above-described example.

$^1$H NMR (CDCl$_3$, 400 MHz): δ=1.2-1.4 (m, 3H), 1.38 (s, 6H), 4.0-4.2 (m, 2H), 7.34 (dd, 1H, J=4Hz, 9Hz), 7.39 (d, 2H, J=8Hz), 7.65 (d, 1H, J=9Hz), 7.80 (d, 2H, J=8Hz), 7.84 (d, 1H, J=9Hz), 8.10 (d, 1H, J=8Hz), 8.93 (dd, 1H, J=2Hz, 4Hz).

EXAMPLE 15

2-[[5-(4-Cyanophenyl)quinolin-6-yl]thio]-2-methylpropanoic acid

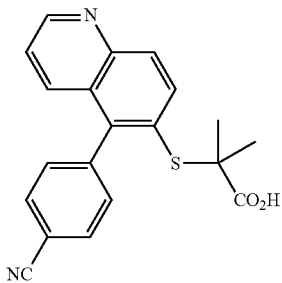 [SMILES: CC(C)(Sc1ccc2ncccc2c1-c1ccc(C#N)cc1)C(=O)O]

A title compound (light yellow powder, 2.8 mg, yield of 67%) was obtained according to the same method as in Example 2 using ethyl 2-[[5-(4-cyanophenyl)quinolin-6-yl]thio]-2-methylpropanoate (4.5 mg, 0.012 mmol) obtained in Example 14.

$^1$H NMR (CDCl$_3$, 400 MHz): δ=1.25 (s, 6H), 7.3-7.5 (m, 3H), 7.75 (d, 1H, J=8Hz), 7.82 (d, 2H, J=8Hz), 7.98 (d, 1H, J=9Hz), 8.00 (d, 1H, J=9Hz), 8.9-9.0 (m, 1H).

EXAMPLE 16

Ethyl 2-[[7-(4-cyanophenyl)benzo[d]oxazol-6-yl]oxy]-2-methylpropanoate

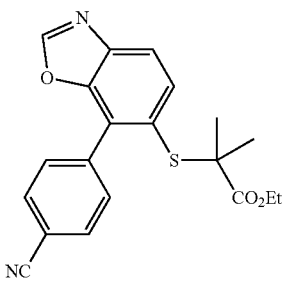 [SMILES: CCOC(=O)C(C)(C)Sc1ccc2ncoc2c1-c1ccc(C#N)cc1]

(1) 2-Iodo-3-methoxy-6-nitrophenol

2-Iodobenzene-1,3-diol (1 g, 4.24 mmol) was dissolved in acetic acid (10 mL) and fuming nitric acid (210 μL, 5.08 mmol) was added dropwise thereto in a water bath. After 5 minutes, ice was added to the reaction solution and extraction was carried out using chloroform. The organic layer was dried over sodium sulfate and filtered, and then the solvent was distilled off under reduced pressure.

The obtained residue was dissolved in dimethylformamide (15 mL), potassium carbonate (1.89 g, 13.7 mmol) and methyl iodide (1.69 mL, 27.4 mmol) were added thereto, and the solution was stirred at room temperature. After 18 hours, 1 M hydrochloric acid (1 mL) was added to the reaction solution to adjust to pH 5 and then the reaction solution was diluted with ethyl acetate. The organic layer was washed with water and brine, dried over sodium sulfate, and filtered, and then the solvent was distilled off under reduced pressure. The obtained residue was purified by silica gel column chromatography (ethyl acetate:hexane=1:4) to obtain a title compound (180 mg, yield of 22%).

$^1$H NMR (CDCl$_3$, 400 MHz): δ=4.03 (s, 3H), 6.56 (d, 1H, J=9Hz), 8.21 (d, 1H, J=9Hz), 11.73 (s, 1H).

(2) 2'-Hydroxy-6'-methoxy-3'-nitro-[1,1'-biphenyl]-4-carbonitrile

2-Iodo-3-methoxy-6-nitrophenol (180 mg, 0.61 mmol) obtained in the above-described example, 4-cyanophenylboronic acid (108 mg, 0.73 mmol), tetrakis(triphenylphosphine)palladium (21 mg, 0.018 mmol), tris(dibenzylideneacetone)dipalladium (4 mg, 6 mmol), triphenyl phosphine (21 mg, 0.08 mmol), and potassium carbonate (169 mg, 1.22 mmol) were dissolved in toluene (6 mL), ethanol (3 mL), and water (1.5 mL), and the solution was stirred at 80° C. in a nitrogen atmosphere. After 16 hours, the reaction solution was allowed to be cooled to room temperature, 1 M hydrochloric acid was added thereto to adjust to pH 5, and the reaction solution was diluted with ethyl acetate and washed with water and brine. The organic layer was dried over sodium sulfate and filtered, and then the solvent was distilled off under reduced pressure. The obtained residue was purified by silica gel column chromatography (ethyl acetate:hexane=1:4) to obtain a title compound (110 mg, yield of 76%).

$^1$H NMR (CDCl$_3$, 400 MHz): δ=3.89 (s, 3H), 6.71 (d, 1H, J=9Hz), 7.49 (d, 2H, J=8Hz), 7.74 (d, 2H, J=8Hz), 8.25 (d, 1H, J=9Hz), 11.19 (s, 1H).

(3) 4-(6-Methoxybenzo[d]oxazol-7-yl)benzonitrile

2'-Hydroxy-6'-methoxy-3'-nitro-[1,1'-biphenyl]-4-carbonitrile (50 mg, 0.19 mmol) obtained in the above-described example was dissolved in methanol (2 mL) and tetrahydrofuran (2 mL), 10% palladium carbon (10 mg) was added thereto in a nitrogen atmosphere, and the resulting solution was subjected to catalytic hydrogenation at room temperature for 2 hours. The reaction solution was filtered through a celite pad and the solvent of the filtrate was distilled off under reduced pressure.

The obtained residue was dissolved in triethyl orthoformate (2 mL) and the solution was stirred at 150° C. for 16 hours in a nitrogen atmosphere. The reaction solution was allowed to be cooled to room temperature, toluene (10 mL) was added thereto, and the solvent was distilled off by azeotrope under reduced pressure. The obtained residue was purified by silica gel column chromatography (ethyl acetate:hexane=1:2) to obtain a title compound (20 mg, yield of 42%).

$^1$H NMR (CDCl$_3$, 400 MHz): δ=3.91 (s, 3H), 7.13 (d, 1H, J=9Hz), 7.7-8.0 (m, 5H), 8.03 (s, 1H).

(4) Ethyl 2-[[7-(4-cyanophenyl)benzo[d]oxazol-6-yl]oxy]-2-methylpropanoate

A crude material of 4-(6-methoxybenzo[d]oxazol-7-yl)benzonitrile was obtained according to the same method as in Example 12 (2) using 4-(6-methoxybenzo[d]oxazol-7-yl)benzonitrile (20 mg, 0.08 mmol) obtained in the above-described example. A title compound (colorless oil material, 11 mg, 0.03 mmol, yield of 39%) was obtained according to the same method as in Example 1 (3) using the obtained crude material.

$^1$H NMR (CDCl$_3$, 400 MHz): δ=1.27 (t, 3H, J=7Hz), 1.45 (s, 6H), 4.25 (q, 2H, J=7Hz), 7.03 (d, 1H, J=9Hz), 7.68 (d, 1H, J=9Hz), 7.78 (d, 2H, J=9Hz), 7.86 (d, 2H, J=9Hz), 8.06 (s, 1H).

EXAMPLE 17

2-[[7-(4-Cyanophenyl)benzo[d]oxazol-6-yl]oxy]-2-methylpropanoic acid

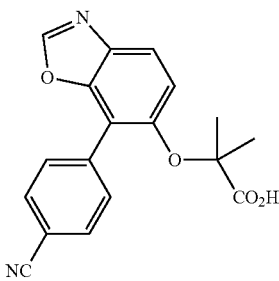 [SMILES: CC(C)(Oc1ccc2ncoc2c1-c1ccc(C#N)cc1)C(=O)O]

A title compound (white crystal, 2.9 mg, yield of 29%) was obtained according to the same method as in Example 2 using ethyl 2-[[7-(4-cyanophenyl)benzo[d]oxazol-6-yl]oxy]-2-methylpropanoate (11 mg, 0.03 mmol) obtained in Example 16.

$^1$H NMR (CD$_3$OD, 400 MHz): δ=1.44 (s, 6H), 7.17 (d, 1H, J=9Hz), 7.67 (d, 1H, J=9Hz), 7.84 (d, 2H, J=9Hz), 7.90 (d, 2H, J=9Hz), 8.42 (s, 1H).

EXAMPLE 18

Ethyl 2-[[7-(4-cyanophenyl)benzo[d]thiazol-6-yl]oxy]-2-methyl propanoate

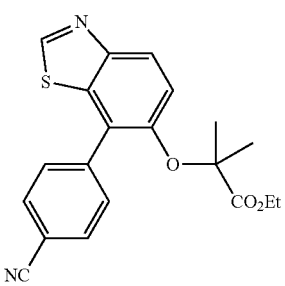 [SMILES: CCOC(=O)C(C)(C)Oc1ccc2ncsc2c1-c1ccc(C#N)cc1]

(1) 4-(6-Methoxybenzo[d]thiazol-7-yl)benzonitrile

A title compound (off-white crystal, 761 mg, yield of 70%) was obtained according to the same method as in Example 16 (2) using 7-bromo-6-methoxybenzo[d]thiazole (1.0 g, 4.1 mmol) and 4-cyanophenylboronic acid.

$^1$H NMR (CDCl$_3$, 400 MHz): δ=3.87 (s, 3H), 7.24-7.28 (m, 1H), 7.68 (d, 2H, J=8Hz), 7.77 (d, 2H, J=9Hz), 8.11 (d, 1H, J=9Hz), 8.82 (s, 1H).

(2) 4-(6-Hydroxybenzo[d]thiazol-7-yl)benzonitrile 4-(6-Methoxybenzo[d]thiazol-7-yl)benzonitrile (870 mg, 3.27 mmol) obtained in the above-described example and pyridine hydrochloride (9 g) were mixed with each other and stirred at 200° C. for 3 hours. The reaction solution was allowed to be cooled to room temperature, and a saturated sodium hydrogen carbonate aqueous solution was added thereto to adjust to pH 8. The precipitated crystals were separated by filtration and dried under reduced pressure to obtain a title compound (830 mg, 100%).

$^1$H NMR (CD$_3$OD, 400 MHz): δ=7.20 (d, 1H, J=9Hz), 7.79 (d, 2H, J=8Hz), 7.85 (d, 2H, J=8Hz), 7.90 (d, 1H, J=9Hz), 8.98 (s, 1H).

(3) Ethyl 2-[[7-(4-cyanophenyl)benzo[d]thiazol-6-yl]oxy]-2-methylpropanoate

A title compound (colorless oil material, 36 mg, yield of 67%) was obtained according to the same method as in Example 1 (3) using 4-(6-hydroxybenzo[d]thiazol-7-yl)benzonitrile (38 mg, 0.15 mmol) obtained in the above-described example.

$^1$H NMR (CDCl$_3$, 400 MHz): δ=1.27 (t, 3H, J=7Hz), 1.43 (s, 6H), 4.25 (q, 2H, J=7Hz), 7.17 (d, 1H, J=9Hz), 7.74 (d, 2H, J=8Hz), 7.78 (d, 2H, J=8Hz), 8.02 (d, 1H, J=9Hz), 8.88 (s, 1H).

EXAMPLE 19

2-[[7-(4-Cyanophenyl)benzo[d]thiazol-6-yl]oxy]-2-methylpropanoic acid

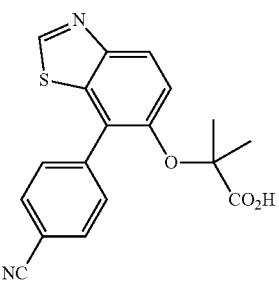 [SMILES: CC(C)(Oc1ccc2ncsc2c1-c1ccc(C#N)cc1)C(=O)O]

A title compound (white crystal, 22 mg, yield of 65%) was obtained according to the same method as in Example 2 using ethyl 2-[[7-(4-cyanophenyl)benzo[d]thiazol-6-yl]oxy]-2-methylpropanoate (36 mg, 0.1 mmol) obtained in Example 18.

$^1$H NMR (CDCl$_3$, 400 MHz): δ=1.46 (s, 6H), 7.29 (d, 1H, J=9Hz), 7.72 (d, 2H, J=8Hz), 7.80 (d, 2H, J=8Hz), 8.05 (d, 1H, J=9Hz), 8.93 (s, 1H).

EXAMPLE 20 t-Butyl (E)-3-[[7-(4-cyanophenyl)benzo[d]thiazol-6-yl]oxy]acrylate

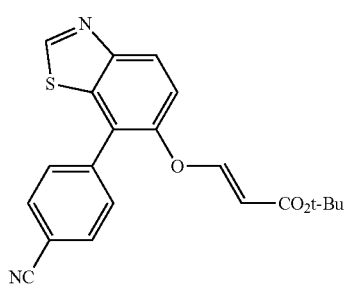 [SMILES: CC(C)(C)OC(=O)/C=C/Oc1ccc2ncsc2c1-c1ccc(C#N)cc1]

4-(6-Hydroxybenzo[d]thiazol-7-yl)benzonitrile (50 mg, 0.98 mmol) obtained in Example 18 (2) was dissolved in dichloromethane (2 mL), 1,4-diazabicyclo[2.2.2]octane (2.2 mg, 0.02 mmol) and t-butyl propionate (33 μL, 0.24 mmol) were added thereto, and the solution was stirred at room temperature. After 2 hours, water was added to the reaction solution and extraction was carried out using ethyl acetate. The organic layer was washed with water and brine, dried over sodium sulfate, and filtered, and then the solvent was distilled off under reduced pressure. The obtained residue was purified by silica gel column chromatography (hexane:ethyl acetate=2:1) to obtain a title compound (69 mg, yield of 92%).

$^1$H NMR (CDCl$_3$, 400 MHz): δ=1.46 (s, 9H), 5.31 (d, 1H, J=12Hz), 7.39 (d, 1H, J=9Hz), 7.58 (d, 1H, J=12Hz), 7.66 (dd, 2H, J=2Hz, 8Hz), 7.80 (dd, 2H, J=2Hz, 8Hz), 8.18 (d, 1H, J=9Hz), 9.00 (s, 1H).

EXAMPLE 21

(E)-3-[[7-(4-cyanophenyl)benzo[d]thiazol-6-yl]oxy]acrylic acid

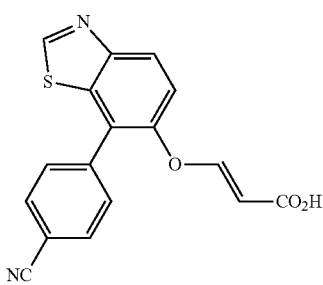 [SMILES: N#Cc1ccc(-c2c(O/C=C/C(=O)O)ccc3ncsc23)cc1]

A title compound (33 mg, yield of 58%) was obtained according to the same method as in Example 6 using t-butyl (E)-3-[[7-(4-cyanophenyl)benzo[d]thiazol-6-yl]oxy]acrylate (67 mg, 0.18 mmol) obtained in Example 20.

$^1$H NMR (CD$_3$OD, 400 MHz): δ=5.36 (d, 1H, J=12Hz), 7.52 (d, 11, J=9Hz), 7.55 (d, 1H, J=12Hz), 7.76 (dt, 2H, J=2Hz, 9Hz), 7.89 (dt, 2H, J=2Hz, 9Hz), 8.16 (d, 1H, J=9Hz), 9.22 (s, 1H).

EXAMPLE 22

Ethyl 2-[[7-(4-cyanophenyl)benzo[d]thiazol-6-yl]thio]-2-methylpropanoate

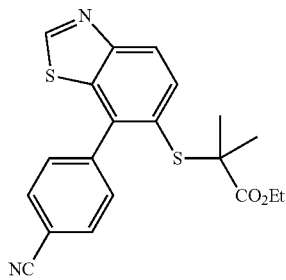

(1) Dimethylcarbamothioic acid O-[7-(4-cyanophenyl)benzo[d]thiazol-6-yl]

4-(6-Hydroxybenzo[d]thiazol-7-yl)benzonitrile (800 mg, 3.17 mmol) obtained in Example 18 (2), triethylamine (1.1 mL, 7.93 mmol), and dimethylaminopyridine (97 mg, 0.79 mmol) were dissolved in 1,2-dimethoxyethane (20 mL), dimethylthiocarbamoyl chloride (802 mg, 6.34 mmol) was added thereto, and the solution was stirred at 80° C. in a nitrogen atmosphere. After 15 hours, the reaction solution was allowed to be cooled to room temperature, water was added thereto, and extraction was carried out using ethyl acetate. The organic layer was washed with water and brine, dried over sodium sulfate, and filtered, and then the solvent was distilled off under reduced pressure. The obtained residue was purified by silica gel column chromatography (chloroform:methanol=20:1) to obtain a title compound (641 mg, yield of 60%).

$^1$H NMR (CDCl$_3$, 400 MHz): δ=3.12 (s, 3H), 3.33 (s, 3H), 7.36 (d, 1H, J=9Hz), 7.69 (d, 2H, J=9Hz), 7.76 (d, 2H, J=9Hz), 8.16 (s, 1H), 8.98 (s, 1H).

(2) Dimethylcarbamothioic acid S-[7-(4-cyanophenyl)benzo[d]thiazol-6-yl]

A title compound (yellow crystal, 420 mg, yield of 66%) was obtained according to the same method as in Example 3 (2) using dimethylcarbamothioic acid O-[7-(4-cyanophenyl)benzo[d]thiazol-6-yl] (640 mg, 1.89 mmol) obtained in the above-described example.

$^1$H NMR (CDCl$_3$, 400 MHz): δ=2.94 (s, 6H), 7.55 (d, 2H, J=8Hz), 7.7-7.8 (m, 3H), 8.15 (d, 1H, J=9Hz), 9.02 (s, 1H).

(3) 4-(6-Mercaptobenzo[d]thiazol-7-yl)benzonitrile

Dimethylcarbamothioic acid S-[7-(4-cyanophenyl)benzo[d]thiazol-6-yl] (100 mg, 0.30 mmol) obtained in the above-described example was dissolved in ethanol (3 mL), 20% sodium ethoxide-ethanol solution (167 μL, 0.38 mmol) was added thereto, and the solution was stirred at 40° C. for 21 hours in a nitrogen atmosphere. 3 M hydrochloric acid was added to the reaction solution to adjust to pH 6, extraction was carried out using ethyl acetate, and the organic layer was washed with brine. The organic layer was dried over sodium sulfate and filtered, and then the solvent was distilled off under reduced pressure. The obtained residue was purified by silica gel column chromatography (chloroform:methanol=1:20) to obtain a title compound (71 mg, yield of 90%).

$^1$H NMR (CDCl$_3$, 400 MHz): δ=7.54 (d, 1H, J=8Hz), 7.60 (d, 2H, J=8Hz), 7.84 (d, 2H, J=9Hz), 8.00 (d, 11H, J=9Hz), 8.88 (s, 1H).

(4) Ethyl 2-[[7-(4-cyanophenyl)benzo[d]thiazol-6-yl]thio]-2-methylpropanoate

A title compound (colorless oil material, 43 mg, yield of 85%) was obtained according to the same method as in Example 1 (3) using 4-(6-mercaptobenzo[d]thiazol-7-yl)benzonitrile (36 mg, 0.13 mmol) obtained in the above-described example.

$^1$H NMR (CDCl$_3$, 400 MHz): δ=1.19 (t, 3H, J=7Hz), 1.31 (s, 6H), 4.02 (q, 2H, J=7Hz), 7.57 (d, 2H, J=9Hz), 7.76 (d, 1H, J=9Hz), 7.80 (d, 2H, J=9H), 8.10 (d, 1H, J=9Hz), 9.04 (s, 1H).

EXAMPLE 23 t-Butyl 2-[[7-(4-cyanophenyl)benzo[d]thiazol-6-yl]thio]-2-methylpropanoate

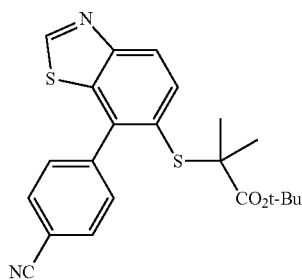 [SMILES: CC(C)(C)OC(=O)C(C)(C)Sc1ccc2ncsc2c1-c1ccc(C#N)cc1]

A title compound (pale yellow oil material, 94 mg, yield of 60%) was obtained according to the same method as in Example 1 (3) using 4-(6-mercaptobenzo[d]thiazol-7-yl)benzonitrile (110 mg, 0.41 mmol) obtained in Example 22 (3) and t-butyl 2-bromoisobutyrate (152 μL, 0.82 mmol).

$^1$H NMR (CDCl$_3$, 400 MHz): δ=1.25 (s, 6H), 1.45 (s, 9H), 7.55 (d, 2H, J=8Hz), 7.80-7.82 (m, 3H), 8.09 (d, 1H, J=8Hz), 9.01 (s, 1H).

EXAMPLE 24

2-[[7-(4-Cyanophenyl)benzo[d]thiazol-6-yl]thio]-2-methylpropanoic acid

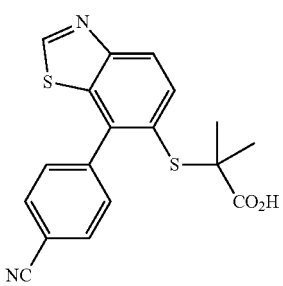 [SMILES: CC(C)(Sc1ccc2ncsc2c1-c1ccc(C#N)cc1)C(=O)O]

A title compound (light yellow crystal, 52 mg, yield of 64%) was obtained according to the same method as in Example 6 using t-butyl 2-[[7-(4-cyanophenyl)benzo[d]thiazol-6-yl]thio]-2-methylpropanoate (94 mg, 0.23 mmol) obtained in Example 24.

$^1$H NMR (CDCl$_3$, 400 MHz): δ=1.36 (s, 6H), 7.59 (d, 2H, J=8Hz), 7.78 (d, 2H, J=8Hz), 7.84 (d, 1H, J=8Hz), 8.08 (d, 1H, J=8Hz), 9.08 (s, 1H).

EXAMPLE 25

Ethyl 2-[[7-(4-cyanophenyl)benzo[d]isothiazol-6-yl]oxy]-2-methylpropanoate

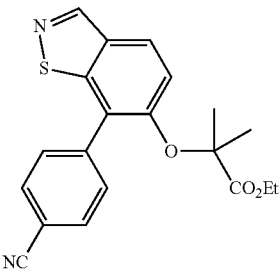 [SMILES: CCOC(=O)C(C)(C)Oc1ccc2cnsc2c1-c1ccc(C#N)cc1]

(1) 7-Bromobenzo[d]isothiazol-6-ol

Benzo[d]isothiazol-6-ol (410 g, 2.7 mmol) was dissolved in acetic acid (8 mL), bromine (0.14 mL, 2.7 mmol) was added thereto, and the solution was stirred at room temperature. After 2 hours, ice water was added to the reaction solution and extraction was carried out using ethyl acetate. The organic layer was washed with a saturated sodium hydrogen carbonate aqueous solution, a 10% sodium thiosulfate aqueous solution, and brine, dried over sodium sulfate, and filtered, and then the solvent was distilled off under reduced pressure. The obtained residue was washed to obtain a title compound (540 mg, yield of 87%).

$^1$H NMR (DMSO-d$_6$, 400 MHz): δ=5.94 (s, 1H), 7.15 (d, 1H, J=9Hz), 7.90 (d, 1H, J=9Hz), 8.87 (s, 1H).

(2) 4-(6-Hydroxybenzo[d]isothiazol-7-yl)benzonitrile

A title compound (brown crystal, 280 mg, yield of 34%) was obtained according to the same method as in Example 1 (1) using 7-bromobenzo[d]isothiazol-6-ol (750 mg, 3.26 mmol) obtained in the above-described example and (4-cyanophenyl)boronic acid.

$^1$H NMR (DMSO-d$_6$, 400 MHz): δ=5.64 (s, 1H), 7.14 (d, 1H, J=9Hz), 7.79 (d, 2H, J=8Hz), 7.86 (d, 2H, J=8Hz), 7.96 (d, 1H, J=9Hz), 8.84 (s, 1H).

(3) Ethyl 2-[[7-(4-cyanophenyl)benzo[d]isothiazol-6-yl]oxy]-2-methylpropanoate

A title compound (colorless oil material, 20 mg, yield of 28%) was obtained according to the same method as in Example 1 (3) using 4-(6-hydroxybenzo[d]isothiazol-7-yl)benzonitrile (20 mg, 0.08 mmol) obtained in the above-described example.

$^1$H NMR (CDCl$_3$, 400 MHz): δ=1.25 (t, 3H, J=7Hz), 1.51 (s, 6H), 4.25 (q, 2H, J=7Hz), 7.06 (d, 1H, J=9Hz), 7.7-7.8 (m, 4H), 7.94 (d, 1H, J=9Hz), 8.85 (s, 1H).

EXAMPLE 26

2-[[7-(4-Cyanophenyl)benzo[d]isothiazol-6-yl]oxy]-2-methylpropanoic acid

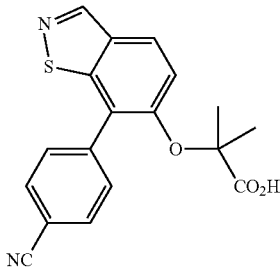 [SMILES: CC(C)(Oc1ccc2cnsc2c1-c1ccc(C#N)cc1)C(=O)O]

Ethyl 2-[[7-(4-cyanophenyl)benzo[d]isothiazol-6-yl]oxy]-2-methylpropanoate (8 mg, 0.022 mmol) obtained in Example 25 was dissolved in tetrahydrofuran (0.1 mL) and methanol (0.1 mL), and then water (0.1 mL) and lithium hydroxide monohydrate (1.9 mg, 0.045 mmol) were added thereto, and the solution was stirred at room temperature. After 18 hours, the reaction solution was acidified using 2 M hydrochloric acid aqueous solution, extraction was carried out using ethyl acetate, and the organic layer was washed with brine, dried over sodium sulfate, and filtered, and then the solvent was distilled off under reduced pressure. The obtained residue was purified by silica gel column chromatography (chloroform:methanol=20:1) to obtain a title compound (brown crystal, 7 mg, yield of 95%).

$^1$H NMR (DMSO-d$_6$, 400 MHz): δ=1.50 (s, 6H), 7.16 (d, 1H, J=9Hz), 7.84 (d, 2H, J=8Hz), 8.01 (d, 2H, J=8Hz), 8.20 (d, 1H, J=9Hz), 9.09 (s, 1H).

EXAMPLE 27

Ethyl 2-[[7-(4-cyanophenyl)benzo[d]isothiazol-6-yl]thio]-2-methylpropanoate

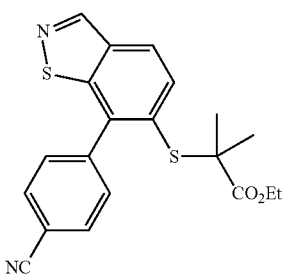

(1) Dimethylcarbamothioic acid O-[7-(4-cyanophenyl)benzo[d]isothiazol-6-yl]

A title compound (light yellow crystal, 190 mg, yield of 56%) was obtained according to the same method as in Example 22 (1) using 4-(6-hydroxybenzo[d]isothiazol-7-yl)benzonitrile (0.25 mg, 1.0 mmol) obtained in Example 25 (2).

$^1$H NMR (CDCl$_3$, 400 MHz): δ=3.17 (s, 3H), 3.37 (s, 3H), 7.33 (d, 1H, J=9Hz), 7.75 (d, 2H, J=8Hz), 7.79 (d, 2H, J=8Hz), 8.09 (d, 1H, J=9Hz), 8.95 (s, 1H).

(2) Dimethylcarbamothioic acid S-[7-(4-cyanophenyl)benzo[d]isothiazol-6-yl]

A title compound (pale yellow crystal, 150 mg, yield of 79%) was obtained at 250° C. according to the same method as in Example 3 (2) using dimethylcarbamothioic acid O-[7-(4-cyanophenyl)benzo[d]isothiazol-6-yl] (190 mg, 0.56 mmol) obtained in the above-described example.

$^1$H NMR (CDCl$_3$, 400 MHz): δ=2.98 (s, 6H), 7.60 (d, 2H, J=8Hz), 7.72 (d, 1H, J=8Hz), 7.79 (d, 2H, J=8Hz), 8.08 (d, 1H, J=8Hz), 8.97 (s, 1H).

(3) 4-(6-Mercaptobenzo[d]isothiazol-7-yl)benzonitrile

A title compound (pale yellow oil material, 35 mg, yield of 30%) was obtained according to the same method as in Example 22 (3) using dimethylcarbamothioic acid S-[7-(4-cyanophenyl)benzo[d]isothiazol-6-yl] (146 mg, 0.43 mmol) obtained in in the above-described example.

$^1$H NMR (CDCl$_3$, 400 MHz): δ=3.52 (s, 1H), 7.45 (d, 1H, J=8Hz), 7.66 (d, 2H, J=8Hz), 7.86 (d, 2H, J=8Hz), 7.91 (d, 1H, J=8Hz), 8.87 (s, 1H).

(4) Ethyl 2-[[7-(4-cyanophenyl)benzo[d]isothiazol-6-yl]thio]-2-methylpropanoate

A title compound (colorless oil material, 33 mg, yield of 66%) was obtained according to the same method as in Example 1 (3) using 4-(6-mercaptobenzo[d]isothiazol-7-yl)benzonitrile (35 mg, 0.13 mmol) obtained in the above-described example.

$^1$H NMR (CDCl$_3$, 400 MHz): δ=1.20 (t, 3H, J=7Hz), 1.35 (s, 6H), 4.05 (q, 2H, J=7Hz), 7.61 (d, 2H, J=8Hz), 7.66 (d, 1H, J=8Hz), 7.81 (d, 2H, J=8Hz), 8.01 (d, 1H, J=8Hz), 8.95 (s, 1H).

EXAMPLE 28

2-[[7-(4-Cyanophenyl)benzo[d]isothiazol-6-yl]thio]-2-methylpropanoic acid

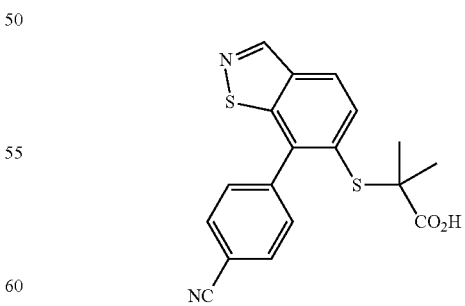

A title compound (white crystal, 20 mg, yield of 65%) was obtained according to the same method as in Example 26 using ethyl 2-[[7-(4-cyanophenyl)benzo[d]isothiazol-6-yl]thio]-2-methylpropanoate (33 mg, 0.09 mmol) obtained in Example 27.

¹H NMR (DMSO-d₄, 400 MHz): δ=1.29 (s, 6H), 7.67 (d, 2H, J=8Hz), 7.74 (d, 1H, J=8Hz), 8.01 (d, 2H, J=8Hz), 8.26 (d, 1H, J=8Hz), 9.23 (s, 1H).

EXAMPLE 29

Ethyl 2-[[4-(4-cyanophenyl)benzo[c][1,2,5]thiadiazol-5-yl]oxy]-2-methylpropanoate

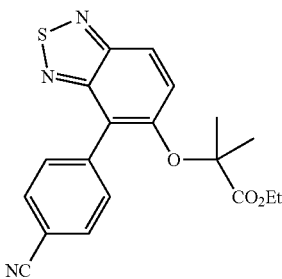 [SMILES: CCOC(=O)C(C)(C)Oc1ccc2nsnc2c1-c1ccc(C#N)cc1]

(1) 4-(5-Hydroxybenzo[c][1,2,5]thiadiazol-4-yl)benzonitrile

A title compound (yellow crystal, 110 mg, yield of 18%) was obtained according to the same method as in Example 1 (1) using benzo4-bromobenzo[c][1,2,5]thiadiazol-5-ol (560 mg, 2.42 mmol) and (4-cyanophenyl)boronic acid.
¹H NMR (CDCl₃, 400 MHz): δ=5.73 (s, 1H), 7.45 (d, 1H, J=10Hz), 7.81 (d, 2H, J=8Hz), 7.88 (d, 2H, J=8Hz), 7.96 (d, 1H, J=10Hz).

(2) Ethyl 2-[[4-(4-cyanophenyl)benzo[c][1,2,5]thiadiazol-5-yl]oxy]-2-methylpropanoate A title compound (colorless oil material, 24 mg, yield of 59%) was obtained according to the same method as in Example 1 (3) using 4-(5-hydroxybenzo[c][1,2,5]thiadiazol-4-yl)benzonitrile (28 mg, 0.11 mmol) obtained in the above-described example.
¹H NMR (CDCl₃, 400 MHz): δ=1.29 (t, 3H, J=7Hz), 1.47 (s, 6H), 4.27 (q, 2H, J=7Hz), 7.43 (d, 11H, J=9Hz), 7.79 (d, 2H, J=9Hz), 7.86 (d, 2H, J=9Hz), 7.94 (d, 1H, J=9Hz).

EXAMPLE 30

2-[[4-(4-Cyanophenyl)benzo[c][1,2,5]thiadiazol-5-yl]oxy]-2-methylpropanoic acid

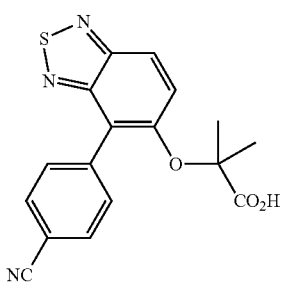 [SMILES: CC(C)(Oc1ccc2nsnc2c1-c1ccc(C#N)cc1)C(=O)O]

A title compound (pale brown crystal, 17 mg, yield of 77%) was obtained according to the same method as in Example 26 using ethyl 2-[[4-(4-cyanophenyl)benzo[c][1,2,5]thiadiazol-5-yl]oxy]-2-methylpropanoate (24 mg, 0.07 mmol) obtained in Example 29.
¹H NMR (CDCl₃, 400 MHz): δ=1.49 (s, 6H), 7.53 (d, 1H, J=9Hz), 7.80 (d, 2H, J=8Hz), 7.84 (d, 2H, J=8Hz), 7.98 (d, 1H, J=9Hz).

EXAMPLE 31

Ethyl 2-[[4-(4-cyanophenyl)benzo[c][1,2,5]thiadiazol-5-yl]thio]-2-methylpropanoate

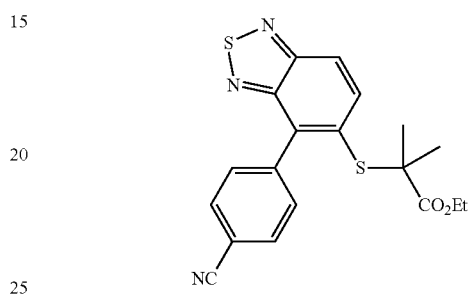

(1) Dimethylcarbamothioic acid O-[4-(4-cyanophenyl)benzo[c][1,2,5]thiadiazol-5-yl]

A title compound (light yellow crystal, 140 mg, yield of 95%) was obtained according to the same method as in Example 22 (1) using 4-(5-hydroxybenzo[c][1,2,5]thiadiazol-4-yl)benzonitrile (110 mg, 0.43 mmol) obtained in Example 29 (1).
¹H NMR (CDCl₃, 400 MHz): δ=3.19 (s, 3H), 3.40 (s, 3H), 7.54 (d, 1H, J=9Hz), 7.79 (s, 4H), 8.02 (d, 1H, J=9Hz).

(2) Dimethylcarbamothioic acid S-[4-(4-cyanophenyl)benzo[c][1,2,5]thiadiazol-5-yl]

A title compound (brown crystal, 80 mg, yield of 69%) was obtained at 250° C. according to the same method as in Example 3 (2) using dimethylcarbamothioic acid O-[4-(4-cyanophenyl)benzo[c][1,2,5]thiadiazol-5-yl] (116 mg, 0.34 mmol) obtained in the above-described example.
¹H NMR (CDCl₃, 400 MHz): δ=3.01 (s, 6H), 7.61 (d, 2H, J=8Hz), 7.80 (d, 2H, J=8Hz), 7.82 (d, 1H, J=9Hz), 8.03 (d, 1H, J=9Hz).

(3) 4-(5-Mercaptobenzo[c][1,2,5]thiadiazol-4-yl)benzonitrile

A title compound (yellowish brown crystal, 55 mg, yield of 87%) was obtained according to the same method as in Example 22 (3) using dimethylcarbamothioic acid S-[4-(4-cyanophenyl)benzo[c][1,2,5]thiadiazol-5-yl] (79 mg, 0.23 mmol) obtained in the above-described example.
¹H NMR (CDCl₃, 400 MHz): δ=3.61 (s, 1H), 7.58 (d, 1H, J=9Hz), 7.67 (d, 2H, J=8Hz), 7.87 (d, 2H, J=8Hz), 7.92 (d, 1H, J=9Hz).

(4) Ethyl 2-[[4-(4-cyanophenyl)benzo[c][1,2,5]thiadiazol-5-yl]thio]-2-methylpropanoic acid A title compound (pale yellow crystal, 49 mg, yield of 65%) was obtained according to the same method as in Example 1 (3) using 4-(5-mercaptobenzo[c][1,2,5]thiadiazol-4-yl)benzonitrile (54 mg, 0.2 mmol) obtained in the above-described example.

$^1$H NMR (CDCl$_3$, 400 MHz): δ=1.22 (t, 3H, J=7Hz), 1.39 (s, 6H), 4.07 (q, 2H, J=7Hz), 7.60 (d, 2H, J=9Hz), 7.79 (d, 1H, J=9Hz), 7.81 (d, 2H, J=9Hz), 7.97 (d, 1H, J=9Hz).

EXAMPLE 32

2-[[4-(4-cyanophenyl)benzo[c][1,2,5]thiadiazol-5-yl]thio]-2-methylpropanoic acid

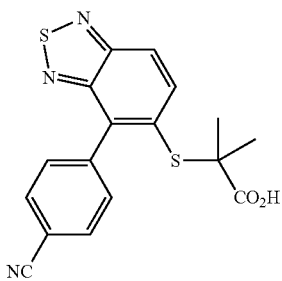 [SMILES: CC(C)(Sc1ccc2nsnc2c1-c1ccc(C#N)cc1)C(=O)O]

A title compound (light yellow crystal, 30 mg, yield of 65%) was obtained according to the same method as in Example 26 using ethyl 2-[[4-(4-cyanophenyl)benzo[c][1,2,5]thiadiazol-5-yl]thio]-2-methylpropanoic acid (49 mg, 0.13 mmol) obtained in Example 31.

$^1$H NMR (CDCl$_3$, 400 MHz): δ=1.43 (s, 6H), 7.60 (d, 2H, J=8Hz), 7.79 (d, 2H, J=8Hz), 7.87 (d, 1H, J=9Hz), 7.99 (d, 1H, J=9Hz).

EXAMPLE 33

2-[[4-(4-Cyanophenyl)-1H-indol-5-yl]oxy]-2-methyl propanoic acid

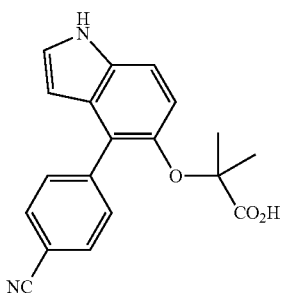 [SMILES: CC(C)(Oc1ccc2[nH]ccc2c1-c1ccc(C#N)cc1)C(=O)O]

(1) 4-[5-Hydroxy-1-(phenylsulfonyl)-1H-indol-4-yl]benzonitrile

A title compound (330 mg, yield of 57%) was obtained according to the same method as in Example 1 (1) using 4-bromo-1-(phenylsulfonyl)-1H-indol-5-ol (530 mg, 1.5 mmol) and (4-cyanophenyl)boronic acid.

$^1$H NMR (CDCl$_3$, 400 MHz): δ=4.94 (s, 1H), 6.41 (d, 1H, J=4Hz), 6.97 (d, 1H, J=9Hz), 7.4-7.5 (m, 2H), 7.5-7.6 (m, 4H), 7.78 (d, 2H, J=8Hz,), 7.8-8.0 (m, 3H).

(2) 2-[[4-(4-Cyanophenyl)-1H-indol-5-yl]oxy]-2-methylpropanoic acid

A title compound (white crystal, 3 mg, yield of 5%) was obtained according to the same method as in Examples 1 (3) and 26 using 4-[5-hydroxy-1-(phenylsulfonyl)-1H-indol-4-yl]benzonitrile (78 mg, 0.2 mmol) obtained in the above-described example.

$^1$H NMR (DMSO-d$_6$, 400 MHz): δ=1.21 (s, 6H), 6.20 (s, 1H), 6.88 (d, 1H, J=9Hz), 7.37 (d, 1H, J=9Hz), 7.38 (s, 1H), 7.72 (d, 2H, J=8Hz), 7.91 (d, 2H, J=8Hz,), 11.22 (s, 1H).

EXAMPLE 34

Ethyl 2-[[6-(4-cyanophenyl)benzo[d]thiazol-5-yl]oxy]-2-methylpropanoate

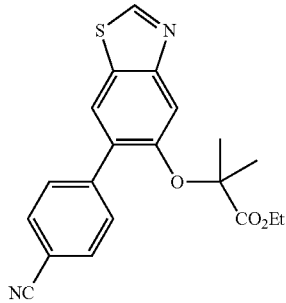 [SMILES: CCOC(=O)C(C)(C)Oc1cc2ncsc2cc1-c1ccc(C#N)cc1]

(1) 4-(5-Hydroxybenzo[d]thiazol-6-yl)benzonitrile

A title compound (brown crystal, 99 mg, yield of 29%) was obtained according to the same method as in Example 1 (1) using 6-bromo-5-methoxybenzo[d]thiazole (332 mg, 1.36 mmol) and (4-cyanophenyl)boronic acid.

$^1$H NMR (CDCl$_3$, 400 MHz): δ=3.91 (s, 3H), 7.6-7.7 (m, 2H), 7.7-7.8 (m, 3H), 7.82 (s, 1H), 9.01 (s, 1H).

(2) 4-(5-Hydroxybenzo[d]thiazol-6-yl)benzonitrile

A title compound (brown crystal, 98 mg, yield of 100%) was obtained according to the same method as in Example 18 (2) using 4-(5-methoxybenzo[d]thiazol-6-yl)benzonitrile (98 mg, 0.37 mmol) obtained in the above-described example.

$^1$H NMR (CD$_3$OD, 400 MHz): δ=7.7-7.8 (m, 5H), 7.84 (s, 1H), 9.03 (s, 1H).

(3) Ethyl 2-[[6-(4-cyanophenyl)benzo[d]thiazol-5-yl]oxy]-2-methylpropanoate

A title compound (yellow amorphous, 53 mg, yield of 26%) was obtained according to the same method as in Example 1 (3) using 4-(5-hydroxybenzo[d]thiazol-6-yl)benzonitrile (140 mg, 0.56 mmol) obtained in the above-described example.

$^1$H NMR (CDCl$_3$, 400 MHz): δ=1.27 (t, 3H, J=7Hz), 1.53 (s, 6H), 4.27 (q, 2H, J=7Hz), 7.61 (s, 1H), 7.72 (s, 4H), 7.86 (s, 1H), 9.01 (s, 1H).

EXAMPLE 35

2-[[6-(4-Cyanophenyl)benzo[d]thiazol-5-yl]oxy]-2-methylpropanoic acid

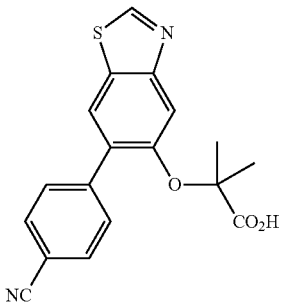 [SMILES: CC(C)(Oc1cc2ncsc2cc1-c1ccc(C#N)cc1)C(=O)O]

A title compound (white crystal, 23 mg, yield of 48%) was obtained according to the same method as in Example 2 using ethyl 2-[[6-(4-cyanophenyl)benzo[d]thiazol-5-yl]oxy]-2-methylpropanoate (52 mg, 0.142 mmol) obtained in Example 34.

$^1$H NMR (DMSO-$d_6$, 400 MHz): δ=1.53 (s, 6H), 7.65 (s, 1H), 7.80 (s, 4H), 8.04 (s, 1H), 9.25 (s, 1H).

EXAMPLE 36

Ethyl 2-[[6-(4-cyanophenyl)benzo[d]thiazol-7-yl]oxy]-2-methylpropanoate

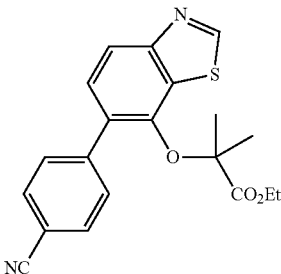 [SMILES: CCOC(=O)C(C)(C)Oc1c(-c2ccc(C#N)cc2)ccc2ncsc12]

(1) 4-(7-Methoxybenzo[d]thiazol-6-yl)benzonitrile

A title compound (white crystal, 267 mg, yield of 62%) was obtained according to the same method as in Example 16 (2) using 6-bromo-7-methoxybenzo[d]thiazole (396 mg, 1.62 mmol) and (4-cyanophenyl)boronic acid (357 mg, 2.43 mmol).

$^1$H NMR (CDCl$_3$, 400 MHz): δ=3.70 (s, 3H), 7.48 (d, 1H, J=8Hz), 7.7-7.8 (m, 4H), 7.95 (d, 1H, J=8Hz), 9.02 (s, 1H).

(2) 4-(7-Hydroxybenzo[d]thiazol-6-yl)benzonitrile

A title compound (brown oil material, 221 mg, yield of 87%) was obtained according to the same method as in Example 12 (2) using 4-(7-methoxybenzo[d]thiazol-6-yl)benzonitrile (267 mg, 1.0 mmol).

$^1$H NMR (CDCl$_3$, 400 MHz): δ=5.80 (br s, 1H), 7.41 (d, 1H, J=8Hz), 7.6-7.7 (m, 2H), 7.8-7.9 (m, 3H), 9.04 (s, 1H).

(3) Ethyl 2-[[6-(4-cyanophenyl)benzo[d]thiazol-7-yl]oxy]-2-methylpropanoate

A title compound (37 mg, yield of 33%) was obtained according to the same method as in Example 1 (3) using 4-(7-hydroxybenzo[d]thiazol-6-yl)benzonitrile (78 mg, 0.31 mmol).

$^1$H NMR (CDCl$_3$, 400 MHz): δ=1.18 (s, 6H), 1.30 (t, 3H, J=7Hz), 4.17 (q, 2H, J=7Hz), 7.47 (d, 1H, J=8Hz), 7.7-7.8 (m, 4H), 8.01 (d, 1H, J=9Hz), 9.02 (s, 1H).

EXAMPLE 37

2-[[6-(4-Cyanophenyl)benzo[d]thiazol-7-yl]oxy]-2-methylpropanoic acid

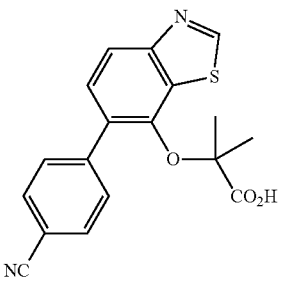 [SMILES: CC(C)(Oc1c(-c2ccc(C#N)cc2)ccc2ncsc12)C(=O)O]

A title compound (pale brown amorphous, 8.5 mg, yield of 25%) was obtained according to the same method as in Example 2 using ethyl 2-[[6-(4-cyanophenyl)benzo[d]thiazol-7-yl]oxy]-2-methylpropanoate (37 mg, 0.10 mmol) obtained in Example 36.

$^1$H NMR (CD$_3$OD, 400 MHz): δ=1.12 (s, 6H), 7.58 (d, 1H, J=8Hz), 7.8-7.9 (m, 4H), 7.96 (d, 1H, J=8Hz), 9.26 (s, 1H).

EXAMPLE 38

Ethyl 2-[[6-(4-cyanophenyl)benzo[d]thiazol-7-yl]thio]-2-methylpropanoate

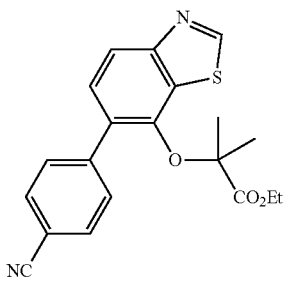 [SMILES: CCOC(=O)C(C)(C)Oc1c(-c2ccc(C#N)cc2)ccc2ncsc12]

(1) Dimethylcarbamothioic acid O-[6-(4-cyanophenyl)benzo[d]thiazol-7-yl]

A title compound (yellow oil material, 216 mg, yield of 73%) was obtained according to the same method as in Example 22 (1) using 4-(7-hydroxybenzo[d]thiazol-6-yl)benzonitrile (221 mg, 0.88 mmol) obtained in Example 36 (2).

$^1$H NMR (CDCl$_3$, 400 MHz): δ=3.21 (s, 3H), 3.34 (s, 3H), 7.50 (d, 1H, J=8Hz), 7.6-7.7 (m, 2H), 7.7-7.8 (m, 2H), 8.10 (d, 1H, J 8Hz), 9.02 (s, 1H).

(2) Ethyl 2-[[6-(4-cyanophenyl)benzo[d]thiazol-7-yl]thio]-2-methylpropanoate

A title compound (colorless oil material, 8 mg, yield of 3%) was obtained according to the same method as in Examples 3 (2), 3 (3), and 1 (3) using dimethylcarbamothioic acid O-[6-(4-cyanophenyl)benzo[d]thiazol-7-yl] (216 mg, 0.64 mmol) obtained in the above-described example.

$^1$H NMR (CD$_3$OD, 400 MHz): δ=1.17 (s, 6H), 1.31 (t, 3H, J=7Hz), 3.21 (q, 2H, J=7Hz), 7.65 (d, 1H, J=8Hz), 7.73 (d, 2H, J=9Hz), 7.80 (d, 2H, J=8Hz), 8.17 (d, 1H, J=8Hz), 9.30 (s, 1H).

EXAMPLE 39

2-[[6-(4-Cyanophenyl)benzo[d]thiazol-7-yl]thio]-2-methylpropanoic acid

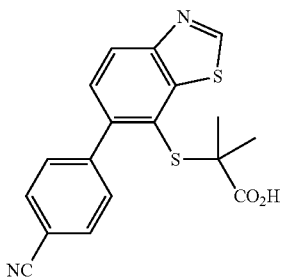 [SMILES: CC(C)(Sc1c(-c2ccc(C#N)cc2)ccc2ncsc12)C(=O)O]

A title compound (light pink amorphous, 5.5 mg, yield of 74%) was obtained according to the same method as in Example 2 using ethyl 2-[[6-(4-cyanophenyl)benzo[d]thiazol-7-yl]thio]-2-methylpropanoate (8 mg, 0.02 mmol) obtained in Example 38.

$^1$H NMR (CD$_3$OD, 400 MHz): δ=1.17 (s, 6H), 7.64 (d, 1H, J=8Hz), 7.7-7.8 (m, 4H), 8.16 (d, 1H, J=8Hz), 9.29 (s, 1H).

EXAMPLE 40

Ethyl 2-[[8-(4-cyanophenyl)imidazo[1,2-a]pyridin-7-yl]thio]-2-methylpropanoate

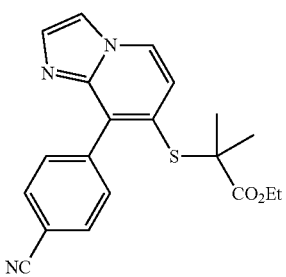 [SMILES: CCOC(=O)C(C)(C)Sc1ccn2ccnc2c1-c1ccc(C#N)cc1]

(1) 4-(7-Methoxyimidazo[1,2-a]pyridin-8-yl)benzonitrile

A title compound (light yellow crystal, 200 mg, yield of 71%) was obtained according to the same method as in Example 1 (1) using 8-iodo-7-methoxyimidazo[1,2-a]pyridine (350 mg, 1.13 mmol) and (4-cyanophenyl)boronic acid.

$^1$H NMR (CDCl$_3$, 400 MHz): δ=3.89 (s, 3H), 6.83 (d, 1H, J=7Hz), 7.56 (d, 2H, J=8Hz), 7.75 (d, 2H, J=8Hz), 7.87 (d, 2H, J=8Hz), 8.15 (d, 1H, J=7Hz).

(2) Dimethylcarbamothioic acid S-[8-(4-cyanophenyl)imidazo[1,2-a]pyridin-7-yl]

A title compound (brown crystal, 36 mg, yield of 14%) was obtained according to the same method as in Examples 12 (2), 3 (1), and 3 (2) using 4-(7-methoxyimidazo[1,2-a]pyridin-8-yl)benzonitrile (200 mg, 0.80 mmol) obtained in the above-described example.

$^1$H NMR (CDCl$_3$, 400 MHz): δ=2.98 (s, 6H), 7.04 (d, 1H, J=7Hz), 7.62 (d, 2H, J=8Hz), 7.65-7.70 (m, 2H), 7.76 (d, 2H, J=8Hz), 8.15 (d, 1H, J=7Hz).

(3) Ethyl 2-[[8-(4-cyanophenyl)imidazo[1,2-a]pyridin-7-yl]thio]-2-methyl propanoate A title compound (brown oil material, 26 mg, yield of 65%) was obtained according to the same method as in Examples 3 (3) and 1 (3) using dimethylcarbamothioic acid S-[8-(4-cyanophenyl)imidazo[1,2-a]pyridin-7-yl] (36 mg, 0.11 mmol) obtained in the above-described example.

$^1$H NMR (CDCl$_3$, 400 MHz): δ=1.22 (t, 3H, J=7Hz), 1.36 (s, 6H), 4.07 (q, 2H, J=7Hz), 6.99 (d, 1H, J=7Hz), 7.6-7.7 (m, 3H), 7.77 (d, 2H, J=8Hz), 8.02 (s, 1H), 8.09 (d, 1H, J=7Hz).

EXAMPLE 41

2-[[8-(4-Cyanophenyl)imidazo[1,2-a]pyridin-7-yl]thio]-2-methylpropanoic acid

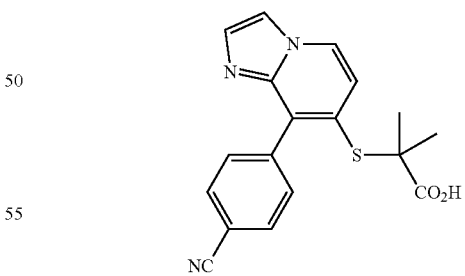

A title compound (off-white crystal, 7 mg, yield of 29%) was obtained according to the same method as in Example 2 using ethyl 2-[[8-(4-cyanophenyl)imidazo[1,2-a]pyridin-7-yl]thio]-2-methylpropanoate (26 mg, 0.07 mmol) obtained in Example 40.

$^1$H NMR (CD$_3$OD, 400 MHz): δ=1.38 (s, 6H), 7.24 (d, 1H, J=7Hz), 7.5-7.6 (m, 3H), 7.8-7.9 (m, 2H), 7.94 (d, 1H, J=1Hz), 8.43 (d, 1H, J=7Hz).

EXAMPLE 42

Ethyl 2-[[6-(4-cyanophenyl)imidazo[1,2-a]pyridin-7-yl]oxy]-2-methylpropanoate

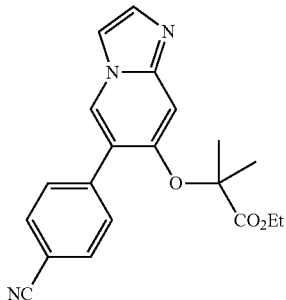 [SMILES: CCOC(=O)C(C)(C)Oc1cc2nccn2cc1-c1ccc(C#N)cc1]

(1) 4-(7-Methoxyimidazo[1,2-a]pyridin-6-yl)benzonitrile

A title compound (white crystal, 52 mg, yield of 21%) was obtained according to the same method as in Example 1 (1) using 6-bromo-7-methoxyimidazo[1,2-a]pyridine (227 mg, 1.0 mmol) and (4-cyanophenyl)boronic acid.

$^1$H NMR (CDCl$_3$, 400 MHz): δ=3.89 (s, 3H), 7.01 (s, 1H), 7.48 (s, 1H), 7.54 (s, 1H), 7.6-7.65 (m, 2H), 7.7-7.8 (m, 2H), 8.00 (s, 1H).

(2) 4-(7-Hydroxyimidazo[1,2-a]pyridin-6-yl)benzonitrile

A title compound (pale yellow oil material, 22 mg, yield of 62%) was obtained according to the same method as in Example 18 (2) using 4-(7-methoxyimidazo[1,2-a]pyridin-6-yl)benzonitrile (31 mg, 0.13 mmol).

$^1$H NMR (DMSO-d$_6$, 400 MHz): δ=7.81 (d, 1H, J=8Hz), 7.9-8.2 (m, 7H), 8.93 (s, 1H).

(3) Ethyl 2-[[6-(4-cyanophenyl)imidazo[1,2-a]pyridin-7-yl]oxy]-2-methylpropanoate A title compound (pale brown crystal, 9 mg, yield of 48%) was obtained according to the same method as in Example 1 (3) using 4-(7-hydroxyimidazo[1,2-a]pyridin-6-yl)benzonitrile (22 mg, 0.06 mmol).

$^1$H NMR (CDCl$_3$, 400 MHz): δ=1.27 (t, 3H, J=7Hz), 1.61 (s, 6H), 4.26 (q, 2H, J=7Hz), 6.84 (s, 1H), 7.48 (d, 1H, J=1Hz), 7.54 (d, 1H, J=1Hz), 7.65 (d, 2H, J=9Hz), 7.73 (d, 2H, J=9Hz), 8.02 (s, 1H).

EXAMPLE 43

2-[[6-(4-Cyanophenyl)imidazo[1,2-a]pyridin-7-yl]oxy]-2-methylpropanoic acid

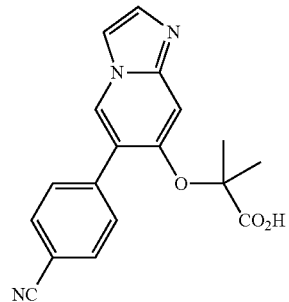 [SMILES: CC(C)(Oc1cc2nccn2cc1-c1ccc(C#N)cc1)C(=O)O]

A title compound (yield of 48%) was obtained according to the same method as in Example 26 using ethyl 2-[[6-(4-cyanophenyl)imidazo[1,2-a]pyridin-7-yl]oxy]-2-methylpropanoate obtained in Example 42.

$^1$H NMR (DMSO-d$_6$, 400 MHz): δ=1.54 (s, 6H), 6.74 (s, 1H), 7.45 (s, 1H), 7.78 (s, 1H), 7.79 (d, 2H, J=8Hz), 7.93 (d, 2H, J=8Hz), 8.62 (s, 1H).

EXAMPLE 44

Ethyl 2-[[3-(4-cyanophenyl)quinolin-4-yl]thio]-2-methylpropanoate

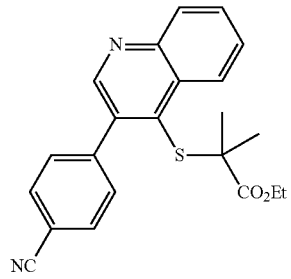 [SMILES: CCOC(=O)C(C)(C)Sc1c(-c2ccc(C#N)cc2)cnc2ccccc12]

(1) 4-(4-Hydroxyquinolin-3-yl)benzonitrile

A title compound (brown crystal, 50 mg, yield of 9%) was obtained according to the same method as in Example 16 (2) using 3-iodoquinolin-4-ol (580 mg, 2.14 mmol) and (4-cyanophenyl)boronic acid.

$^1$H NMR (CD$_3$OD, 400 MHz): δ=7.4-7.9 (m, 5H), 7.90 (d, 2H, J=8Hz), 8.23 (s, 1H), 8.35 (dd, 1H, J=1Hz, 8Hz).

(2) Ethyl 2-[[3-(4-cyanophenyl)quinolin-4-yl]thio]-2-methylpropanoate 4-(4-Hydroxyquinolin-3-yl)benzonitrile (90 mg, 0.37 mmol) obtained in the above-described example was dissolved in tetrahydrofuran (4 mL), Lawesson's reagent (449 mg, 1.11 mmol) was added thereto, and the solution was stirred at 70° C. in a nitrogen atmosphere. After 16 hours, the reaction solution was diluted with ethyl acetate, the organic layer was washed with water and brine, dried over sodium sulfate, and filtered, and then the solvent was distilled off under reduced pressure. A title compound (yellow oil material, 44 mg, yield of 32%) was obtained in the same method as in Example 1 (3) using the obtained residue.

$^1$H NMR (CDCl$_3$, 400 MHz): δ=1.19 (s, 6H), 1.26 (t, 3H, J=7Hz), 3.55 (q, 2H, J=7Hz), 7.6-7.9 (m, 6H), 8.18 (d, 1H, J=9Hz), 8.69 (d, 1H, J=9Hz), 8.94 (s, 1H).

EXAMPLE 45

2-[[3-(4-Cyanophenyl)quinolin-4-yl]thio]-2-methyl-propanoic acid

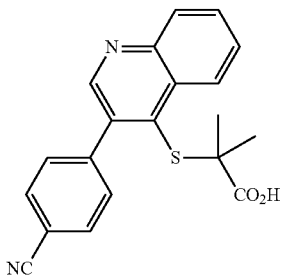 [SMILES: CC(C)(Sc1c(-c2ccc(C#N)cc2)cnc2ccccc12)C(=O)O]

A title compound (light yellow crystal, 15 mg, yield of 31%) was obtained according to the same method as in Example 2 using ethyl 2-[[3-(4-cyanophenyl)quinolin-4-yl]thio]-2-methylpropanoate (44 mg, 0.12 mmol) obtained in Example 44.

$^1$H NMR (CDCl$_3$, 400 MHz): δ=1.28 (s, 6H), 7.6-7.8 (m, 6H), 8.11 (d, 1H, J=8Hz), 8.8-8.9 (m, 1H), 8.88 (s, 1H).

EXAMPLE 46

Ethyl (E)-3-[[1-(4-cyanophenyl)naphthalen-2-yl]oxy]-2-butenoate

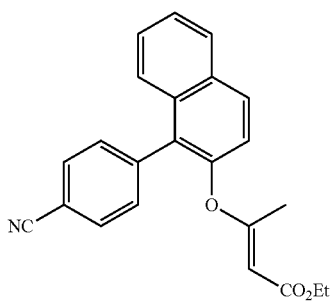 [SMILES: CCOC(=O)/C=C(\C)Oc1ccc2ccccc2c1-c1ccc(C#N)cc1]

A title compound (white crystal, 111 mg, yield of 76%) was obtained according to the same method as in Example 3 (1) using 4-(2-hydroxynaphthalen-1-yl)benzonitrile (100 mg, 0.41 mmol) and ethyl 2-butynoate (71 μL, 0.61 mmol).

$^1$H NMR (CDCl$_3$, 400 MHz): δ=1.19 (t, 3H, J=7Hz), 2.24 (s, 3H), 4.06 (q, 2H, J=7Hz), 4.82 (s, 1H), 7.26 (d, 1H, J=9Hz), 7.4-7.6 (m, 5H), 7.7-7.8 (m, 2H), 7.93 (d, 1H, J=8Hz), 7.96 (d, 1H, J=9Hz).

EXAMPLE 47

(E)-3-[[1-(4-cyanophenyl)naphthalen-2-yl]oxy]-2-butenoic acid

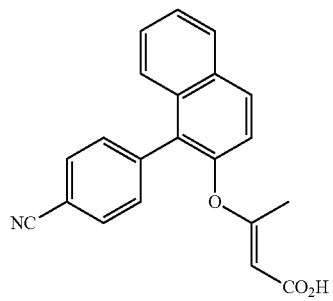 [SMILES: C/C(=C\C(=O)O)Oc1ccc2ccccc2c1-c1ccc(C#N)cc1]

A title compound (white crystal, 16 mg, yield of 16%) was obtained according to the same method as in Example 2 using ethyl (E)-3-[[1-(4-cyanophenyl)naphthalen-2-yl]oxy]-2-butenoate (111 mg, 0.31 mmol) obtained in Example 46.

$^1$H NMR (CDCl$_3$, 400 MHz): δ=2.21 (s, 3H), 4.80 (s, 1H), 7.25 (d, 11-1, J=9Hz), 7.4-7.6 (m, 5H), 7.7-7.8 (m, 2H), 7.93 (d, 1H, J=8Hz), 7.96 (d, 1H, J=9Hz).

EXAMPLE 48 t-Butyl 2-[[1-(4-cyanophenyl)naphthalen-2-yl]thio]-2-methylpropanoate

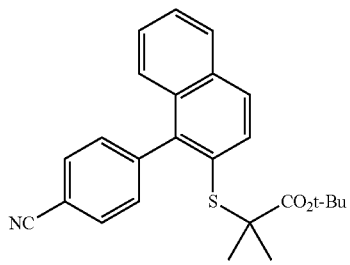 [SMILES: CC(C)(C)OC(=O)C(C)(C)Sc1ccc2ccccc2c1-c1ccc(C#N)cc1]

(1) Dimethylcarbamothioic acid O-[1-(4-cyanophenyl)naphthalen-2-yl]

A title compound (light yellow crystal, 258 mg, yield of 76%) was obtained according to the same method as in Example 22 (1) using 4-(2-hydroxynaphthalen-1-yl)benzonitrile (250 mg, 1.02 mmol).

$^1$H NMR (CD$_3$OD, 400 MHz): δ=2.99 (s, 3H), 3.31 (s, 3H), 7.34 (d, 1H, J=9Hz), 7.4-7.5 (m, 3H), 7.57 (d, 2H, J=8Hz), 7.76 (d, 2H, J=8Hz), 7.9-8.0 (m, 2H).

(2) Dimethylcarbamothioic acid S-[1-(4-cyanophenyl)naphthalen-2-yl]

A title compound (pale brown crystal, 231 mg, yield of 90%) was obtained at 230° C. according to the same method as in Example 3 (2) using dimethylcarbamothioic acid O-[1-(4-cyanophenyl)naphthalen-2-yl] (256 mg, 0.77 mmol) obtained in the above-described example.

¹H NMR (CDCl₃, 400 MHz): δ=2.93 (s, 6H), 7.29 (d, 1H, J=9Hz), 7.38 (dt, 1H, J=1Hz, 8Hz), 7.43 (d, 2H, J=8Hz), 7.52 (dt, 1H, J=1Hz, 8Hz), 7.65 (d, 1H, J=9Hz), 7.75 (d, 2H, J=9Hz), 7.8-7.9 (m, 2H).

(3) 4-(2-Mercaptonaphthalen-1-yl)benzonitrile

A title compound (light yellow crystal, 80 mg, yield of 44%) was obtained according to the same method as in Example 22 (3) using dimethylcarbamothioic acid S-[1-(4-cyanophenyl)naphthalen-2-yl] (230 mg, 0.69 mmol) obtained in the above-described example.

¹H NMR (CDCl₃, 400 MHz): δ=3.32 (s, 1H), 7.20 (d, 1H, J=8Hz), 7.3-7.5 (m, 5H), 7.77 (d, 1H, J=9Hz), 7.8-7.9 (m, 3H).

(4) t-Butyl 2-[[1-(4-cyanophenyl)naphthalen-2-yl]thio]-2-methylpropanoate

A title compound (light yellow crystal, 37 mg, yield of 80%) was obtained according to the same method as in Example 1 (3) using 4-(2-mercaptonaphthalen-1-yl)benzonitrile (30 mg, 0.12 mmol) obtained in the above-described example and t-butyl 2-bromoisobutyrate (43 μL, 0.23 mmol).

¹H NMR (CDCl₃, 400 MHz): δ=1.31 (s, 6H), 1.47 (s, 9H), 7.2-7.3 (m, 1H), 7.3-7.4 (m, 3H), 7.49 (t, 1H, J=8Hz), 7.67 (d, 1H, J=9Hz), 7.79 (d, 2H, J=8Hz), 7.83 (d, 1H, J=9Hz), 7.87 (d, 1H, J=8Hz).

EXAMPLE 49

2-[[1-(4-Cyanophenyl)naphthalen-2-yl]thio]-2-methyl propanoic acid

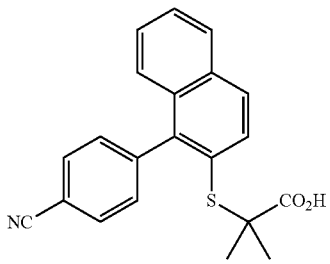 [SMILES: CC(C)(Sc1ccc2ccccc2c1-c1ccc(C#N)cc1)C(=O)O]

A title compound (white crystal, 28 mg, yield of 90%) was obtained according to the same method as in Example 6 using t-butyl 2-[[1-(4-cyanophenyl)naphthalen-2-yl]thio]-2-methylpropanoate (36 mg, 0.09 mmol) obtained in Example 48.

¹H NMR (CD₃OD, 400 MHz): δ=1.36 (s, 6H), 7.27 (d, 1H, J=9Hz), 7.3-7.5 (m, 3H), 7.53 (dt, 1H, J=1Hz, 7Hz), 7.73 (d, 1H, J=9Hz), 7.85 (d, 2H, J=9Hz), 7.90 (d, 1H, J=9Hz), 7.93 (d, 1H, J=8Hz).

EXAMPLE 50 t-Butyl (E)-3-[[1-(4-cyanophenyl)naphthalen-2-yl]thio]acrylate

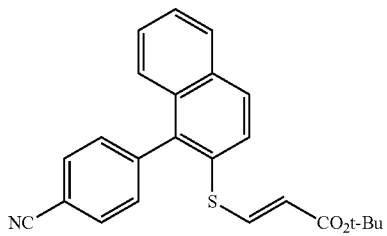 [SMILES: CC(C)(C)OC(=O)/C=C/Sc1ccc2ccccc2c1-c1ccc(C#N)cc1]

A title compound (white crystal, 24 mg, yield of 41%) was obtained according to the same method as in Example 9 using 4-(2-mercaptonaphthalen-1-yl)benzonitrile (40 mg, 0.15 mmol) obtained in Example 48 (3) and t-butyl propiolate (63 μL, 0.46 mmol).

¹H NMR (CDCl₃, 400 MHz): δ=1.43 (s, 9H), 5.46 (d, 1H, J=15Hz), 7.32 (d, 1H, J=8Hz), 7.4-7.5 (m, 3H), 7.5-7.6 (m, 2H), 7.63 (d, 1H, J=8Hz), 7.78 (d, 2H, J=8Hz), 7.9-8.0 (m, 2H).

EXAMPLE 51

(E)-3-[[1-(4-cyanophenyl)naphthalen-2-yl]thio]acrylic acid

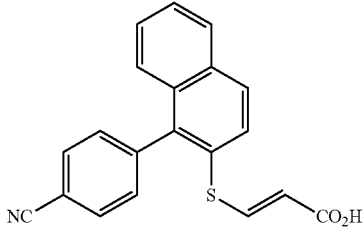 [SMILES: N#Cc1ccc(-c2c(S/C=C/C(=O)O)ccc3ccccc23)cc1]

A title compound (white amorphous, 11 mg, yield of 55%) was obtained according to the same method as in Example 6 using t-butyl (E)-3-[[1-(4-cyanophenyl)naphthalen-2-yl]thio]acrylate (24 mg, 0.06 mmol) obtained in Example 50.

¹H NMR (CDCl₃, 400 MHz): δ=5.46 (d, 1H, J=15Hz), 7.34 (d, 1H, J=8Hz), 7.41 (d, 2H, J=8Hz), 7.46 (t, 1H, J=7Hz), 7.59 (t, 11H, J=8Hz), 7.63 (d, 1H, J=9Hz), 7.7-7.8 (m, 3H), 7.94 (d, 1H, J=8Hz), 7.97 (d, 1H, J=9Hz).

EXAMPLE 52

2-[[7-(4-Cyanophenyl)benzo[d]thiazol-6-yl]thio]-2-methylpropanamide

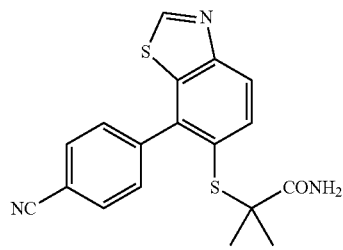 [SMILES: CC(C)(Sc1ccc2ncsc2c1-c1ccc(C#N)cc1)C(N)=O]

2-[[7-(4-Cyanophenyl)benzo[d]thiazol-6-yl]thio]-2-methylpropanoic acid (30 mg, 0.09 mmol) obtained in Example 24 was dissolved in toluene (1 mL), thionyl chloride (62 µL, 0.85 mmol) was added thereto, and the solution was stirred at 80° C. in a nitrogen atmosphere. After 6 hours, the solvent was distilled off under reduced pressure, the obtained residue was dissolved in tetrahydrofuran (2 mL), a 25% NH$_3$ aqueous solution (2 mL) was added thereto, and the solution was stirred at room temperature. After 14 hours, the solvent was distilled off under reduced pressure, and the obtained residue was purified by silica gel column chromatography (ethyl acetate:hexane=1:2) to obtain a title compound (white crystal, 7 mg, yield of 23%).

$^1$H NMR (CDCl$_3$, 400 MHz): δ=1.40 (s, 6H), 5.22 (br s, 1H), 6.36 (br s, 1H), 7.55 (d, 2H, J=8Hz), 7.78 (d, 1H, J=9Hz), 7.81 (d, 2H, J=8Hz), 8.11 (d, 1H, J=9Hz), 9.01 (s, 1H).

EXAMPLE 53

2-[[7-(4-Cyanophenyl)benzo[d]thiazol-6-yl]thio]-N-(5-fluoropyridin-2-yl)-2-me thylpropanamide

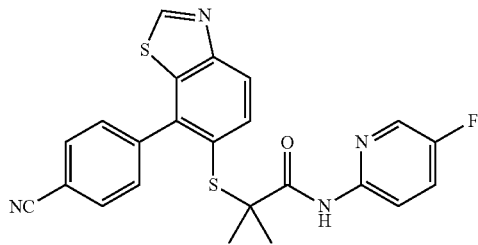 [SMILES: CC(C)(Sc1ccc2ncsc2c1-c1ccc(C#N)cc1)C(=O)Nc1ccc(F)cn1]

2-[[7-(4-Cyanophenyl)benzo[d]thiazol-6-yl]thio]-2-methylpropanoic acid (30 mg, 0.09 mmol) obtained in Example 24, 5-fluoropyridin-2-amine (11 mg, 0.10 mmol), diisopropylethylamine (29 µL, 0.19 mmol), and N,N,N',N'-tetramethyl-O-(7-azabenzotriazol-1-yl)uranium hexafluorophosphate (39 mg, 0.10 mmol) were dissolved in tetrahydrofuran (1 mL), and the solution was stirred at room temperature. After 3 hours, the reaction solution was diluted with ethyl acetate and washed with water and brine. The organic layer was dried over sodium sulfate and filtered, and then the solvent was distilled off under reduced pressure. The obtained residue was purified by silica gel column chromatography (ethyl acetate:hexane=1:2) to obtain a title compound (10 mg, yield of 26%).

$^1$H NMR (CDCl$_3$, 400 MHz): δ=1.46 (s, 6H), 7.4-7.6 (m, 3H), 7.62 (d, 2H, J=8Hz), 7.71 (d, 1H, J=8Hz), 8.05 (d, 1H, J=8Hz), 8.10 (dd, 1H, J=4Hz, 9Hz), 8.17 (d, 1H, J=3Hz), 8.65 (s, 1H), 9.0 (s, 1H).

EXAMPLE 54

2-[[7-(4-Cyanophenyl)benzo[d]thiazol-6-yl]thio]-2 methyl-N-(1,3,4-thiadiazol-2-yl)propanamide

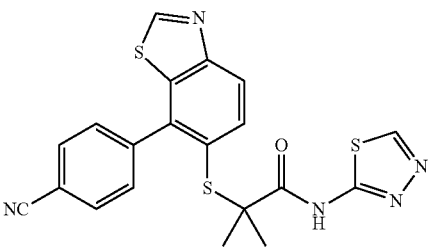 [SMILES: CC(C)(Sc1ccc2ncsc2c1-c1ccc(C#N)cc1)C(=O)Nc1nncs1]

A title compound (white crystal, 21 mg, yield of 57%) was obtained according to the same method as in Example 53 using 2-[[7-(4-cyanophenyl)benzo[d]thiazol-6-yl]thio]-2-methylpropanoic acid (30 mg, 0.09 mmol) obtained in Example 24 and 1,3,4-thiazol-2-amine (10 mg, 0.1 mmol).

$^1$H NMR (CD$_3$OD, 400 MHz): δ=1.48 (s, 6H), 7.54 (d, 2H, J=9Hz), 7.62 (d, 2H, J=8Hz), 7.80 (d, 1H, J=9Hz), 8.04 (d, 1H, J=9Hz), 9.06 (s, 1H), 9.29 (s, 1H).

EXAMPLE 55 t-Butyl 2-[[4-(4-cyanophenyl)benzo[d]thiazol-5-yl]oxy]-2-methylpropanoate

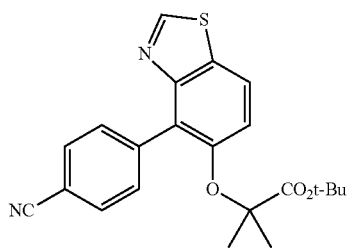 [SMILES: CC(C)(C)OC(=O)C(C)(C)Oc1ccc2scnc2c1-c1ccc(C#N)cc1]

(1) 4-Bromo-5-methoxybenzo[d]thiazol-2-amine

Sodium thiocyanate (1.6 g, 19.8 mmol) was dissolved in acetic acid (20 mL), and 2-bromo-3-methoxyaniline (1 g, 4.95 mmol) dissolved in acetic acid (20 mL) was added dropwise thereto. After dropwise addition, bromine (281 µL, 5.45 mmol) dissolved in acetic acid (10 mL) was added dropwise thereto, and the solution was stirred at room temperature. After 16 hours, the solvent was distilled off under reduced pressure and saturated sodium hydrogen carbonate aqueous solution was added to the residue. The precipitated solids were separated by filtration and the obtained crystals were washed with chloroform (20 mL) and methanol (20 mL) to obtain a title compound (brown crystal, 756 mg, yield of 59%).

$^1$H NMR (DMSO-d$_6$, 400 MHz): δ=3.87 (s, 3H), 6.84 (d, 1H, J=8Hz), 7.61 (d, 1H, J=8Hz), 7.87 (br s, 2H).

(2) 4-Bromo-5-methoxybenzo[d]thiazole 4-bromo-5-methoxybenzo[d]thiazol-2-amine (756 mg, 2.92 mmol) obtained in the above-described example was dissolved in tetrahydrofuran (30 mL), t-butyl nitrite (831 μL, 7.00 mmol) was added thereto, and the solution was stirred at 60° C. in a nitrogen atmosphere. After 1 hour, the solution was allowed to be cooled to room temperature, saturated sodium hydrogen carbonate aqueous solution was added to the reaction solution, and extraction was carried out using chloroform. The organic layer was dried over sodium sulfate and filtered, and then the solvent was distilled off under reduced pressure. The obtained residue was purified by silica gel column chromatography (ethyl acetate:hexane=1:2) to obtain a title compound (yellow crystal, 300 mg, yield of 42%).

$^1$H NMR (CDCl$_3$, 400 MHz): δ=4.02 (s, 3H), 7.15 (d, 1H, J=9Hz), 7.85 (d, 1H, J=9Hz), 9.09 (s, 1H).

(3) 4-(5-Methoxybenzo[d]thiazol-4-yl)benzonitrile

A title compound (light yellow crystal, 74 mg, yield of 28%) was obtained according to the same method as in Example 1 (1) using 4-bromo-5-methoxybenzo[d]thiazole (240 mg, 0.98 mmol) obtained in the above-described example and (4-cyanophenyl)boronic acid (216 mg, 1.47 mmol).

$^1$H NMR (CDCl$_3$, 400 MHz): δ=3.88 (s, 3H), 7.26 (d, 1H, J=9Hz), 7.72 (d, 2H, J=8Hz), 7.76 (d, 2H, J=8Hz), 7.95 (d, 1H, J=9Hz), 8.98 (s, 1H).

(4) t-Butyl 2-[[4-(4-cyanophenyl)benzo[d]thiazol-5-yl]oxy]-2-methylpropanoate A crude material of a title compound was obtained according to the same method as in Example 18 (2) using 4-(5-methoxybenzo[d]thiazol-4-yl)benzonitrile (74 mg, 0.28 mmol) obtained in the above-described example.

A title compound (pale yellow oil material, 5 mg, yield of 20%) was obtained according to the same method as in Example 1 (3) using the obtained crude material (15 mg) and t-butyl 2-bromoisobutyrate (33 μL, 0.18 mmol).

$^1$H NMR (CDCl$_3$, 400 MHz): δ=1.40 (s, 6H), 1.46 (s, 9H), 7.20 (d, 1H, J=9Hz), 7.7-7.8 (m, 4H), 7.85 (d, 1H, J=9Hz), 8.97 (s, 1H).

EXAMPLE 56

2-[[4-(4-Cyanophenyl)benzo[d]thiazol-5-yl]oxy]-2-methylpropanoic acid

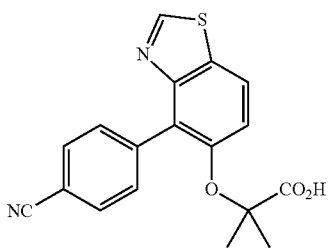 [SMILES: CC(C)(Oc1ccc2scnc2c1-c1ccc(C#N)cc1)C(=O)O]

A title compound (white crystal, 1.2 mg, yield of 30%) was obtained according to the same method as in Example 6 using t-butyl 2-[[4-(4-cyanophenyl)benzo[d]thiazol-5-yl]oxy]-2-methylpropanoate (5 mg, 0.01 mmol) obtained in Example 55.

$^1$H NMR (DMSO-d$_6$, 400 MHz): δ=1.27 (s, 6H), 7.67 (d, 2H, J=8Hz), 7.83 (d, 1H, J=8Hz), 8.02 (d, 2H, J=8Hz), 8.18 (d, 1H, J=8Hz), 9.50 (s, 1H).

EXAMPLE 57

Ethyl (E)-3-[[1-(4-cyanophenyl)naphthalen-2-yl]oxy]-2-petenoate

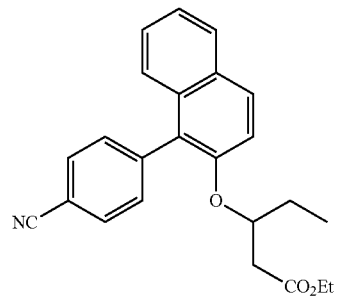 [SMILES: CCOC(=O)CC(CC)Oc1ccc2ccccc2c1-c1ccc(C#N)cc1]

A title compound (colorless oil material, 45 mg, yield of 30%) was obtained according to the same method as in Example 9 using 4-(2-hydroxynaphthalen-1-yl)benzonitrile (100 mg, 0.41 mmol) and ethyl 2-pentynate (81 μL, 0.61 mmol).

$^1$H NMR (CDCl$_3$, 400 MHz): δ=0.86 (t, 3H, J=8Hz), 1.17 (t, 3H, J=7Hz), 2.71 (q, 2H, J=8Hz), 4.03 (q, 2H, J=7Hz), 4.71 (s, 1H), 7.23 (d, 1H, J=9Hz), 7.4-7.6 (m, 5H), 7.75 (d, 2H, J=8Hz), 7.91 (d, 1H, J=8Hz), 7.94 (d, 1H, J=9Hz).

EXAMPLE 58

(E)-3-[[1-(4-cyanophenyl)naphthalen-2-yl]oxy]-2-pentenoic acid

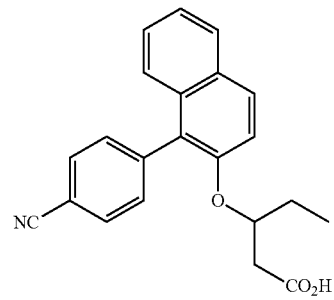 [SMILES: CCC(CC(=O)O)Oc1ccc2ccccc2c1-c1ccc(C#N)cc1]

A title compound (white crystal, 3.2 mg, yield of 38%) was obtained according to the same method as in Example 2 using ethyl (E)-3-[[1-(4-cyanophenyl)naphthalen-2-yl]oxy]-2-pentenoate (45 mg, 0.12 mmol) obtained in Example 57.

$^1$H NMR (CDCl$_3$, 400 MHz): δ=0.84 (t, 3H, J=7Hz), 2.68 (q, 2H, J=7Hz), 4.70 (s, 1H), 7.21 (d, 1H, J=9Hz), 7.4-7.6 (m, 5H), 7.75 (d, 2H, J=8Hz), 7.91 (d, 1H, J=8Hz), 7.95 (d, 1H, J=9Hz).

EXAMPLE 59 t-Butyl 2-[[7-(4-cyanophenyl)-2-(trifluoromethyl)benzo[d]thiazol-6-yl]thio]-2-methylpropanoate

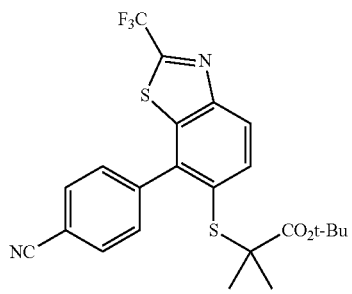 [SMILES: CC(C)(C)OC(=O)C(C)(C)Sc1ccc2nc(C(F)(F)F)sc2c1-c1ccc(C#N)cc1]

(1) 7-Bromo-6-methoxy-2-(trifluoromethyl)benzo[d]thiazole

A title compound (white crystal, 1.1 g, yield of 74%) was obtained according to the same method as in Example 25 (1) using 6-methoxy-2-(trifluoromethyl)benzo[d]thiazole (1.14 g, 4.89 mmol).
$^1$H NMR (CDCl$_3$, 400 MHz): δ=4.03 (s, 3H), 7.24 (d, 1H, J=9Hz), 8.13 (d, 1H, J=9Hz).

(2) 4-[6-Methoxy-2-(trifluoromethyl)benzo[d]thiazol-7-yl]benzonitrile

A title compound (white crystal, 462 mg, yield of 95%) was obtained according to the same method as in Example 16 (2) using 7-bromo-6-methoxy-2-(trifluoromethyl)benzo[d]thiazole (450 g, 1.44 mmol) and (4-cyanophenyl)boronic acid (254 mg, 1.73 mmol).
$^1$H NMR (CDCl$_3$, 400 MHz): δ=3.91 (s, 3H), 7.36 (d, 1H, J=9Hz), 7.67 (d, 2H, J=8Hz), 7.80 (d, 2H, J=8Hz), 8.19 (d, 1H, J=9Hz).

(3) Dimethylcarbamothioic acid O-[7-(4-cyanophenyl)-2-(trifluoromethyl)benzo[d]thiazol-6-yl]

A title compound (white crystal, 441 mg, yield of 92%) was obtained according to the same method as in Examples 18 (2) and 22 (1) using 4-[6-methoxy-2-(trifluoromethyl)benzo[d]thiazol-7-yl]benzonitrile (456 mg, 1.36 mmol) obtained in the above-described example.
$^1$H NMR (CDCl$_3$, 400 MHz): δ=3.13 (s, 3H), 3.33 (s, 3H), 7.45 (d, 1H, J=9Hz), 7.6-7.7 (m, 2H), 7.7-7.8 (m, 2H), 8.21 (d, 1H, J=9Hz).

(4) Dimethylcarbamothioic acid S-[7-(4-cyanophenyl)-2-(trifluoromethyl)benzo[d]thiazol-6-yl]

A title compound (white crystal, 521 mg, yield of 95%) was obtained according to the same method as in Example 27 (2) using dimethylcarbamothioic acid O-[7-(4-cyanophenyl)-2-(trifluoromethyl)benzo[d]thiazol-6-yl] (535 mg, 1.31 mmol) obtained in the above-described example.
$^1$H NMR (CDCl$_3$, 400 MHz): δ=2.95 (s, 6H), 7.5-7.6 (m, 2H), 7.7-7.8 (m, 2H), 7.86 (d, 1H, J=9Hz), 8.21 (d, 1H, J=8Hz).

(5) t-Butyl 2-[[7-(4-cyanophenyl)-2-(trifluoromethyl)benzo[d]thiazol-6-yl]thio]-2-methylpropanoate A title compound (white crystal, 254 mg, yield of 42%) was obtained according to the same method as in Examples 22 (3) and 23 using dimethylcarbamothioic acid S-[7-(4-cyanophenyl)-2-(trifluoromethyl)benzo[d]thiazol-6-yl] (521 mg, 1.27 mmol) obtained in the above-described example.
$^1$H NMR (CDCl$_3$, 400 MHz): δ=1.28 (s, 6H), 1.43 (s, 9H), 7.52-7.55 (m, 2H), 7.7-7.9 (m, 2H), 7.86 (d, 1H, J=9Hz), 8.13 (d, 1H, J=9Hz).

EXAMPLE 60

2-[[7-(4-Cyanophenyl)-2-(trifluoromethyl)benzo[d]thiazol-6-yl]thio]-2-methylpropanoic acid

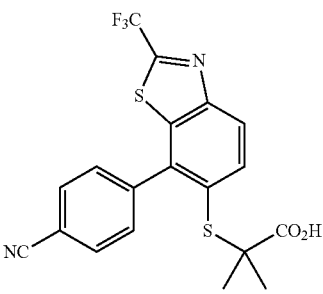 [SMILES: CC(C)(Sc1ccc2nc(C(F)(F)F)sc2c1-c1ccc(C#N)cc1)C(=O)O]

A title compound (white crystal, 193 mg, yield of 87%) was obtained according to the same method as in Example 6 using t-butyl 2-[[7-(4-cyanophenyl)-2-(trifluoromethyl)benzo[d]thiazol-6-yl]thio]-2-methylpropanoate (252 mg, 0.53 mmol) obtained in Example 59.
$^1$H NMR (CD$_3$OD, 400 MHz): δ=1.35 (s, 6H), 7.65 (d, 2H, J=9Hz), 7.89 (d, 2H, J=9Hz), 8.00 (d, 1H, J=9Hz), 8.19 (d, 1H, J=9Hz).

EXAMPLE 61

Ethyl 2-[[7-(4-cyanophenyl)-2-methylbenzo[d]thiazol-6-yl]thio]-2-methylpropanoate

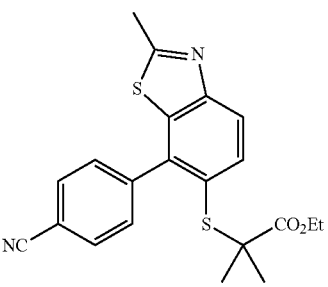 [SMILES: CCOC(=O)C(C)(C)Sc1ccc2nc(C)sc2c1-c1ccc(C#N)cc1]

(1) 7-Bromo-6-methoxy-2-methylbenzo[d]thiazole

A title compound (yellow crystal, 774 mg, yield of 100%) was obtained according to the same method as in Example 25 (1) using 6-metoxy-2-methylbenzo[d]thiazole (540 mg, 3.0 mmol).

¹H NMR (CDCl₃, 400 MHz): δ=3.30 (s, 3H), 4.06 (s, 3H), 7.34 (d, 1H, J=9Hz), 8.39 (d, 1H, J=9Hz).

(2) 4-(6-Methoxy-2-methylbenzo[d]thiazol-7-yl)benzonitrile

A title compound (white crystal, 110 mg, yield of 13%) was obtained according to the same method as in Example 16 (2) using 7-bromo-6-methoxy-2-methlybenzo[d]thiazole (774 mg, 3.0 mmol) obtained in the above-described example and (4-cyanophenyl)boronic acid (440 mg, 3.0 mmol).
¹H NMR (CDCl₃, 400 MHz): δ=2.77 (s, 3H), 3.85 (s, 3H), 7.19 (d, 1H, J=9Hz), 7.67 (d, 2H, J=9Hz), 7.76 (d, 2H, J=9Hz), 7.92 (d, 1H, J=9Hz).

(3) Dimethylcarbamothioic acid O-[7-(4-cyanophenyl)-2-methylbenzo[d]thiadiazol-6-yl]

A title compound (yellow oil material, 730 mg, yield of 87%) was obtained according to the same method as in Examples 18 (2) and 22 (1) using 4-(6-methoxy-2-methylbenzo[d]thiazol-7-yl)benzonitrile (640 mg, 2.28 mmol) obtained in the above-described example.
¹H NMR (CDCl₃, 400 MHz): δ=2.81 (s, 3H), 3.12 (s, 3H), 3.34 (s, 3H), 7.29 (d, 1H, J=9Hz), 7.68 (d, 2H, J=9Hz), 7.75 (d, 2H, J=9Hz), 7.97 (d, 1H, J=9Hz).

(4) Dimethylcarbamothioic acid S-[7-(4-cyanophenyl)-2-methylbenzo[d]thiadiazol-6-yl]

A title compound (yellow crystal, 190 mg, yield of 26%) was obtained according to the same method as in Example 27 (2) using dimethylcarbamothioic acid O-[7-(4-cyanophenyl)-2-methylbenzo[d]thiadiazol-6-yl] (730 mg, 1.98 mmol) obtained in the above-described example.
¹H NMR (CDCl₃, 400 MHz): δ=2.80 (s, 3H), 2.95 (s, 6H), 7.54 (d, 2H, J=9Hz), 7.71 (d, 1H, J=9Hz), 7.74 (d, 2H, J=9Hz), 7.96 (d, 1H, J=9Hz).

(5) Ethyl 2-[[7-(4-cyanophenyl)-2-methylbenzo[d]thiazol-6-yl]thio]-2-methylpropanoate A title compound (white crystal, 68 mg, yield of 33%) was obtained according to the same method as in Examples 22 (3) and 1 (3) using dimethylcarbamothioic acid S-[7-(4-cyanophenyl)-2-methylbenzo[d]thiadiazol-6-yl] (190 mg, 0.51 mmol) obtained in the above-described example.
¹H NMR (CDCl₃, 400 MHz): δ=1.18 (t, 3H, J=7Hz), 1.28 (s, 6H), 2.80 (s, 3H), 4.00 (q, 2H, J=7Hz), 7.55 (d, 2H, J=9Hz), 7.68 (d, 1H, J=9Hz), 7.77 (d, 2H, J=9Hz), 7.90 (d, 1H, J=9Hz).

EXAMPLE 62

2-[[7-(4-Cyanophenyl)-2-methylbenzo[d]thiazol-6-yl]thio]-2-methylpropanoic acid

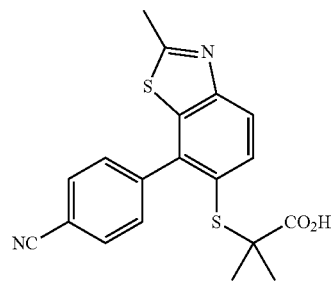 [SMILES: Cc1nc2ccc(SC(C)(C)C(=O)O)c(-c3ccc(C#N)cc3)c2s1]

A title compound (white crystal, 40 mg, yield of 65%) was obtained according to the same method as in Example 26 using ethyl 2-[[7-(4-cyanophenyl)-2-methylbenzo[d]thiazol-6-yl]thio]-2-methylpropanoate (68 mg, 0.17 mmol) obtained in Example 61.
¹H NMR (CDCl₃, 400 MHz): δ=1.31 (s, 6H), 2.85 (s, 3H), 7.58 (d, 2H, J=8Hz), 7.7-7.8 (m, 3H), 7.84 (d, 1H, J=8Hz).

EXAMPLE 63 t-Butyl 2-methyl-2-[[7-[4-(trifluoromethyl)phenyl]benzo[d]thiazol-6-yl]thio]propanoate

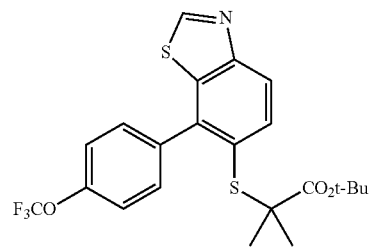 [SMILES: CC(C)(C)OC(=O)C(C)(C)Sc1ccc2ncsc2c1-c1ccc(OC(F)(F)F)cc1]

(1) 6-Methoxy-7-[4-(trifluoromethoxy)phenyl]benzo[d]thiazole

A title compound (yellow crystal, 631 mg, yield of 95%) was obtained according to the same method as in Example 16 (2) using 7-bromo-6-methoxybenzo[d]thiazole (500 mg, 2.05 mmol) and [4-(trifluoromethoxy)phenyl]boronic acid (464 mg, 2.25 mmol).
¹H NMR (CDCl₃, 400 MHz): δ=3.88 (s, 3H), 7.2-7.3 (m, 1H, CDCl₃), 7.33 (d, 2H, J=8Hz), 7.5-7.7 (m, 2H), 8.09 (d, 1H, J=9Hz), 8.83 (s, 1H).

(2) Dimethylcarbamothioic acid O-[7-(4-trifluoromethoxy)phenyl]benzo[d]thiazol-6-yl]

A title compound (colorless oil material, 539 mg, yield of 72%) was obtained according to the same method as in Examples 18 (2) and 22 (1) using 6-methoxy-7-[4-(trifluoromethoxy)phenyl]benzo[d]thiazole (629 mg, 1.98 mmol) obtained in the above-described example.
¹H NMR (CDCl₃, 400 MHz): δ=3.11 (s, 3H), 3.35 (s, 3H), 7.33 (d, 2H, J=8Hz), 7.39 (d, 1H, J=9Hz), 7.6-7.7 (m, 2H), 8.15 (d, 1H, J=9Hz), 8.99 (s, 1H).

(3) Dimethylcarbamothioic acid S-[7-(4-trifluoromethoxy)phenyl]benzo[d]thiazol-6-yl]

A title compound (yellow oil material, 406 mg, yield of 76%) was obtained according to the same method as in Example 27 (2) using dimethylcarbamothioic acid O-[7-(4-trifluoromethoxy)phenyl]benzo[d]thiazol-6-yl] (537 mg, 1.97 mmol) obtained in the above-described example.
¹H NMR (CDCl₃, 400 MHz): δ=2.97 (s, 6H), 7.32 (d, 2H, J=8Hz), 7.4-7.5 (m, 2H), 7.79 (d, 1H, J=8Hz), 8.15 (d, 1H, J=8Hz), 9.03 (s, 1H).

(4) t-Butyl 2-methyl-2-[[7-[4-(trifluoromethoxy)phenyl]benzo[d]thiazol-6-yl]thio]propanoate A title compound (white crystal, 84 mg, yield of 18%) was obtained according to the same method as in Examples 22

(3) and 23 using dimethylcarbamothioic acid S-[7-(4-trifluoromethoxy)phenyl]benzo[d]thiazol-6-yl] (403 mg, 1.01 mmol) obtained in the above-described example.

$^1$H NMR (CDCl$_3$, 400 MHz): δ=1.24 (s, 6H), 1.44 (s, 9H), 7.33 (d, 2H, J=8Hz), 7.4-7.5 (m, 2H), 7.80 (d, 1H, J=8Hz), 8.05 (d, 1H, J=8Hz), 9.01 (s, 1H).

EXAMPLE 64

2-Methyl-2-[[7-[4-(trifluoromethoxy)phenyl]benzo[d]thiazol-6-yl]thio]propanoic acid

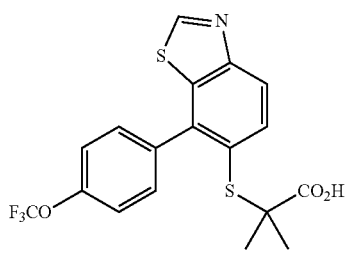 [SMILES: CC(C)(Sc1ccc2ncsc2c1-c1ccc(OC(F)(F)F)cc1)C(=O)O]

A title compound (white crystal, 54 mg, yield of 75%) was obtained according to the same method as in Example 6 using t-butyl 2-methyl-2-[[7-(4-trifluoromethoxy)phenyl]benzo[d]thiazol-6-yl]thio]propanoate (82 mg, 0.18 mmol) obtained in Example 63.

$^1$H NMR (CDCl$_3$, 400 MHz): δ=1.17 (s, 6H), 7.4-7.6 (m, 4H), 7.75 (d, 1H, J=8Hz), 8.05 (d, 1H, J=8Hz), 9.39 (s, 1H).

EXAMPLE 65

Ethyl 1-[[7-(4-cyanophenyl)benzo[d]isothiazol-6-yl]thio]cyclobutan-1-carboxylate

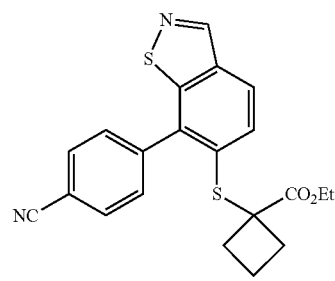 [SMILES: CCOC(=O)C1(Sc2ccc3cnsc3c2-c2ccc(C#N)cc2)CCC1]

A title compound (light yellow oil material, 43 mg, yield of 59%) was obtained according to the same method as in Example 1 (3) using 4-(6-mercaptobenzo[d]isothiazol-7-yl)benzonitrile (50 mg, 0.19 mmol) obtained in Example 27 (3) and ethyl 1-bromocyclobutan-1-carboxylate (45 µL, 0.28 mmol).

$^1$H NMR (CDCl$_3$, 400 MHz): δ=1.16 (t, 3H, J=7Hz), 1.8-2.3 (m, 4H), 2.7-2.9 (m, 2H), 4.0-4.2 (m, 2H), 7.43 (d, 1H, J=9Hz), 7.64 (d, 2H, J=9Hz), 7.83 (d, 2H, J=9Hz), 7.96 (d, 1H, J=9Hz), 8.89 (s, 1H).

EXAMPLE 66

1-[[7-(4-Cyanophenyl)benzo[d]isothiazol-6-yl]thio]cyclobutan-1-carboxylic acid

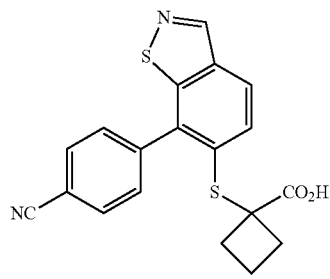 [SMILES: N#Cc1ccc(-c2c(SC3(C(=O)O)CCC3)ccc3cnsc23)cc1]

A title compound (white crystal, 5.2 mg, yield of 13%) was obtained according to the same method as in Example 2 using ethyl 1-[[7-(4-cyanophenyl)benzo[d]isothiazol-6-yl]thio]cyclobutan-1-carboxylate (43 mg, 0.11 mmol) obtained in Example 65.

$^1$H NMR (CDCl$_3$, 400 MHz): δ=1.9-2.3 (m, 4H), 2.7-2.9 (m, 2H), 7.46 (d, 1H, J=9Hz), 7.63 (d, 2H, J=9Hz), 7.81 (d, 2H, J=9Hz), 7.97 (d, 1H, J=9Hz), 8.90 (s, 1H).

EXAMPLE 67

Ethyl 1-[[7-(4-cyanophenyl)benzo[d]isothiazol-6-yl]thio]cyclobutan-1-carboxylate

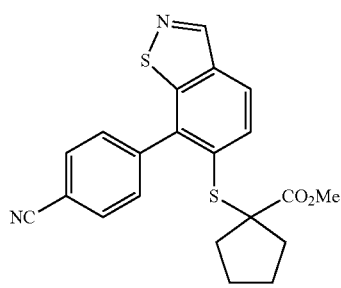 [SMILES: COC(=O)C1(Sc2ccc3cnsc3c2-c2ccc(C#N)cc2)CCCC1]

A title compound (yellow oil material, 42 mg, yield of 100%) was obtained according to the same method as in Example 1 (3) using 4-(6-mercaptobenzo[d]isothiazol-7-yl)benzonitrile (30 mg, 0.11 mmol) obtained in Example 27 (3) and methyl 1-bromocyclopentan-1-carboxylate (46 mg, 0.22 mmol).

$^1$H NMR (CDCl$_3$, 400 MHz): δ=1.5-1.7 (m, 4H), 1.7-1.8 (m, 2H), 2.1-2.3 (m, 2H), 3.65 (s, 3H), 7.5-7.7 (m, 3H), 7.81 (d, 2H, J=9Hz), 7.99 (d, 1H, J=9Hz), 8.93 (s, 1H).

EXAMPLE 68

1-[[7-(4-Cyanophenyl)benzo[d]isothiazol-6-yl]thio]cyclopentan-1-carboxylic acid

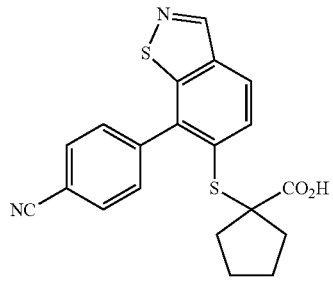 [SMILES: N#Cc1ccc(-c2c(SC3(C(=O)O)CCCC3)ccc3cnsc23)cc1]

A title compound (white crystal, 14 mg, yield of 33%) was obtained according to the same method as in Example 2 using methyl 1-[[7-(4-cyanophenyl)benzo[d]isothiazol-6-yl]thio]cyclopentan-1-carboxylate (42 mg, 0.11 mmol) obtained in Example 67.

$^1$H NMR (CDCl$_3$, 400 MHz): δ=1.5-1.7 (m, 4H), 1.7-1.8 (m, 2H), 2.1-2.3 (m, 2H), 7.61 (d, 2H, J=8Hz), 7.69 (d, 1H, J=8Hz), 7.79 (d, 2H, J=8Hz), 7.99 (d, 1H, J=8Hz), 8.93 (s, 1H).

EXAMPLE 69

Methyl 2-[[7-(4-cyanophenyl)benzo[d]isothiazol-6-yl]thio]-3-methylbutanoate

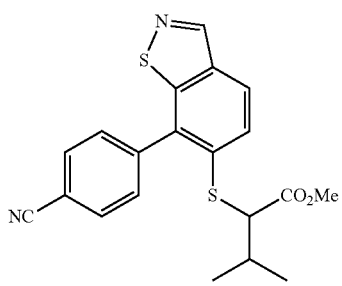 [SMILES: COC(=O)C(Sc1ccc2cnsc2c1-c1ccc(C#N)cc1)C(C)C]

A title compound (light yellow, 42 mg, yield of 100%) was obtained according to the same method as in Example 1 (3) using 4-(6-mercaptobenzo[d]isothiazol-7-yl)benzonitrile (50 mg, 0.19 mmol) obtained in Example 27 (3) and methyl 2-bromo-3-methylbutanoate (49 mg, 0.25 mmol).

$^1$H NMR (CDCl$_3$, 400 MHz): δ=0.92 (d, 3H, J=7Hz), 0.95 (d, 3H, J=7Hz), 1.9-2.1 (m, 1H), 3.37 (d, 1H, J=9Hz), 3.60 (s, 3H), 7.6-7.7 (m, 3H), 7.82 (d, 2H, J=8Hz), 8.00 (d, 1H, J=8Hz), 8.91 (s, 1H).

EXAMPLE 70

2-[[7-(4-Cyanophenyl)benzo[d]isothiazol-6-yl]thio]-3-methylbutanoic acid

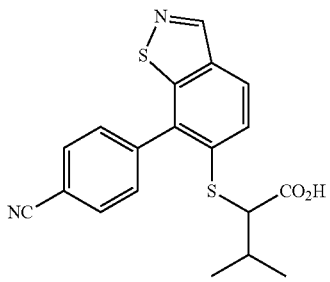 [SMILES: CC(C)C(Sc1ccc2cnsc2c1-c1ccc(C#N)cc1)C(=O)O]

A title compound (light yellow crystal, 10 mg, yield of 25%) was obtained according to the same method as in Example 2 using methyl 2-[[7-(4-cyanophenyl)benzo[d]isothiazol-6-yl]thio]-3-methylbutanoate (42 mg, 0.11 mmol) obtained in Example 69.

$^1$H NMR (CDCl$_3$, 400 MHz): δ=0.97 (d, 3H, J=7Hz), 0.98 (d, 3H, J=7Hz), 1.9-2.1 (m, 1H), 3.36 (d, 1H, J=8Hz), 7.61 (d, 2H, J=8Hz), 7.69 (d, 1H, J=8Hz), 7.79 (d, 2H, J=8Hz), 7.99 (d, 1H, J=8Hz), 8.91 (s, 1H).

EXAMPLE 71

Ethyl 2-methyl-2-[[7-(4-nitrophenyl)benzo[d]isothiazol-6-yl]thio]propanoate

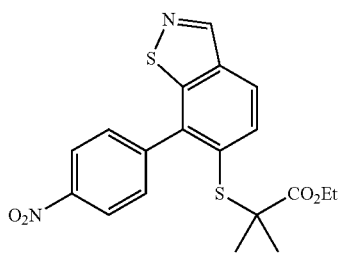 [SMILES: CCOC(=O)C(C)(C)Sc1ccc2cnsc2c1-c1ccc([N+](=O)[O-])cc1]

(1) 6-Methoxy-7-(4-nitrophenyl)benzo[d]isothiazole

A title compound (yellow crystal, 205 mg, yield of 82%) was obtained according to the same method as in Example 16 (2) using 7-bromo-6-methoxybenzo[d]isothiazole (200 mg, 0.82 mmol) and (4-nitrophenyl)boronic acid (163 mg, 0.98 mmol).

$^1$H NMR (CDCl$_3$, 400 MHz): δ=3.95 (s, 3H), 7.26 (d, 1H, J=9Hz), 7.81 (d, 2H, J=9Hz), 8.07 (d, 1H, J=9Hz), 8.36 (d, 2H, J=9Hz), 8.86 (s, 1H).

(2) Dimethylcarbamothioic acid O-[7-(4-nitrophenyl)benzo[d]isothiazol-6-yl]

A title compound (yellow crystal, 170 mg, yield of 72%) was obtained according to the same method as in Examples 18 (2) and 22 (1) using 6-methoxy-7-(4-nitrophenyl)benzo[d]isothiazole (205 mg, 0.72 mmol) obtained in the above-described example.

$^1$H NMR (CDCl$_3$, 400 MHz): δ=3.18 (s, 3H), 3.36 (s, 3H), 7.34 (d, 1H, J=9Hz), 7.83 (d, 2H, J=9Hz), 8.10 (d, 1H, J=9Hz), 8.35 (d, 2H, J=9Hz), 8.96 (s, 1H).

(3) Dimethylcarbamothioic acid S-[7-(4-nitrophenyl)benzo[d]isothiazol-6-yl]

A title compound (yellow oil material, 165 mg, yield of 97%) was obtained according to the same method as in Example 27 (2) using dimethylcarbamothioic acid O-[7-(4-nitrophenyl)benzo[d]isothiazol-6-yl] (170 mg, 0.42 mmol) obtained in the above-described example.

$^1$H NMR (CDCl$_3$, 400 MHz): δ=2.98 (s, 6H), 7.68 (d, 2H, J=9Hz), 7.73 (d, 1H, J=9Hz), 8.09 (d, 1H, J=9Hz), 8.35 (d, 2H, J=9Hz), 8.98 (s, 1H).

(4) Ethyl 2-methyl-2-[[7-(4-nitrophenyl)benzo[d]isothiazol-6-yl]thio]propanoate A title compound (light yellow oil, 100 mg, yield of 54%) was obtained according to the same method as in Examples 22 (3) and 1 (3) using dimethylcarbamothioic acid S-[7-(4-nitrophenyl)benzo[d]isothiazol-6-yl] (165 mg, 0.46 mmol) obtained in the above-described example.

$^1$H NMR (CDCl$_3$, 400 MHz): δ=1.19 (t, 3H, J=7Hz), 1.36 (s, 6H), 4.06 (q, 2H, J=7Hz), 7.6-7.7 (m, 3H), 8.02 (d, 1H, J=9Hz), 8.37 (d, 2H, J=9Hz), 8.96 (s, 1H).

EXAMPLE 72

2-Methyl-2-[[7-(4-nitrophenyl)benzo[d]isothiazol-6-yl]thio]propanoic acid

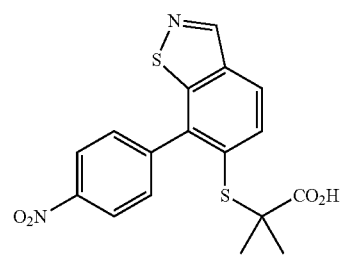 [SMILES: CC(C)(Sc1ccc2cnsc2c1-c1ccc([N+](=O)[O-])cc1)C(=O)O]

A title compound (yellow crystal, 63.5 mg, yield of 68%) was obtained according to the same method as in Example 2 using 2-methyl-2-[[7-(4-nitrophenyl)benzo[d]isothiazol-6-yl]thio]propanoate (100 mg, 0.25 mmol) obtained in Example 71.

$^1$H NMR (DMSO-d$_6$, 400 MHz): δ=1.29 (s, 6H), 7.7-7.9 (m, 3H), 8.26 (d, 1H, J=9Hz), 8.37 (d, 2H, J=9Hz), 9.23 (s, 1H).

EXAMPLE 73 t-Butyl 2-methyl-2-[[7-(p-tolyl)benzo[d]isothiazol-6-yl]thio]propanoate

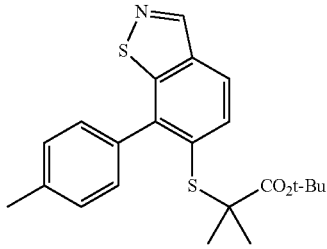 [SMILES: Cc1ccc(-c2c(SC(C)(C)C(=O)OC(C)(C)C)ccc3cnsc23)cc1]

(1) 6-Methoxy-7-(p-tolyl)benzo[d]isothiazole

A title compound (yellow oil material, 232 mg, yield of 111%) was obtained according to the same method as in Example 16 (2) using 7-bromo-6-methoxybenzo[d]isothiazole (200 mg, 0.82 mmol) and p-tolylboronic acid (134 mg, 0.98 mmol).

$^1$H NMR (CDCl$_3$, 400 MHz): δ=2.43 (s, 3H), 3.90 (s, 3H), 7.22 (d, 1H, J=9Hz), 7.30 (d, 2H, J=8Hz), 7.51 (d, 2H, J=8Hz), 7.97 (d, 1H, J=9Hz), 8.82 (s, 1H)

(2) Dimethylcarbamothioic acid O-[7-(p-tolyl)benzo[d]isothiazol-6-yl]

A title compound (brown amorphous, 175 mg, yield of 59%) was obtained according to the same method as in Examples 18 (2) and 22 (1) using 6-methoxy-7-(p-tolyl)benzo[d]isothiazole (230 mg, 0.91 mmol) obtained in the above-described example.

$^1$H NMR (CDCl$_3$, 400 MHz): δ=2.43 (s, 3H), 3.14 (s, 3H), 3.36 (s, 3H), 7.28 (d, 2H, J=8Hz), 7.32 (d, 1H, J=9Hz), 7.49 (d, 2H, J=8Hz), 8.00 (d, 1H, J=9Hz), 8.91 (s, 1H).

(3) Dimethylcarbamothioic acid S-[7-(p-tolyl)benzo[d]isothiazol-6-yl]

A title compound (orange amorphous, 142 mg, yield of 80%) was obtained according to the same method as in Example 27 (2) using dimethylcarbamothioic acid O-[7-(p-tolyl)benzo[d]isothiazol-6-yl] (178 mg, 0.54 mmol) obtained in the above-described example.

$^1$H NMR (CDCl$_3$, 400 MHz): δ=2.44 (s, 3H), 2.98 (s, 6H), 7.28 (d, 2H, J=8Hz), 7.36 (d, 2H, J=8Hz), 7.68 (d, 1H, J=9Hz), 7.98 (d, 1H, J=8Hz), 8.92 (s, 1H).

(4) t-Butyl 2-methyl-2-[[7-(p-tolyl)benzo[d]isothiazol-6-yl]thio]propanoate

A title compound (white crystal, 41 mg, yield of 26%) was obtained according to the same method as in Examples 22 (3) and 23 using dimethylcarbamothioic acid S-[7-(p-tolyl)benzo[d]isothiazol-6-yl] (140 mg, 0.43 mmol) obtained in the above-described example.

$^1$H NMR (CDCl$_3$, 400 MHz): δ=1.31 (s, 6H), 1.45 (s, 9H), 2.45 (s, 3H), 7.30 (d, 2H, J=8Hz), 7.35 (d, 2H, J=8Hz), 7.66 (d, 1H, J=8Hz), 7.91 (d, 1H, J=8Hz), 8.90 (s, 1H).

EXAMPLE 74

2-Methyl-2-[[7-(p-tolyl)benzo[d]isothiazol-6-yl]thio]propanoic acid

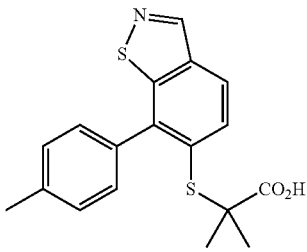 [SMILES: Cc1ccc(-c2c(SC(C)(C)C(=O)O)ccc3cnsc23)cc1]

A title compound (white crystal, 33 mg, yield of 96%) was obtained according to the same method as in Example 6 using t-butyl 2-methyl-2-[[7-(p-tolyl)benzo[d]isothiazol-6-yl]thio]propanoate (40 mg, 0.10 mmol) obtained in Example 73.

$^1$H NMR (CD$_3$OD, 400 MHz): δ=1.32 (s, 6H), 2.45 (s, 3H), 7.32 (s, 4H), 7.75 (d, 1H, J=9Hz), 8.05 (d, 1H, J=9Hz), 8.98 (s, 1H).

EXAMPLE 75 t-Butyl 2-[[7-(4-isopropylphenyl)benzo[d]isothiazol-6-yl]thio]-2-methylpropanoate

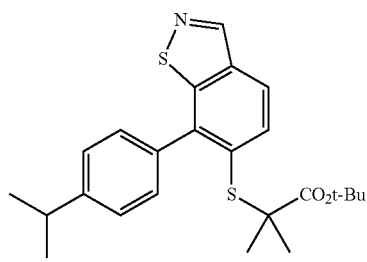 [SMILES: CC(C)c1ccc(-c2c(SC(C)(C)C(=O)OC(C)(C)C)ccc3cnsc23)cc1]

(1) 7-(4-Isopropylphenyl)-6-methoxybenzo[d]isothiazole

A title compound (232 mg, yield of 100%) was obtained according to the same method as in Example 16 (2) using 7-bromo-6-methoxybenzo[d]isothiazole (200 mg, 0.82 mmol) and (4-isopropylphenyl)boronic acid (134 mg, 0.98 mmol).

$^1$H NMR (CDCl$_3$, 400 MHz): δ=1.32 (d, 6H, J=7Hz), 2.9-3.1 (m, 1H), 3.91 (s, 3H), 7.22 (d, 1H, J=9Hz), 7.35 (d, 2H, J=8Hz), 7.56 (d, 2H, J=8Hz), 7.97 (d, 1H, J=8Hz), 8.82 (s, 1H).

(2) Dimethylcarbamothioic acid O-[7-(4-isopropylphenyl)benzo[d]isothiazol-6-yl]

A title compound (175 mg, yield of 51%) was obtained according to the same method as in Examples 18 (2) and 22 (1) using 7-(4-isopropylphenyl)-6-methoxybenzo[d]isothiazole (230 mg, 0.81 mmol) obtained in the above-described example.

$^1$H NMR (CDCl$_3$, 400 MHz): δ=1.31 (d, 6H, J=7Hz), 2.9-3.1 (m, 1H), 3.11 (s, 3H), 3.35 (s, 3H), 7.3-7.4 (m, 3H), 7.52 (d, 2H, J=8Hz), 8.00 (d, 1H, J=8Hz), 8.91 (s, 1H).

(3) Dimethylcarbamothioic acid S-[7-(4-isopropylphenyl)benzo[d]isothiazol-6-yl]

A title compound (55 mg, yield of 48%) was obtained according to the same method as in Example 27 (2) using dimethylcarbamothioic acid O-[7-(4-isopropylphenyl)benzo[d]isothiazol-6-yl] (114 mg, 0.32 mmol) obtained in the above-described example.

$^1$H NMR (CDCl$_3$, 400 MHz): δ=1.32 (d, 6H, J=7Hz), 2.9-3.1 (m, 1H), 2.98 (s, 6H), 7.32 (d, 2H, J=8Hz), 7.39 (d, 2H, J=8Hz), 7.69 (d, 1H, J=8Hz), 7.99 (d, 1H, J=8Hz), 8.92 (s, 1H).

(4) t-Butyl 2-[[7-(4-isopropylphenyl)benzo[d]isothiazol-6-yl]thio]-2-methylpropanoate A title compound (light yellow oil material, 35 mg, yield of 54%) was obtained according to the same method as in Examples 22 (3) and 23 using dimethylcarbamothioic acid S-[7-(4-isopropylphenyl)benzo[d]isothiazol-6-yl] (54 mg, 0.15 mmol) obtained in the above-described example.

$^1$H NMR (CDCl$_3$, 400 MHz): δ=1.31 (s, 6H), 1.33 (d, 6H, J=7Hz), 1.44 (s, 9H), 2.9-3.1 (m, 1H), 7.34 (d, 2H, J=8Hz), 7.39 (d, 2H, J=8Hz), 7.66 (d, 1H, J=8Hz), 7.91 (d, 1H, J=8Hz), 8.90 (s, 1H).

EXAMPLE 76

2-[[7-(4-Isopropylphenyl)benzo[d]isothiazol-6-yl]thio]-2-methylpropanoic acid

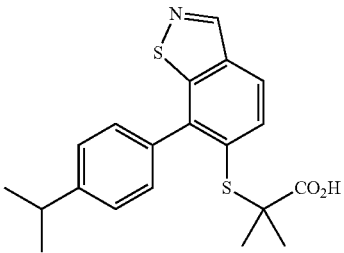 [SMILES: CC(C)c1ccc(-c2c(SC(C)(C)C(=O)O)ccc3cnsc23)cc1]

A title compound (light yellow amorphous, 21 mg, yield of 69%) was obtained according to the same method as in Example 6 using t-butyl 2-[[7-(4-isopropylphenyl)benzo[d]isothiazol-6-yl]thio]-2-methylpropanoate (35 mg, 0.082 mmol) obtained in Example 75.

$^1$H NMR (CDCl$_3$, 400 MHz): δ=1.32 (s, 6H), 1.33 (d, 6H, J=7Hz), 2.9-3.1 (m, 1H), 7.33 (d, 2H, J=8Hz), 7.38 (d, 2H, J=8Hz), 7.70 (d, 11H, J=8Hz), 7.91 (d, 11H, J=8Hz), 8.89 (s, 1H).

EXAMPLE 77 t-Butyl 2-methyl-2-[[7-[4-(trifluoromethyl)phenyl]benzo[d]isothiazol-6-yl]thio]propanoate

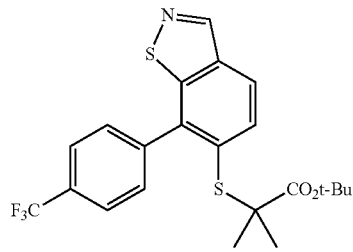

(1) 6-Methoxy-7-[4-(trifluoromethyl)phenyl]benzo[d]isothiazole

A title compound (yellow crystal, 241 mg, yield of 95%) was obtained according to the same method as in Example 16 (2) using 7-bromo-6-methoxybenzo[d]isothiazole (200 mg, 0.82 mmol) and [4-(trifluoromethyl)phenyl]boronic acid (187 mg, 0.98 mmol).
$^1$H NMR (CDCl$_3$, 400 MHz): δ=3.93 (s, 3H), 7.2-7.3 (m, 1H), 7.75 (s, 4H), 8.04 (d, 1H, J=9Hz), 8.85 (s, 1H).

(2) Dimethylcarbamothioic acid O-[7-[4-(trifluoromethyl)phenyl]benzo[d]isothiazol-6-yl]

A title compound (brown crystal, 223 mg, yield of 76%) was obtained according to the same method as in Examples 18 (2) and 22 (1) using 6-methoxy-7-[4-(trifluoromethyl)phenyl]benzo[d]isothiazole (240 mg, 0.78 mmol) obtained in the above-described example.
$^1$H NMR (CDCl$_3$, 400 MHz): δ=3.14 (s, 3H), 3.36 (s, 3H), 7.34 (d, 1H, J=9Hz), 7.75 (s, 4H), 8.07 (d, 1H, J=8Hz), 8.95 (s, 1H).

(3) Dimethylcarbamothioic acid S-[7-[4-(trifluoromethyl)phenyl]benzo[d]isothiazol-6-yl]

A title compound (yellow crystal, 190 mg, yield of 86%) was obtained according to the same method as in Example 27 (2) using dimethylcarbamothioic acid O-[7-[4-(trifluoromethyl)phenyl]benzo[d]isothiazol-6-yl] (221 mg, 0.58 mmol) obtained in the above-described example.
$^1$H NMR (CDCl$_3$, 400 MHz): δ=2.98 (s, 6H), 7.60 (d, 2H, J=8Hz), 7.72 (d, 1H, J=8Hz), 7.75 (d, 2H, J=8Hz), 8.06 (d, 1H, J=8Hz), 8.97 (s, 1H).

(4) t-Butyl 2-methyl-2-[[7-[4-(trifluoromethyl)phenyl]benzo[d]isothiazol-6-yl]thio]propanoate A title compound (colorless oil material, 67 mg, yield of 36%) was obtained according to the same method as in Examples 22 (3) and 23 using dimethylcarbamothioic acid S-[7-[4-(trifluoromethyl)phenyl]benzo[d]isothiazol-6-yl] (188 mg, 0.49 mmol) obtained in the above-described example.
$^1$H NMR (CDCl$_3$, 400 MHz): δ=1.33 (s, 6H), 1.45 (s, 9H), 7.60 (d, 2H, J=8Hz), 7.71 (d, 1H, J=8Hz), 7.77 (d, 2H, J=8Hz), 7.98 (d, 1H, J=9Hz), 8.94 (s, 1H).

EXAMPLE 78

2-Methyl-2-[[7-[4-(trifluoromethyl)phenyl]benzo[d]isothiazol-6-yl]thio]propanoic acid

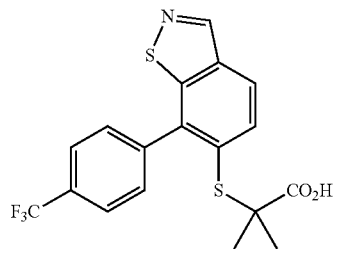 [SMILES: CC(C)(Sc1ccc2cnsc2c1-c1ccc(C(F)(F)F)cc1)C(=O)O]

A title compound (white crystal, 41 mg, yield of 72%) was obtained according to the same method as in Example 6 using t-butyl 2-methyl-2-[[7-[4-(trifluoromethyl)phenyl]benzo[d]isothiazol-6-yl]thio]propanoate (65 mg, 0.14 mmol) obtained in Example 77.
$^1$H NMR (CD$_3$OD, 400 MHz): δ=1.36 (s, 6H), 7.65 (d, 2H, J=8Hz), 7.81-7.83 (m, 3H), 8.13 (d, 1H, J=9Hz), 9.02 (s, 1H).

EXAMPLE 79 t-Butyl 2-methyl-2-[[7-[4-(trifluoromethoxy)phenyl]benzo[d]isothiazol-6-yl]thio]propanoate

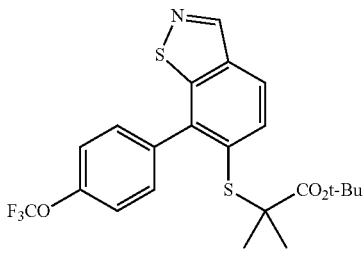 [SMILES: CC(C)(C)OC(=O)C(C)(C)Sc1ccc2cnsc2c1-c1ccc(OC(F)(F)F)cc1]

(1) 6-Methoxy-7-[4-(trifluoromethoxy)phenyl]benzo[d]isothiazole

A title compound (yellow oil material, 233 mg, yield of 87%) was obtained according to the same method as in Example 16 (2) using 7-bromo-6-methoxybenzo[d]isothiazole (200 mg, 0.82 mmol) and [4-(trifluoromethoxy)phenyl]boronic acid (203 mg, 0.98 mmol).
$^1$H NMR (CDCl$_3$, 400 MHz): δ=3.93 (s, 3H), 7.24 (d, 1H, J=9Hz), 7.34 (d, 2H, J=8Hz), 7.6-7.7 (m, 2H), 8.02 (d, 1H, J=9Hz), 8.84 (s, 1H).

(2) Dimethylcarbamothioic acid O-[7-(4-trifluoromethoxy)phenyl]benzo[d]thiazol-6-yl]

A title compound (white crystal, 231 mg, yield of 85%) was obtained according to the same method as in Examples 18 (2) and 22 (1) using 6-methoxy-7-[4-(trifluoromethoxy)phenyl]benzo[d]isothiazole (230 mg, 0.71 mmol) obtained in the above-described example.

¹H NMR (CDCl₃, 400 MHz): δ=3.12 (s, 3H), 3.34 (s, 3H), 7.3-7.4 (m, 3H), 7.63 (d, 2H, J=9Hz), 8.03 (d, 1H, J=9Hz), 8.93 (s, 1H).

(3) Dimethylcarbamothioic acid S-[7-(4-trifluoromethoxy)phenyl]benzo[d]isothiazol-6-yl]

A title compound (white crystal, 201 mg, yield of 88%) was obtained according to the same method as in Example 27 (2) using dimethylcarbamothioic acid O-[7-(4-trifluoromethoxy)phenyl]benzo[d]isothiazol-6-yl] (229 mg, 0.58 mmol) obtained in the above-described example.
¹H NMR (CDCl₃, 400 MHz): δ=2.98 (s, 6H), 7.60 (d, 2H, J=8Hz), 7.7-7.8 (m, 3H), 8.06 (d, 1H, J=8Hz), 8.97 (s, 1H).

(4) t-Butyl 2-methyl-2-[[7-[4-(trifluoromethoxy)phenyl]benzo[d]isothiazol-6-yl]thio]propanoate A title compound (colorless oil material, 36 mg, yield of 17%) was obtained according to the same method as in Examples 22 (3) and 23 using dimethylcarbamothioic acid S-[7-(4-trifluoromethoxy)phenyl]benzo[d]isothiazol-6-yl] (198 mg, 0.50 mmol) obtained in the above-described example.
¹H NMR (CDCl₃, 400 MHz): δ=1.30 (s, 6H), 1.43 (s, 9H), 7.33 (d, 2H, J=8Hz), 7.49 (d, 2H, J=9Hz), 7.70 (d, 1H, J=8Hz), 7.94 (d, 1H, J=8Hz), 8.91 (s, 1H).

EXAMPLE 80

2-Methyl-2-[[7-[4-(trifluoromethoxy)phenyl]benzo[d]isothiazol-6-yl]thio]propanoic acid

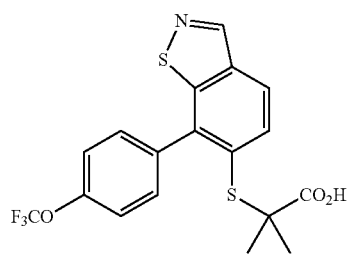 [SMILES: CC(C)(Sc1ccc2cnsc2c1-c1ccc(OC(F)(F)F)cc1)C(=O)O]

A title compound (white crystal, 8 mg, yield of 27%) was obtained according to the same method as in Example 6 using t-butyl 2-methyl-2-[[7-[4-(trifluoromethoxy)phenyl]benzo[d]isothiazol-6-yl]thio]propanoate (34 mg, 0.072 mmol) obtained in Example 79.
¹H NMR (CDCl₃, 400 MHz): δ=1.37 (s, 6H), 7.40 (d, 2H, J=8Hz), 7.55 (d, 2H, J=9Hz), 7.88 (d, 1H, J=9Hz), 8.04 (d, 1H, J=9Hz), 8.94 (s, 1H).

EXAMPLE 81 t-Butyl 2-[[7-(4-chlorophenyl)benzo[d]isothiazol-6-yl]thio]-2-methylpropanoate

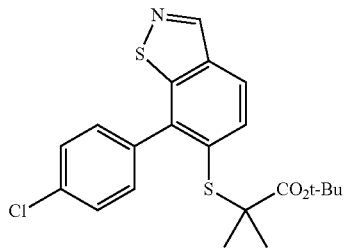 [SMILES: CC(C)(C)OC(=O)C(C)(C)Sc1ccc2cnsc2c1-c1ccc(Cl)cc1]

(1) 7-(4-Chlorophenyl)-6-methoxybenzo[d]isothiazole

A title compound (white crystal, 233 mg, yield of 85%) was obtained according to the same method as in Example 16 (2) using 7-bromo-6-methoxybenzo[d]isothiazole (200 mg, 0.82 mmol) and (4-chlorophenyl)boronic acid (141 mg, 0.98 mmol).
¹H NMR (CDCl₃, 400 MHz): δ=3.09 (s, 3H), 7.21 (d, 1H, J=9Hz), 7.45 (d, 2H, J=9Hz), 7.55 (d, 2H, J=9Hz), 7.99 (d, 1H, J=8Hz), 8.82 (s, 1H).

(2) Dimethylcarbamothioic acid O-[7-(4-chlorophenyl)benzo[d]isothiazol-6-yl]

A title compound (white amorphous, 200 mg, yield of 83%) was obtained according to the same method as in Examples 18 (2) and 22 (1) using 7-(4-chlorophenyl)-6-methoxybenzo[d]isothiazole (220 mg, 0.68 mmol) obtained in the above-described example.
¹H NMR (CDCl₃, 400 MHz): δ=3.15 (s, 3H), 3.36 (s, 3H), 7.31 (d, 1H, J=9Hz), 7.46 (d, 2H, J=9Hz), 7.55 (d, 2H, J=9Hz), 8.03 (d, 1H, J=8Hz), 8.93 (s, 1H).

(3) Dimethylcarbamothioic acid S-[7-(4-chlorophenyl)benzo[d]isothiazol-6-yl]

A title compound (yellow oil material, 138 mg, yield of 70%) was obtained according to the same method as in Example 27 (2) using dimethylcarbamothioic acid O-[7-(4-chlorophenyl)benzo[d]isothiazol-6-yl] (200 mg, 0.57 mmol) obtained in the above-described example.
¹H NMR (CDCl₃, 400 MHz): δ=2.97 (s, 6H), 7.40 (d, 2H, J=9Hz), 7.46 (d, 2H, J=9Hz), 7.69 (d, 1H, J=9Hz), 8.02 (d, 1H, J=8Hz), 8.94 (s, 1H).

(4) t-Butyl 2-[[7-(4-chlorophenyl)benzo[d]isothiazol-6-yl]thio]-2-methylpropanoate A title compound (pale yellow oil material, 30 mg, yield of 18%) was obtained according to the same method as in Examples 22 (3) and 23 using dimethylcarbamothioic acid S-[7-(4-chlorophenyl)benzo[d]isothiazol-6-yl] (138 mg, 0.40 mmol) obtained in the above-described example.
¹H NMR (CDCl₃, 400 MHz): δ=1.31 (s, 6H), 1.44 (s, 9H), 7.40 (d, 2H, J=9Hz), 7.48 (d, 2H, J=9Hz), 7.67 (d, 1H, J=9Hz), 7.94 (d, 1H, J=8Hz), 8.91 (s, 1H).

EXAMPLE 82

2-[[7-(4-Chlorophenyl)benzo[d]isothiazol-6-yl]thio]-2-methylpropanoic acid

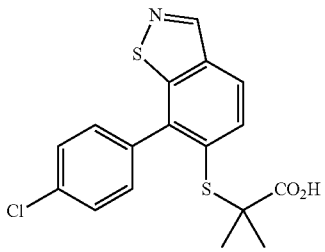 [SMILES: CC(C)(Sc1ccc2cnsc2c1-c1ccc(Cl)cc1)C(=O)O]

A title compound (light yellow crystal, 23 mg, yield of 89%) was obtained according to the same method as in Example 6 using t-butyl 2-[[7-(4-chlorophenyl)benzo[d]isothiazol-6-yl]thio]-2-methylpropanoate (30 mg, 0.071 mmol) obtained in Example 81.

$^1$H NMR (DMSO-$d_6$, 400 MHz): δ=1.28 (s, 6H), 7.46 (d, 2H, J=8Hz), 7.58 (d, 2H, J=8Hz), 7.70 (d, 1H, J=9Hz), 8.20 (d, 1H, J=8Hz), 9.19 (s, 1H).

EXAMPLE 83 t-Butyl 2-[[7-(3-cyanophenyl)benzo[d]isothiazol-6-yl]thio]-2-methylpropanoate

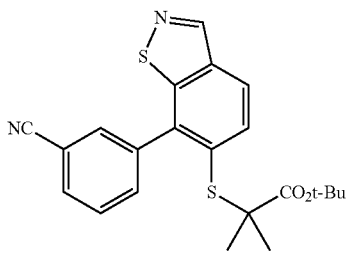 [SMILES: CC(C)(C)OC(=O)C(C)(C)Sc1ccc2cnsc2c1-c1cccc(C#N)c1]

(1) 3-(6-Methoxybenzo[d]isothiazol-7-yl)benzonitrile

A title compound (white crystal, 182 mg, yield of 83%) was obtained according to the same method as in Example 16 (2) using 7-bromo-6-methoxybenzo[d]isothiazole (200 mg, 0.82 mmol) and (3-cyanophenyl)boronic acid (145 mg, 0.98 mmol).

$^1$H NMR (CDCl$_3$, 400 MHz): δ=3.94 (s, 3H), 7.2-7.3 (m, 1H), 7.61 (t, 1H, J=8Hz), 7.70 (dt, 1H, J=1Hz, 8Hz), 7.87 (dt, 1H, J=1Hz, 8Hz), 7.92 (t, 1H, J=1Hz), 8.05 (d, 1H, J=9Hz), 8.85 (s, 1H).

(2) Dimethylcarbamothioic acid O-[7-(3-cyanophenyl)benzo[d]isothiazol-6-yl]

A title compound (brown crystal, 179 mg, yield of 82%) was obtained according to the same method as in Examples 18 (2) and 22 (1) using 3-(6-methoxybenzo[d]isothiazol-7-yl)benzonitrile (180 mg, 0.68 mmol) obtained in the above-described example.

$^1$H NMR (CDCl$_3$, 400 MHz): δ=3.18 (s, 3H), 3.35 (s, 3H), 7.33 (d, 1H, J=9Hz), 7.62 (t, 1H, J=8Hz), 7.7-7.8 (m, 1H), 7.8-8.0 (m, 2H), 8.08 (d, 1H, J=9Hz), 8.95 (s, 1H).

(3) Dimethylcarbamothioic acid S-[7-(3-cyanophenyl)benzo[d]isothiazol-6-yl]

A title compound (orange amorphous, 162 mg, yield of 91%) was obtained according to the same method as in Example 27 (2) using dimethylcarbamothioic acid O-[7-(3-cyanophenyl)benzo[d]isothiazol-6-yl] (178 mg, 0.52 mmol) obtained in the above-described example.

$^1$H NMR (CDCl$_3$, 400 MHz): δ=2.98 (s, 6H), 7.62 (t, 1H, J=8Hz), 7.7-7.8 (m, 4H), 8.08 (d, 1H, J=8Hz), 8.97 (s, 1H).

(4) t-Butyl 2-[[7-(3-cyanophenyl)benzo[d]isothiazol-6-yl]thio]-2-methyl propanoate A title compound (colorless oil material, 37 mg, yield of 22%) was obtained according to the same method as in Examples 22 (3) and 23 using dimethylcarbamothioic acid S-[7-(3-cyanophenyl)benzo[d]isothiazol-6-yl] (160 mg, 0.47 mmol) obtained in the above-described example.

$^1$H NMR (CDCl$_3$, 400 MHz): δ=1.32 (s, 6H), 1.44 (s, 9H), 7.63 (t, 1H, J=8Hz), 7.6-7.8 (m, 4H), 7.99 (d, 1H, J=9Hz), 8.93 (s, 1H).

EXAMPLE 84

2-[[7-(3-Cyanophenyl)benzo[d]isothiazol-6-yl]thio]-2-methylpropanoic acid

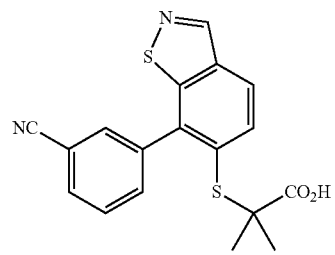 [SMILES: CC(C)(Sc1ccc2cnsc2c1-c1cccc(C#N)c1)C(=O)O]

A title compound (white crystal, 8 mg, yield of 26%) was obtained according to the same method as in Example 6 using t-butyl 2-[[7-(3-cyanophenyl)benzo[d]isothiazol-6-yl]thio]-2-methylpropanoate (36 mg, 0.088 mmol) obtained in Example 83.

$^1$H NMR (CD$_3$OD, 400 MHz): δ=1.38 (s, 6H), 7.7-7.8 (m, 4H), 7.90 (d, 1H, J=9Hz), 8.09 (d, 1H, J=8Hz), 8.97 (s, 1H).

EXAMPLE 85

Ethyl 2-[[7-(4-cyano-2-methylphenyl)benzo[d]isothiazol-6-yl]thio]-2-methylpropanoate

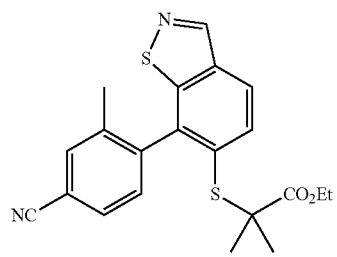 [SMILES: CCOC(=O)C(C)(C)Sc1ccc2cnsc2c1-c1ccc(C#N)cc1C]

(1) 4-(6-Methoxybenzo[d]isothiazol-7-yl)-3-methyl-benzonitrile

A title compound (white crystal, 129 mg, yield of 56%) was obtained according to the same method as in Example 16 (2) using 7-bromo-6-methoxybenzo[d]isothiazole (200 mg, 0.82 mmol) and (4-cyano-2-methylphenyl)boronic acid (158 mg, 0.98 mmol).

$^1$H NMR (CDCl$_3$, 400 MHz): δ=2.12 (s, 3H), 3.88 (s, 3H), 7.22 (d, 1H, J=9Hz), 7.39 (d, 1H, J=8Hz), 7.57 (d, 1H, J=8Hz), 7.63 (s, 1H), 8.06 (d, 1H, J=9Hz), 8.84 (s, 1H).

(2) Dimethylcarbamothioic acid S-[7-(4-cyano-2-methylphenyl)benzo[d]isothiazol-6-yl]

A crude material (yellow oil material, 219 mg) of dimethylcarbamothioic acid O-[7-(4-cyano-2-methylphenyl)benzo[d]isothiazol-6-yl] was obtained according to the same method as in Examples 18 (2) and 22 (1) using 4-(6-methoxybenzo[d]isothiazol-7-yl)-3-methylbenzonitrile (129 mg, 0.46 mmol) obtained in the above-described example.

A title compound (colorless oil material, 132 mg, yield of 81%) was obtained according to the same method as in Example 27 (2) using the obtained crude material (219 mg) of dimethylcarbamothioic acid O-[7-(4-cyano-2-methylphenyl)benzo[d]isothiazol-6-yl].

$^1$H NMR (CDCl$_3$, 400 MHz): δ=2.04 (s, 3H), 2.92 (s, 6H), 7.33 (d, 1H, J=9Hz), 7.56 (d, 1H, J=8Hz), 7.62 (s, 1H), 7.69 (d, 1H, J=9Hz), 8.06 (d, 1H, J=8Hz), 8.95 (s, 1H).

(3) Ethyl 2-[[7-(4-cyano-2-methylphenyl)benzo[d]isothiazol-6-yl]thio]-2-methylpropanoate A title compound (colorless oil material, 25 mg, yield of 17%) was obtained according to the same methods as in Examples 22 (3) and 1 (3) using dimethylcarbamothioic acid S-[7-(4-cyano-2-methylphenyl)benzo[d]isothiazol-6-yl] (132 mg, 0.37 mmol) obtained in the above-described example.

$^1$H NMR (CDCl$_3$, 400 MHz): δ=1.26 (t, 3H, J=7Hz), 2.05 (s, 3H), 4.0-4.3 (m, 2H), 7.31 (d, 1H, J=8Hz), 7.5-7.7 (m, 3H), 7.99 (d, 1H, J=8Hz), 8.92 (s, 1H).

EXAMPLE 86

2-[[7-(4-Cyano-2-methylphenyl)benzo[d]isothiazol-6-yl]thio]-2-methylpropanoic acid

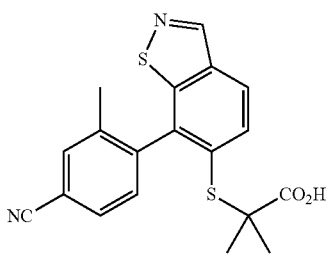 [SMILES: Cc1cc(C#N)ccc1-c1c(SC(C)(C)C(=O)O)ccc2cnsc12]

A title compound (white crystal, 9.7 mg, yield of 42%) was obtained according to the same method as in Example 2 using ethyl 2-[[7-(4-cyano-2-methylphenyl)benzo[d]isothiazol-6-yl]thio]-2-methylpropanoate (25 mg, 0.063 mmol) obtained in Example 85.

$^1$H NMR (CDCl$_3$, 400 MHz): δ=1.40 (s, 3H), 1.48 (s, 3H), 2.05 (s, 3H), 7.31 (d, 1H, J=8Hz), 7.56 (d, 1H, J=8Hz), 7.63 (s, 1H), 7.67 (d, 1H, J=8Hz), 7.99 (d, 1H, J=8Hz), 8.92 (s, 1H).

EXAMPLE 87 t-Butyl 2-[[7-(4-cyano-3-methylphenyl)benzo[d]isothiazol-6-yl]thio]-2-methylpropanoate

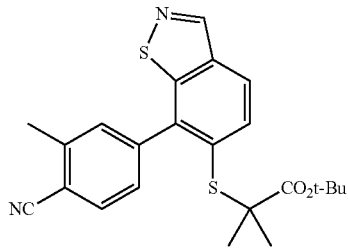 [SMILES: Cc1cc(-c2c(SC(C)(C)C(=O)OC(C)(C)C)ccc3cnsc23)ccc1C#N]

(1) 4-(6-Methoxybenzo[d]isothiazol-7-yl)-2-methyl-benzonitrile

A title compound (white crystal, 190 mg, yield of 56%) was obtained according to the same method as in Example 16 (2) using 7-bromo-6-methoxybenzo[d]isothiazole (200 mg, 0.82 mmol) and (4-cyano-3-methylphenyl)boronic acid (198 mg, 1.23 mmol).

$^1$H NMR (CDCl$_3$, 400 MHz): δ=2.64 (s, 3H), 3.94 (s, 3H), 7.25 (d, 1H, J=9Hz), 7.54 (d, 1H, J=9Hz), 7.59 (s, 1H), 7.73 (d, 1H, J=9Hz), 8.05 (d, 1H, J=9Hz), 8.85 (s, 1H).

(2) Dimethylcarbamothioic acid O-[7-(4-cyano-3-methylphenyl)benzo[d]isothiazol-6-yl]

A title compound (white amorphous, 160 mg, yield of 67%) was obtained according to the same method as in Examples 18 (2) and 22 (1) using 4-(6-methoxybenzo[d]isothiazol-7-yl)-2-methylbenzonitrile (190 mg, 0.68 mmol) obtained in the above-described example.

$^1$H NMR (CDCl$_3$, 400 MHz): δ=2.62 (s, 3H), 3.17 (s, 3H), 3.36 (s, 3H), 7.32 (d, 1H, J=9Hz), 7.54 (d, 1H, J=9Hz), 7.61 (s, 1H), 7.72 (d, 1H, J=9Hz), 8.07 (d, 1H, J=9Hz), 8.94 (s, 1H).

(3) Dimethylcarbamothioic acid O-[7-(4-cyano-3-methylphenyl)benzo[d]isothiazol-6-yl]

A title compound (light yellow oil material, 159 mg, yield of 99%) was obtained according to the same method as in Example 27 (2) using dimethylcarbamothioic acid O-[7-(4-cyano-3-methylphenyl)benzo[d]isothiazol-6-yl] (160 mg, 0.45 mmol) obtained in the above-described example.

$^1$H NMR (CDCl$_3$, 400 MHz): δ=2.62 (s, 3H), 2.99 (s, 6H), 7.39 (d, 1H, J=8Hz), 7.45 (s, 1H), 7.6-7.8 (m, 2H), 8.06 (d, 1H, J=8Hz), 8.96 (s, 1H).

(4) t-Butyl 2-[[7-(4-cyano-3-methylphenyl)benzo[d]isothiazol-6-yl]thio]-2-methylpropanoate A title compound (light yellow oil material, 110 mg, yield of 58%) was obtained according to the same method as in Examples 22 (3) and 23 using dimethylcarbamothioic acid S-[7-(4-cyano-3-methylphenyl)benzo[d]isothiazol-6-yl] (159 mg, 0.45 mmol) obtained in the above-described example.

$^1$H NMR (CDCl$_3$, 400 MHz): δ=1.33 (s, 6H), 1.44 (s, 9H), 2.64 (s, 3H), 7.39 (d, 1H, J=8Hz), 7.43 (s, 1H), 7.69 (d, 1H, J=8Hz), 7.74 (d, 1H, J=8Hz), 7.98 (d, 1H, J=8Hz), 8.93 (s, 1H).

EXAMPLE 88

2-[[7-(4-Cyano-3-methylphenyl)benzo[d]isothiazol-6-yl]thio]-2-methylpropanoic acid

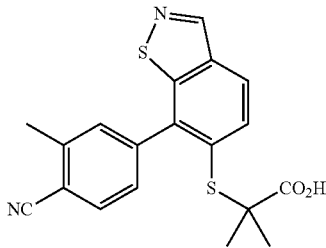

A title compound (white crystal, 40 mg, yield of 42%) was obtained according to the same method as in Example 6 using t-butyl 2-[[7-(4-cyano-3-methylphenyl)benzo[d]isothiazol-6-yl]thio]-2-methylpropanoate (110 mg, 0.26 mmol) obtained in Example 87.

$^1$H NMR (DMSO-d$_6$, 400 MHz): δ=1.31 (s, 6H), 2.64 (s, 3H), 7.47 (d, 1H, J=8Hz), 7.57 (s, 1H), 7.73 (d, 1H, J=8Hz), 7.93 (d, 1H, J=8Hz), 8.25 (d, 1H, J=8Hz), 9.22 (s, 1H).

EXAMPLE 89 t-Butyl 2-[[7-(4-cyano-3-fluorophenyl)benzo[d]isothiazol-6-yl]thio]-2-methylpropanoate

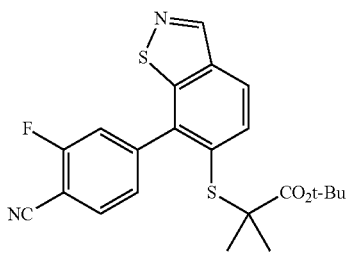

(1) 2-Fluoro-4-(6-methoxybenzo[d]isothiazol-7-yl)benzonitrile

A title compound (light yellow crystal, 194 mg, yield of 78%) was obtained according to the same method as in Example 16 (2) using 7-bromo-6-methoxybenzo[d]isothiazole (200 mg, 0.82 mmol) and (4-cyano-3-fluorophenyl)boronic acid (162 mg, 0.98 mmol).

$^1$H NMR (CDCl$_3$, 400 MHz): δ=3.95 (s, 3H), 7.25 (d, 1H, J=9Hz), 7.5-7.6 (m, 2H), 7.75 (dd, 1H, J=7Hz, 8Hz), 8.08 (d, 1H, J=9Hz), 8.86 (s, 1H).

(2) Dimethylcarbamothioic acid O-[7-(4-cyano-3-fluorophenyl)benzo[d]isothiazol-6-yl]

A title compound (yellow amorphous, 191 mg, yield of 86%) was obtained according to the same method as in Examples 18 (2) and 22 (1) using 2-fluoro-4-(6-methoxybenzo[d]isothiazol-7-yl)benzonitrile (194 mg, 0.64 mmol) obtained in the above-described example.

$^1$H NMR (CDCl$_3$, 400 MHz): δ=3.22 (s, 3H), 3.38 (s, 3H), 7.32 (d, 1H, J=8Hz), 7.5-7.6 (m, 2H), 7.78 (t, 1H, J=7Hz), 8.11 (d, 1H, J=8Hz), 8.96 (s, 1H).

(3) Dimethylcarbamothioic acid S-[7-(4-cyano-3-fluorophenyl)benzo[d]isothiazol-6-yl]

A title compound (orange amorphous, 150 mg, yield of 79%) was obtained according to the same method as in Example 27 (2) using dimethylcarbamothioic acid O-[7-(4-cyano-3-fluorophenyl)benzo[d]isothiazol-6-yl] (191 mg, 0.53 mmol) obtained in the above-described example.

$^1$H NMR (CDCl$_3$, 400 MHz): δ=2.98 (s, 6H), 7.3-7.5 (m, 2H), 7.71 (d, 1H, J=8Hz), 7.76 (t, 1H, J=7Hz), 8.08 (d, 1H, J=8Hz), 8.97 (s, 1H).

(4) t-Butyl 2-[[7-(4-cyano-3-fluorophenyl)benzo[d]isothiazol-6-yl]thio]-2-methylpropanoate A title compound (light yellow oil material, 100 mg, yield of 56%) was obtained according to the same method as in Examples 22 (3) and 23 using dimethylcarbamothioic acid S-[7-(4-cyano-3-fluorophenyl)benzo[d]isothiazol-6-yl] (150 mg, 0.45 mmol) obtained in the above-described example.

$^1$H NMR (CDCl$_3$, 400 MHz): δ=1.33 (s, 6H), 1.44 (s, 9H), 7.3-7.5 (m, 2H), 7.70 (d, 1H, J=8Hz), 7.7-7.8 (m, 1H), 8.02 (d, 1H, J=8Hz), 8.94 (s, 1H).

EXAMPLE 90

2-[[7-(4-Cyano-3-fluorophenyl)benzo[d]isothiazol-6-yl]thio]-2-methylpropanoic acid

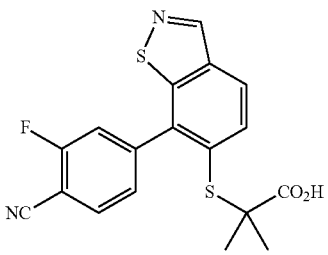 [SMILES: Cc1cc(-c2c(SC(C)(C)C(=O)O)ccc3cnsc23)ccc1C#N]

A title compound (white crystal, 6.5 mg, yield of 8%) was obtained according to the same method as in Example 6 using t-butyl 2-[[7-(4-cyano-3-methylphenyl)benzo[d]isothiazol-6-yl]thio]-2-methylpropanoate (100 mg, 0.23 mmol) obtained in Example 89.

$^1$H NMR (DMSO-d$_6$, 400 MHz): δ=1.31 (s, 6H), 7.55 (dd, 1H, J=2Hz, 8Hz), 7.7-7.8 (m, 2H), 8.11 (t, 1H, J=8Hz), 8.29 (d, 1H, J=8Hz), 9.25 (s, 1H).

EXAMPLE 91 t-Butyl 2-[[7-(4-fluoronaphthalen-1-yl)benzo[d]isothiazol-6-yl]thio]-2-methylpropanoate

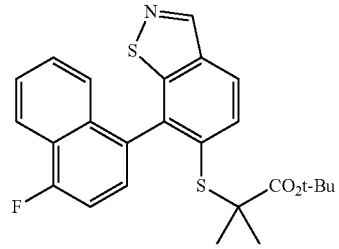 [SMILES: CC(C)(C)OC(=O)C(C)(C)Sc1ccc2cnsc2c1-c1ccc(F)c2ccccc12]

(1) 7-(4-Fluoronaphthalen-1-yl)-6-methoxybenzo[d]isothiazole

A title compound (orange oil material, 219 mg, yield of 86%) was obtained according to the same method as in Example 16 (2) using 7-bromo-6-methoxybenzo[d]isothiazole (200 mg, 0.82 mmol) and (4-fluoronaphthalen-1-yl)boronic acid (187 mg, 0.98 mmol).

$^1$H NMR (CDCl$_3$, 400 MHz): δ=3.81 (s, 3H), 7.2-7.3 (m, 2H), 7.41 (d, 2H, J=4Hz), 7.4-7.6 (m, 2H), 8.10 (d, 1H, J=9Hz), 8.20 (d, 1H, J=8Hz), 8.87 (s, 1H).

(2) Dimethylcarbamothioic acid O-[7-(4-fluoronaphthalen-1-yl)benzo[d]isothiazol-6-yl]

A title compound (pale brown amorphous, 220 mg, yield of 81%) was obtained according to the same method as in Examples 18 (2) and 22 (1) using 7-(4-fluoronaphthalen-1-yl)-6-methoxybenzo[d]isothiazole (219 mg, 0.71 mmol) obtained in the above-described example.

$^1$H NMR (CDCl$_3$, 400 MHz): δ=2.60 (s, 3H), 3.13 (s, 3H), 7.2-7.3 (m, 1H), 7.4-7.5 (m, 2H), 7.5-7.6 (m, 3H), 8.14 (d, 1H, J=9Hz), 8.20 (d, 1H, J=8Hz), 8.97 (s, 1H).

(3) Dimethylcarbamothioic acid S-[7-(4-fluoronaphthalen-1-yl)benzo[d]isothiazol-6-yl]

A title compound (pale brown amorphous, 135 mg, yield of 61%) was obtained according to the same method as in Example 27 (2) using dimethylcarbamothioic acid O-[7-(4-fluoronaphthalen-1-yl)benzo[d]isothiazol-6-yl] (220 mg, 0.58 mmol) obtained in the above-described example.

$^1$H NMR (CDCl$_3$, 400 MHz): δ=2.77 (s, 3H), 2.90 (s, 3H), 7.2-7.3 (m, 1H), 7.31 (d, 1H, J=8Hz), 7.3-7.5 (m, 2H), 7.57 (d, 1H, J=8Hz), 7.80 (d, 1H, J=9Hz), 8.14 (d, 1H, J=9Hz), 8.21 (d, 1H, J=8Hz), 8.98 (s, 1H).

(4) t-Butyl 2-[[7-(4-fluoronaphthalen-1-yl)benzo[d]isothiazol-6-yl]thio]-2-methylpropanoate A title compound (light yellow oil material, 61 mg, yield of 38%) was obtained according to the same method as in Examples 22 (3) and 23 using dimethylcarbamothioic acid S-[7-(4-fluoronaphthalen-1-yl)benzo[d]isothiazol-6-yl] (135 mg, 0.35 mmol) obtained in the above-described example.

$^1$H NMR (CDCl$_3$, 400 MHz): δ=1.32 (s, 6H), 1.47 (s, 9H), 7.2-7.3 (m, 2H), 7.3-7.5 (m, 2H), 7.57 (t, 1H, J=8Hz), 7.71 (d, 1H, J=9Hz), 8.04 (d, 1H, J=9Hz), 8.22 (d, 1H, J=8Hz), 8.93 (s, 1H).

EXAMPLE 92

2-[[7-(4-Fluoronaphthalen-1-yl)benzo[d]isothiazol-6-yl]thio]-2-methylpropanoic acid

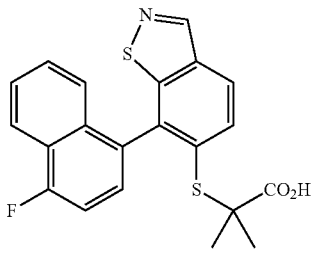 [SMILES: CC(C)(Sc1ccc2cnsc2c1-c1ccc(F)c2ccccc12)C(=O)O]

A title compound (white crystal, 20 mg, yield of 39%) was obtained according to the same method as in Example 6 using t-butyl 2-[[7-(4-fluoronaphthalen-1-yl)benzo[d]isothiazol-6-yl]thio]-2-methylpropanoate (61 mg, 0.13 mmol) obtained in Example 91.

$^1$H NMR (DMSO-d$_6$, 400 MHz): δ=1.26 (s, 3H), 1.29 (s, 3H), 7.15 (d, 1H, J=9Hz), 7.4-7.6 (m, 3H), 7.68 (t, 1H, J=7Hz), 7.85 (d, 1H, J=8Hz), 8.18 (d, 1H, J=8Hz), 8.29 (d, 1H, J=8Hz), 8.20 (s, 1H).

EXAMPLE 93 t-Butyl 2-[[7-(4-cyanonaphthalen-1-yl)benzo[d]isothiazol-6-yl]thio]-2-methylpropanoate

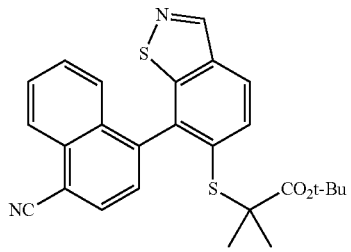 [SMILES: CC(C)(C)OC(=O)C(C)(C)Sc1ccc2cnsc2c1-c1ccc(C#N)c2ccccc12]

(1) Methyl 4-(6-methoxybenzo[d]isothiazol-7-yl)-1-naphthoate

A title compound (white amorphous, 373 mg, yield of 65%) was obtained according to the same method as in Example 16 (2) using 7-bromo-6-methoxybenzo[d]isothiazole (400 mg, 1.6 mmol) and [4-(methoxycarbonyl)naphthalen-1-yl]boronic acid (452 mg, 2.0 mmol).

$^1$H NMR (CDCl$_3$, 400 MHz): δ=3.81 (s, 3H), 4.05 (s, 3H), 7.30 (d, 1H, J=9Hz), 7.41 (t, 1H, J=1Hz, 7Hz), 7.49 (d, 1H, J=8Hz), 7.59 (d, 1H, J=7Hz), 7.63 (t, 1H, J=1Hz, 7Hz), 8.14 (d, 1H, J=9Hz), 8.27 (d, 1H, J=8Hz), 8.88 (s, 1H), 8.99 (d, 1H, J=9Hz).

(2) 4-(6-Methoxybenzo[d]isothiazol-7-yl)-1-naphthonitrile

A crude material of 4-(6-methoxybenzo[d]isothiazol-7-yl)-1-naphthoic acid was obtained according to the same method as in Example 2 using methyl 4-(6-methoxybenzo[d]isothiazol-7-yl)-1-naphthoate (372 mg, 1.07 mmol) obtained in the above-described example.

The obtained crude material was dissolved in toluene (5 mL), thionyl chloride (117 μL, 1.6 mmol) was added thereto, and the solution was stirred at room temperature. After 1 hour, the reaction solution was concentrated, the obtained crude material was dissolved in chloroform (5 mL), and a $NH_3$—$CHCl_3$ solution (filtrate obtained by extracting 2 M $NH_3$ aqueous solution (10 mL) using $CHCl_3$ (10 mL), drying the resultant over sodium sulfate, and filtering the resultant) was added thereto. The precipitated crystals were separated by filtration, and the obtained crystals were washed with hexane (5 mL) to obtain a crude material of 4-(6-methoxybenzo[d]isothiazol-7-yl)-1-naphthamide.

The obtained crude material was dissolved in acetonitrile (8 mL), dimethylformamide (160 μL) was added thereto, and oxalyl chloride (205 μL, 2.39 mmol) was added thereto at −15° C. under a nitrogen stream. After 30 minutes, pyridine (400 μL) was added thereto. After 30 minutes, saturated ammonium chloride aqueous solution was added to the reaction solution, and extraction was carried out using ethyl acetate/hexane (1/1 solution, 20 mL). The organic layer was dried over sodium sulfate and filtered, and then the solvent was distilled off under reduced pressure. The obtained residue was purified by silica gel column chromatography (ethyl acetate:hexane=1:2) to obtain a title compound (white crystal, 211 mg, yield of 62%).

$^1$H NMR (CDCl$_3$, 400 MHz): δ=3.83 (s, 3H), 7.31 (d, 1H, J=9Hz), 7.4-7.6 (m, 2H), 7.62 (d, 1H, J=7Hz), 7.73 (dt, 1H, J=2Hz, 7Hz), 8.04 (d, 1H, J=7Hz), 8.16 (d, 1H, J=9Hz), 8.36 (d, 1H, J=9Hz), 8.89 (s, 1H).

(3) Dimethylcarbamothioic acid O-[7-(4-cyanonaphthalen-1-yl)benzo[d]isothiazol-6-yl]

A title compound (yellow oil material, 271 mg, yield of 100%) was obtained according to the same method as in Examples 18 (2) and 22 (1) using 4-(6-methoxybenzo[d]isothiazol-7-yl)-1-naphthonitrile (210 mg, 0.70 mmol) obtained in the above-described example.

$^1$H NMR (CDCl$_3$, 400 MHz): δ=2.63 (s, 3H), 3.14 (s, 3H), 7.43 (d, 1H, J=8Hz), 7.53 (dt, 1H, J=1Hz, 7Hz), 7.66 (d, 1H, J=9Hz), 7.7-7.8 (m, 2H), 8.01 (d, 1H, J=8Hz), 8.18 (d, 1H, J=9Hz), 8.35 (d, 1H, J=8Hz), 8.98 (s, 1H).

(4) Dimethylcarbamothioic acid S-[7-(4-cyanonaphthalen-1-yl)benzo[d]isothiazol-6-yl]

A title compound (white amorphous, 135 mg, yield of 50%) was obtained according to the same method as in Example 27 (2) using dimethylcarbamothioic acid O-[7-(4-cyanonaphthalen-1-yl)benzo[d]isothiazol-6-yl] (271 mg, 0.70 mmol) obtained in the above-described example.

$^1$H NMR (CDCl$_3$, 400 MHz): δ=2.7-2.9 (m, 6H), 7.41 (d, 1H, J=8Hz), 7.47 (dt, 1H, J=1Hz, 7Hz), 7.57 (d, 1H, J=7Hz), 7.71 (dt, 1H, J 1=1Hz, 7Hz), 7.80 (d, 1H, J=8Hz), 8.01 (d, 1H, J=7Hz), 8.17 (d, 1H, J=8Hz), 8.35 (d, 1H, J=9Hz), 8.99 (s, 1H).

(5) t-Butyl 2-[[7-(4-cyanonaphthalen-1-yl)benzo[d]isothiazol-6-yl]thio]-2-methylpropanoate A title compound (white amorphous, 86 mg, yield of 54%) was obtained according to the same method as in Examples 22 (3) and 23 using dimethylcarbamothioic acid S-[7-(4-cyanonaphthalen-1-yl)benzo[d]isothiazol-6-yl] (133 mg, 0.34 mmol) obtained in the above-described example.

$^1$H NMR (CDCl$_3$, 400 MHz): δ=1.28 (s, 3H), 1.31 (s, 3H), 1.47 (s, 9H), 7.36 (d, 1H, J=8Hz), 7.49 (d, 1H, J=8Hz), 7.54 (d, 1H, J=7Hz), 7.7-7.6 (m, 2H), 8.05 (d, 1H, J=7Hz), 8.09 (d, 1H, J=9Hz), 8.38 (d, 1H, J=9Hz), 8.95 (s, 1H).

EXAMPLE 94

2-[[7-(4-Cyanonaphthalen-1-yl)benzo[d]isothiazol-6-yl]thio]-2-methylpropanoic acid

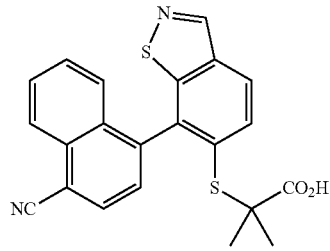 [SMILES: CC(C)(Sc1ccc2cnsc2c1-c1ccc(C#N)c2ccccc12)C(=O)O]

A title compound (white crystal, 49 mg, yield of 68%) was obtained according to the same method as in Example 6 using t-butyl 2-[[7-(4-cyanonaphthalen-1-yl)benzo[d]isothiazol-6-yl]thio]-2-methylpropanoate (82 mg, 0.18 mmol) obtained in Example 93.

$^1$H NMR (CDCl$_3$, 400 MHz): δ=1.36 (s, 3H), 1.40 (s, 3H), 7.35 (d, 1H, J=8Hz), 7.51 (d, 1H, J=7Hz), 7.56 (d, 1H, J=7Hz), 7.7-7.8 (m, 2H), 8.04 (d, 1H, J=7Hz), 8.12 (d, 1H, J=9Hz), 8.38 (d, 1H, J=9Hz), 8.98 (s, 1H).

EXAMPLE 95 t-Butyl 2-methyl-2-[[7-(pyridin-3-yl)benzo[d]isothiazol-6-yl]thio]propanoate

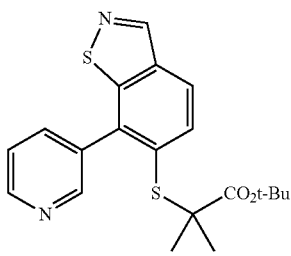 [SMILES: CC(C)(C)OC(=O)C(C)(C)Sc1ccc2cnsc2c1-c1cccnc1]

(1) 6-Methoxy-7-(pyridin-3-yl)benzo[d]isothiazole

A title compound (yellow crystal, 250 mg, yield of 63%) was obtained according to the same method as in Example 16 (2) using 7-bromo-6-methoxybenzo[d]isothiazole (400 mg, 1.6 mmol) and pyridin-3-ylboronic acid (242 mg, 1.96 mmol).

$^1$H NMR (CDCl$_3$, 400 MHz): δ=3.89 (s, 3H), 7.21 (d, 1H, J=9Hz), 7.27 (dd, 1H, J=5Hz, 8Hz), 7.90 (d, 1H, J=8Hz), 8.00 (d, 1H, J=9Hz), 8.61 (d, 1H, J=5Hz), 8.81 (s, 1H), 8.83 (s, 1H).

(2) Dimethylcarbamothioic acid O-[7-(pyridin-3-yl)benzo[d]isothiazol-6-yl]

A title compound (yellow oil material, 141 mg, yield of 44%) was obtained according to the same method as in Examples 18 (2) and 22 (1) using 6-methoxy-7-(pyridin-3-yl)benzo[d]isothiazole (250 mg, 1.03 mmol) obtained in the above-described example.

$^1$H NMR (CDCl$_3$, 400 MHz): δ=3.17 (s, 3H), 3.34 (s, 3H), 7.34 (d, 1H, J=9Hz), 7.44 (dd, 1H, J=5Hz, 8Hz), 7.99 (dt, 1H, J=2Hz, 8Hz), 8.08 (d, 1H, J=9Hz), 8.69 (dd, 1H, J=2Hz, 5Hz), 8.84 (s, 1H), 8.95 (s, 1H).

(3) Dimethylcarbamothioic acid S-[7-(pyridin-3-yl)benzo[d]isothiazol-6-yl]

A title compound (colorless oil material, 18 mg, yield of 13%) was obtained according to the same method as in Example 27 (2) using dimethylcarbamothioic acid O-[7-(pyridin-3-yl)benzo[d]isothiazol-6-yl] (141 mg, 0.45 mmol) obtained in the above-described example.

$^1$H NMR (CDCl$_3$, 400 MHz): δ=2.97 (s, 6H), 7.44 (dd, 1H, J=5Hz, 8Hz), 7.73 (d, 1H, J=8Hz), 7.8-7.9 (m, 1H), 8.07 (d, 1H, J=8Hz), 8.6-8.8 (m, 2H), 8.97 (s, 1H).

(4) t-Butyl 2-methyl-2-[[7-(pyridin-3-yl)benzo[d]isothiazol-6-yl]thio]propanoate A title compound (light yellow oil material, 5 mg, yield of 23%) was obtained according to the same method as in Examples 22 (3) and 23 using dimethylcarbamothioic acid S-[7-(pyridin-3-yl)benzo[d]isothiazol-6-yl] (18 mg, 0.06 mmol) obtained in the above-described example.

$^1$H NMR (CDCl$_3$, 400 MHz): δ=1.31 (s, 6H), 1.44 (s, 9H), 7.46 (dd, 1H, J=5Hz, 8Hz), 7.71 (d, 1H, J=8Hz), 7.82 (dt, 1H, J=1Hz, 8Hz), 7.99 (d, 1H, J=8Hz), 8.6-8.8 (m, 2H), 8.94 (s, 1H).

EXAMPLE 96

2-Methyl-2-[[7-(pyridin-3-yl)benzo[d]isothiazol-6-yl]thio]propanoic acid

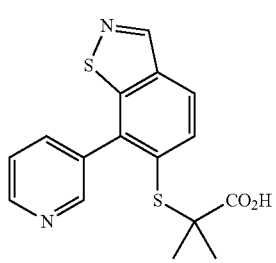 [SMILES: CC(C)(Sc1ccc2cnsc2c1-c1cccnc1)C(=O)O]

A title compound (white crystal, 6 mg, yield of 100%) was obtained according to the same method as in Example 6 using t-butyl 2-methyl-2-[[7-(pyridin-3-yl)benzo[d]isothiazol-6-yl]thio]propanoate (5 mg, 0.01 mmol) obtained in Example 95.

$^1$H NMR (CD$_3$OD, 400 MHz): δ=1.36 (s, 6H), 7.61 (dd, 1H, J=6Hz, 7Hz), 7.84 (d, 1H, J=8Hz), 7.98 (dt, 1H, J=2Hz, 8Hz), 8.17 (d, 1H, J=8Hz), 8.6-8.7 (m, 2H), 9.05 (s, 1H).

EXAMPLE 97

Ethyl 2-methyl-2-[[7-(pyridin-4-yl)benzo[d]isothiazol-6-yl]thio]propanoate

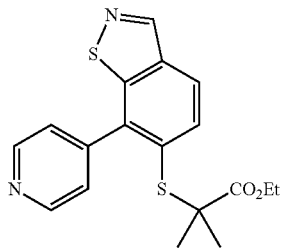 [SMILES: CCOC(=O)C(C)(C)Sc1ccc2cnsc2c1-c1ccncc1]

(1) 6-Methoxy-7-(pyridin-4-yl)benzo[d]isothiazole

A title compound (white crystal, 122 mg, yield of 63%) was obtained according to the same method as in Example 16 (2) using 7-bromo-6-methoxybenzo[d]isothiazole (200 mg, 0.82 mmol) and pyridin-4-ylboronic acid (121 mg, 0.98 mmol).

$^1$H NMR (CDCl$_3$, 400 MHz): δ=3.93 (s, 3H), 7.23 (d, 1H, J=9Hz), 7.55 (dd, 21H, J=2Hz, 5Hz), 8.04 (d, 1H, J=9Hz), 8.72 (dd, 2H, J=2Hz, 5Hz), 8.83 (s, 1H).

(2) Dimethylcarbamothioic acid O-[7-(pyridin-4-yl)benzo[d]isothiazol-6-yl]

A title compound (light yellow crystal, 156 mg, yield of 99%) was obtained according to the same method as in Examples 18 (2) and 22 (1) using 6-methoxy-7-(pyridin-4-yl)benzo[d]isothiazole (122 mg, 0.50 mmol) obtained in the above-described example.

$^1$H NMR (CDCl$_3$, 400 MHz): δ=3.16 (s, 3H), 3.35 (s, 3H), 7.31 (d, 1H, J=9Hz), 7.5-7.6 (m, 2H), 8.06 (d, 1H, J=9Hz), 8.74 (d, 2H, J=6Hz), 8.93 (s, 1H).

(3) Dimethylcarbamothioic acid S-[7-(pyridin-4-yl)benzo[d]isothiazol-6-yl]

A title compound (colorless oil material, 89 mg, yield of 57%) was obtained according to the same method as in Example 27 (2) using dimethylcarbamothioic acid O-[7-(pyridin-4-yl)benzo[d]isothiazol-6-yl] (156 mg, 0.47 mmol) obtained in the above-described example.

$^1$H NMR (CDCl$_3$, 400 MHz): δ=2.95 (s, 6H), 7.3-7.5 (m, 2H), 7.70 (d, 1H, J=8Hz), 8.05 (d, 1H, J=8Hz), 8.73 (d, 2H, J=5Hz), 8.94 (s, 1H).

(4) Ethyl 2-methyl-2-[[7-(pyridin-4-yl)benzo[d]isothiazol-6-yl]thio]propanoate A title compound (colorless oil material, 33 mg, yield of 34%) was obtained according to the same method as in Examples 22 (3) and 1 (3) using dimethylcarbamothioic acid S-[7-(pyridin-4-yl)benzo[d]isothiazol-6-yl] (89 mg, 0.27 mmol) obtained in the above-described example.

$^1$H NMR (CDCl$_3$, 400 MHz): δ=1.21 (t, 3H, J=7Hz), 1.42 (s, 6H), 3.02 (q, 2H, J=7Hz), 7.54 (dd, 2H, J=2Hz, 5Hz), 7.83 (d, 1H, J=8Hz), 7.94 (d, 1H, J=8Hz), 8.68 (dd, 2H, J=2Hz, 5Hz), 8.89 (s, 1H).

EXAMPLE 98

2-Methyl-2-[[7-(pyridin-4-yl)benzo[d]isothiazol-6-yl]thio]propanoic acid

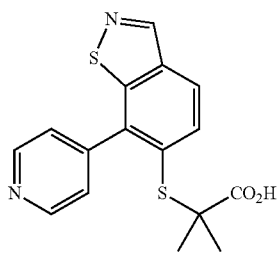 [SMILES: CC(C)(Sc1ccc2cnsc2c1-c1ccncc1)C(=O)O]

A title compound (white crystal, 8.5 mg, yield of 28%) was obtained according to the same method as in Example 2 using ethyl 2-methyl-2-[[7-(pyridin-4-yl)benzo[d]isothiazol-6-yl]thio]propanoate (33 mg, 0.09 mmol) obtained in Example 97.

$^1$H NMR (CDCl$_3$, 400 MHz): δ=1.43 (s, 6H), 7.73 (d, 2H, J=5Hz), 7.83 (d, 1H, J=8Hz), 8.02 (d, 1H, J=8Hz), 8.59 (d, 2H, J=5Hz), 8.95 (s, 1H).

EXAMPLE 99

Ethyl 2-methyl-2-[[7-[6-(methylthio)pyridin-3-yl]benzo[d]isothiazol-6-yl]thio]propanoate

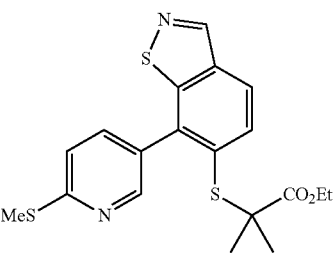 [SMILES: CCOC(=O)C(C)(C)Sc1ccc2cnsc2c1-c1ccc(SC)nc1]

(1) 6-Methoxy-7-[6-(methylthio)pyridin-3-yl]benzo[d]isothiazole

A title compound (white crystal, 254 mg, yield of 72%) was obtained according to the same method as in Example 16 (2) using 7-bromo-6-methoxybenzo[d]isothiazole (300 mg, 1.23 mmol) and [6-(methylthio)pyridin-3-yl]boronic acid (249 mg, 1.47 mmol).

$^1$H NMR (CDCl$_3$, 400 MHz): δ=2.61 (s, 3H), 3.89 (s, 3H), 7.20 (d, 1H, J=9Hz), 7.28 (d, 1H, J=8Hz), 7.73 (dd, 1H, J=2Hz, 8Hz), 7.99 (d, 1H, J=9Hz), 8.68 (d, 1H, J=2Hz), 8.83 (s, 1H).

(2) Dimethylcarbamothioic acid O-[7-[6-(methylthio)pyridin-3-yl]benzo[d]isothiazol-6-yl]

A title compound (purple oil material, 64 mg, yield of 20%) was obtained according to the same method as in Examples 18 (2) and 22 (1) using 6-methoxy-7-[6-(methylthio)pyridin-3-yl]benzo[d]isothiazole (254 mg, 0.88 mmol) obtained in the above-described example.

$^1$H NMR (CDCl$_3$, 400 MHz): δ=2.62 (s, 3H), 3.19 (s, 3H), 3.35 (s, 3H), 7.2-7.4 (m, 2H), 7.75 (dd, 1H, J=2Hz, 8Hz), 8.03 (d, 1H, J=9Hz), 8.6-8.7 (m, 1H), 8.92 (s, 1H).

(3) Dimethylcarbamothioic acid S-[7-[6-(methylthio)pyridin-3-yl]benzo[d]isothiazol-6-yl]

A title compound (purple oil material, 38 mg, yield of 59%) was obtained according to the same method as in Example 27 (2) using dimethylcarbamothioic acid O-[7-[6-(methylthio)pyridin-3-yl]benzo[d]isothiazol-6-yl] (64 mg, 0.18 mmol) obtained in the above-described example.

$^1$H NMR (CDCl$_3$, 400 MHz): δ=2.63 (s, 3H), 2.97 (s, 6H), 7.28 (d, 1H, J=8Hz), 7.61 (dd, 1H, J=2Hz, 8Hz), 7.69 (d, 1H, J=8Hz), 8.03 (d, 1H, J=8Hz), 8.53 (dd, 1H, J=1Hz, 2Hz), 8.94 (s, 1H).

(4) Ethyl 2-methyl-2-[[7-[6-(methylthio)pyridin-3-yl]benzo[d]isothiazol-6-yl]thio]propanoate A title compound (colorless oil material, 16 mg, yield of 37%) was obtained according to the same method as in Examples 22 (3) and 1 (3) using dimethylcarbamothioic acid S-[7-[6-(methylthio)pyridin-3-yl]benzo[d]isothiazol-6-yl] (38 mg, 0.11 mmol) obtained in the above-described example.

$^1$H NMR (CDCl$_3$, 400 MHz): δ=1.18 (t, 3H, J=7Hz), 1.35 (s, 6H), 2.64 (s, 3H), 4.02 (q, 2H, J=7Hz), 7.30 (d, 1H, J=8Hz), 7.60 (dd, 1H, J=2Hz, 8Hz), 7.63 (d, 1H, J=8Hz), 7.95 (d, 1H, J=8Hz), 8.54 (d, 1H, J=2Hz), 8.92 (s, 1H).

EXAMPLE 100

2-Methyl-2-[[7-[6-(methylthio)pyridin-3-yl]benzo[d]isothiazol-6-yl]thio]propanoic acid

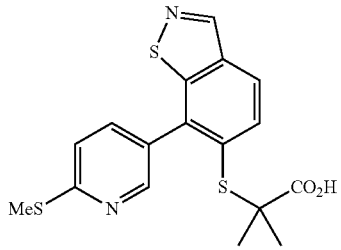

A title compound (brown amorphous, 5.5 mg, yield of 37%) was obtained according to the same method as in Example 2 using ethyl 2-methyl-2-[[7-[6-(methylthio)pyridin-3-yl]benzo[d]isothiazol-6-yl]thio]propanoate (16 mg, 0.09 mmol) obtained in Example 99.

$^1$H NMR (CDCl$_3$, 400 MHz): δ=1.42 (s, 6H), 2.63 (s, 3H), 7.31 (d, 1H, J=8Hz), 7.64 (dd, 1H, J=2Hz, 8Hz), 7.75 (d, 1H, J=8Hz), 7.97 (d, 1H, J=8Hz), 8.57 (d, 1H, J=2Hz), 8.94 (s, 1H).

EXAMPLE 101 t-Butyl 2-[[7-(4-cyanophenyl)-4-fluorobenzo[d]isothiazol-6-yl]thio]-2-methylpropanoate

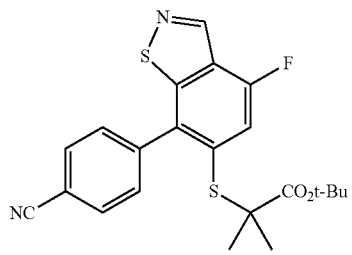 [SMILES: CC(C)(C)OC(=O)C(C)(C)Sc1cc(F)c2cnsc2c1-c1ccc(C#N)cc1]

(1) 7-Bromo-4-fluoro-6-methoxybenzo[d]isothiazole

A title compound (light yellow crystal, 367 mg, yield of 100%) was obtained according to the same method as in Example 25 (1) using 4-fluoro-6-methoxybenzo[d]thiazole (260 mg, 1.42 mmol).
$^1$H NMR (CDCl$_3$, 400 MHz): δ=4.02 (s, 3H), 7.42 (d, 1H, J=12Hz), 9.25 (s, 1H).

(2) 4-(4-Fluoro-6-methoxybenzo[d]isothiazol-7-yl)benzonitrile

A title compound (white crystal, 160 mg, yield of 40%) was obtained according to the same method as in Example 16 (2) using 7-bromo-4-fluoro-6-methoxybenzo[d]isothiazole (367 mg, 1.4 mmol) obtained in the above-described example and (4-cyanophenyl)boronic acid (313 mg, 2.13 mmol).
$^1$H NMR (CDCl$_3$, 400 MHz): δ=3.91 (s, 3H), 6.94 (d, 1H, J=11Hz), 7.70 (d, 2H, J=8Hz), 7.79 (d, 2H, J=8Hz), 8.92 (s, 1H).

(3) Dimethylcarbamothioic acid O-[7-(4-cyanophenyl)-4-fluorobenzo[d]isothiazol-6-yl]

A title compound (yellow amorphous, 140 mg, yield of 89%) was obtained according to the same method as in Examples 18 (2) and 22 (1) using 4-(4-fluoro-6-methoxybenzo[d]isothiazol-7-yl)benzonitrile (160 mg, 0.56 mmol) obtained in the above-described example.
$^1$H NMR (CDCl$_3$, 400 MHz): δ=3.15 (s, 3H), 3.35 (s, 3H), 7.04 (d, 1H, J=10Hz), 7.71 (d, 2H, J=8Hz), 7.79 (d, 2H, J=8Hz), 9.03 (s, 1H).

(4) Dimethylcarbamothioic acid S-[7-(4-cyanophenyl)-4-fluorobenzo[d]isothiazol-6-yl]

A title compound (yellow oil material, 120 mg, yield of 100%) was obtained according to the same method as in Example 27 (2) using dimethylcarbamothioic acid O-[7-(4-cyanophenyl)-4-fluorobenzo[d]isothiazol-6-yl] (120 mg, 0.34 mmol) obtained in the above-described example.
$^1$H NMR (CDCl$_3$, 400 MHz): δ=2.98 (s, 6H), 7.42 (d, 1H, J=9Hz), 7.58 (d, 2H, J=9Hz), 7.79 (d, 2H, J=9Hz), 9.05 (s, 1H).

(5) t-Butyl 2-[[7-(4-cyanophenyl)-4-fluorobenzo[d]isothiazol-6-yl]thio]-2-methylpropanoate A title compound (light yellow oil material, 90 mg, yield of 58%) was obtained according to the same method as in Examples 22 (3) and 23 using dimethylcarbamothioic acid S-[7-(4-cyanophenyl)-4-fluorobenzo[d]isothiazol-6-yl] (130 mg, 0.36 mmol) obtained in the above-described example.
$^1$H NMR (CDCl$_3$, 400 MHz): δ=1.35 (s, 6H), 1.47 (s, 9H), 7.40 (d, 1H, J=9Hz), 7.56 (d, 2H, J=9Hz), 7.81 (d, 2H, J=9Hz), 9.00 (s, 1H).

EXAMPLE 102

2-[[7-(4-Cyanophenyl)-4-fluorobenzo[d]isothiazol-6-yl]thio]-2-methylpropanoic acid

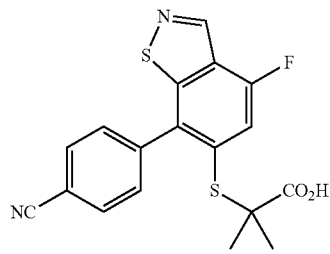 [SMILES: CC(C)(Sc1cc(F)c2cnsc2c1-c1ccc(C#N)cc1)C(=O)O]

A title compound (white crystal, 12 mg, yield of 15%) was obtained according to the same method as in Example 6 using t-butyl 2-[[7-(4-cyanophenyl)-4-fluorobenzo[d]isothiazol-6-yl]thio]-2-methylpropanoate (90 mg, 0.21 mmol) obtained in Example 101.
$^1$H NMR (CDCl$_3$, 400 MHz): δ=1.31 (s, 6H), 7.40 (d, 1H, J=10Hz), 7.66 (d, 2H, J=8Hz), 8.01 (d, 2H, J=9Hz), 9.31 (s, 1H).

EXAMPLE 103 t-Butyl 2-[[7-(4-cyanophenyl)-5-fluorobenzo[d]isothiazol-6-yl]thio]-2-methylpropanoate

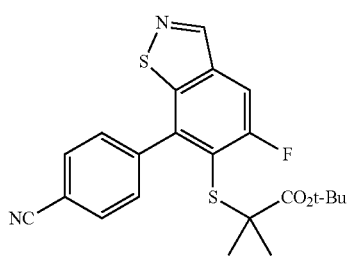 [SMILES: CC(C)(C)OC(=O)C(C)(C)Sc1c(F)cc2cnsc2c1-c1ccc(C#N)cc1]

(1) 7-Bromo-5-fluoro-6-methoxybenzo[d]isothiazole

5-Fluoro-6-methoxybenzo[d]isothiazole (225 mg, 1.23 mmol) was dissolved in acetic acid (5 mL), bromine (70 μL, 1.35 mmol) was added thereto, and the solution was stirred at 60° C. After 11 hours, the reaction solution was concentrated, saturated sodium hydrogen carbonate aqueous solution was added to the obtained residue, and extraction was carried out using ethyl acetate. The organic layer was dried over sodium sulfate and filtered, and then the solvent was distilled off under reduced pressure. The obtained residue was purified by silica gel column chromatography (ethyl acetate:hexane=1:4) to obtain a title compound (yellow crystal, 203 mg, yield of 63%).

¹H NMR (CDCl₃, 400 MHz): δ=4.08 (d, 3H, J=2Hz), 7.72 (d, 1H, J=10Hz), 8.90 (s, 1H).

(2) 4-(5-Fluoro-6-methoxybenzo[d]isothiazol-7-yl)benzonitrile

A title compound (white amorphous, 190 mg, yield of 86%) was obtained according to the same method as in Example 16 (2) using 7-bromo-5-fluoro-6-methoxybenzo[d]isothiazole (201 mg, 0.77 mmol) and (4-cyanophenyl)boronic acid (135 mg, 0.92 mmol).

¹H NMR (CDCl₃, 400 MHz): δ=3.86 (d, 3H, J=2Hz), 7.7-7.9 (m, 5H), 8.86 (s, 1H).

(3) Dimethylcarbamothioic acid O-[7-(4-cyanophenyl)-5-fluorobenzo[d]isothiazol-6-yl]

A title compound (white amorphous, 193 mg, yield of 82%) was obtained according to the same method as in Examples 18 (2) and 22 (1) using 4-(5-fluoro-6-methoxybenzo[d]isothiazol-7-yl)benzonitrile (189 mg, 0.66 mmol) obtained in the above-described example.

¹H NMR (CDCl₃, 400 MHz): δ=3.23 (s, 3H), 3.40 (s, 3H), 7.81 (s, 4H), 7.85 (d, 1H, J=9Hz), 8.93 (s, 1H).

(4) Dimethylcarbamothioic acid S-[7-(4-cyanophenyl)-5-fluorobenzo[d]isothiazol-6-yl]

A title compound (white amorphous, 165 mg, yield of 86%) was obtained according to the same method as in Example 27 (2) using dimethylcarbamothioic acid O-[7-(4-cyanophenyl)-5-fluorobenzo[d]isothiazol-6-yl] (191 mg, 0.53 mmol) obtained in the above-described example.

¹H NMR (CDCl₃, 400 MHz): δ=3.00 (s, 3H), 3.03 (s, 3H), 7.59 (d, 2H, J=8Hz), 7.81 (d, 2H, J=9Hz), 7.84 (d, 1H, J=8Hz), 8.94 (s, 1H).

(5) t-Butyl 2-[[7-(4-cyanophenyl)-5-fluorobenzo[d]isothiazol-6-yl]thio]-2-methylpropanoate A title compound (white amorphous, 21 mg, yield of 17%) was obtained according to the same method as in Examples 22 (3) and 23 using dimethylcarbamothioic acid S-[7-(4-cyanophenyl)-5-fluorobenzo[d]isothiazol-6-yl] (133 mg, 0.34 mmol) obtained in the above-described example.

¹H NMR (CDCl₃, 400 MHz): δ=1.25 (s, 6H), 1.39 (s, 9H), 7.60 (d, 2H, J=8Hz), 7.7-7.9 (m, 3H), 8.92 (s, 1H).

EXAMPLE 104

2-[[7-(4-Cyanophenyl)-5-fluorobenzo[d]isothiazol-6-yl]thio]-2-methylpropanoic acid

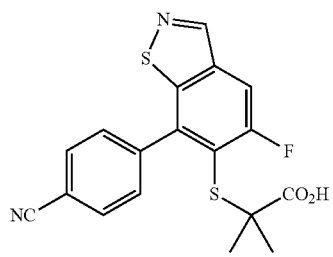 [SMILES: CC(C)(Sc1c(F)cc2cnsc2c1-c1ccc(C#N)cc1)C(=O)O]

A title compound (white crystal, 7.4 mg, yield of 43%) was obtained according to the same method as in Example 6 using t-butyl 2-[[7-(4-cyanophenyl)-5-fluorobenzo[d]isothiazol-6-yl]thio]-2-methylpropanoate (20 mg, 0.05 mmol) obtained in Example 103.

¹H NMR (CDCl₃, 400 MHz): δ=1.36 (s, 6H), 7.61 (d, 2H, J=8Hz), 7.80-7.82 (m, 3H), 8.94 (s, 1H).

EXAMPLE 105

Ethyl 2-[[7-(4-cyanophenyl)-3-methylbenzo[d]isothiazol-6-yl]oxy]-2-methylpropanoate

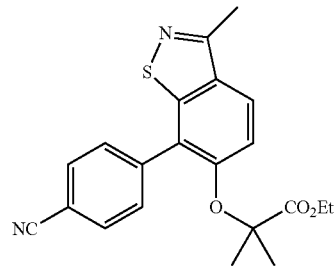 [SMILES: CCOC(=O)C(C)(C)Oc1ccc2c(C)nsc2c1-c1ccc(C#N)cc1]

(1) 1-[2-(Benzylthio)-4-methoxyphenyl]-1-ethanone

Benzyl mercaptan (0.64 mL, 5.5 mmol) was dissolved in tetrahydrofuran (30 mL) in a nitrogen atmosphere and potassium t-butoxide (620 mg, 5.5 mmol) was gradually added thereto. After 1 hour, a tetrahydrofuran (10 mL) solution of 1-(2-fluoro-4-methoxyphenyl)-1-ethanone (840 mg, 5 mmol) was added thereto and the solution was refluxed. After 3 hours, the reaction solution was allowed to be cooled to room temperature, diluted with ethyl acetate, and washed with water and brine. The organic layer was dried over sodium sulfate and filtered, and then the solvent was distilled off under reduced pressure. The obtained residue was purified by silica gel column chromatography (ethyl acetate:hexane=1:2) to obtain a title compound (pale brown crystal, 1.09 g, yield of 80%).

¹H NMR (CDCl₃, 400 MHz): δ=2.56 (s, 3H), 3.79 (s, 3H), 4.12 (s, 2H), 6.67 (dd, 1H, J=3Hz, 9Hz), 6.86 (d, 1H, J=3Hz), 7.2-7.4 (m, 3H), 7.44 (d, 2H, J=7Hz), 7.83 (d, 1H, J=9Hz).

(2) 6-Methoxy-3-methylbenzo[d]isothiazole

1-[2-(benzylthio)-4-methoxyphenyl]-1-ethanone (1.09 g, 4 mmol) obtained in the above-described example was dissolved in dichloromethane (11 mL) and sulfuryl chloride (320 μL, 4 mmol) was added thereto in an ice bath under a nitrogen atmosphere. After 1 hour, the reaction solution was concentrated, the obtained residue was dissolved in tetrahydrofuran (10 mL), 2 M NH₃-EtOH (10 mL) was added thereto, and the solution was stirred at room temperature. After 20 hours, the reaction solution was diluted with ethyl acetate and washed with water and brine. The organic layer was dried over sodium sulfate and filtered, and then the solvent was distilled off under reduced pressure. The obtained residue was purified by silica gel column chromatography (ethyl acetate:hexane=1:2) to obtain a title compound (yellow crystal, 0.54 g, yield of 75%).

¹H NMR (CDCl₃, 400 MHz): δ=2.69 (s, 3H), 3.91 (s, 3H), 7.03 (dd, 1H, J=3Hz, 9Hz), 7.29 (d, 1H, J=3Hz), 7.78 (d, 1H, J=9Hz).

(3) 7-Bromo-6-methoxy-3-methylbenzo[d]isothiazole

6-Methoxy-3-methylbenzo[d]isothiazole (0.54 g, 3.0 mmol) obtained in the above-described example was dissolved in chloroform (11 mL), bromine (370 μL, 3.0 mmol) was added thereto, and the solution was stirred. After 2 hours, the reaction suspension was filtered and the obtained crystals were washed with chloroform to obtain a title compound (yellow crystal, 0.75 g, yield of 97%).

¹H NMR (CDCl₃, 400 MHz): δ=2.70 (s, 3H), 4.03 (s, 3H), 7.08 (d, 1H, J=9Hz), 7.83 (d, H, J=9Hz).

(4) 4-(6-Methoxy-3-methylbenzo[d]isothiazol-7-yl)benzonitrile

A title compound (white amorphous, 0.51 g, yield of 62%) was obtained according to the same method as in Example 16 (2) using 7-bromo-6-methoxy-3-methylbenzo[d]isothiazole (0.75 g, 2.9 mmol) and (4-cyanophenyl)boronic acid (0.59 g, 4.0 mmol) obtained in the above-described example.

¹H NMR (CDCl₃, 400 MHz): δ=2.73 (s, 3H), 3.93 (s, 3H), 7.22 (d, 1H, J=9Hz), 7.74 (d, 2H, J=9Hz), 7.78 (d, 2H, J=9Hz), 7.93 (d, 1H, J=9Hz).

(5) Ethyl 2-[[7-(4-cyanophenyl)-3-methylbenzo[d]isothiazol-6-yl]oxy]-2-methylpropanoate A crude material (0.34 g) of 4-(6-hydroxy-3-methylbenzo[d]isothiazol-7-yl)benzonitrile was obtained according to the same method as in Example 18 (2) using 4-(6-methoxy-3-methylbenzo[d]isothiazol-7-yl)benzonitrile (0.51 g, 1.8 mmol) obtained in the above-described example.

A title compound (colorless oil material, 7 mg, yield of 18%) was obtained according to the same method as in Example 1 (3) using the obtained crude material (27 mg).

¹H NMR (CDCl₃, 400 MHz): δ=1.25 (t, 3H, J=7Hz), 1.48 (s, 6H), 2.71 (s, 3H), 4.24 (q, 2H, J=7Hz), 7.04 (d, 1H, J=9Hz), 7.77 (s, 4H), 7.80 (d, 1H, J=9Hz).

EXAMPLE 106

2-[[7-(4-Cyanophenyl)-3-methylbenzo[d]isothiazol-6-yl]oxy]-2-methylpropanoic acid

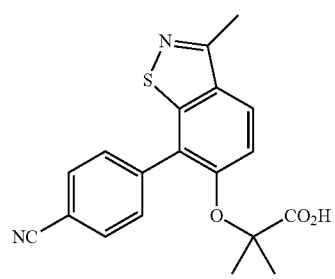 [SMILES: Cc1nsc2c(-c3ccc(C#N)cc3)c(OC(C)(C)C(=O)O)ccc12]

A title compound (white crystal, 5 mg, yield of 78%) was obtained according to the same method as in Example 6 using ethyl 2-[[7-(4-cyanophenyl)-3-methylbenzo[d]isothiazol-6-yl]oxy]-2-methylpropanoate (7 mg, 0.02 mmol) obtained in Example 105.

¹H NMR (CDCl₃, 400 MHz): δ=1.49 (s, 6H), 2.72 (s, 3H), 7.16 (d, 1H, J=9Hz), 7.74 (d, 2H, J=9Hz), 7.78 (d, 2H, J=9Hz), 7.84 (d, 1H, J=9Hz).

EXAMPLE 107

Ethyl 2-[[7-(4-Cyanophenyl)-3-methylbenzo[d]isothiazol-6-yl]thio]-2-methylpropanoate

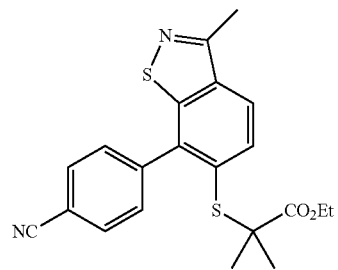 [SMILES: CCOC(=O)C(C)(C)Sc1ccc2c(C)nsc2c1-c1ccc(C#N)cc1]

(1) Dimethylcarbamothioic acid O-[7-(4-cyanophenyl)-3-methylbenzo[d]isothiazol-6-yl]

A title compound (pale brown crystal, 0.27 g, yield of 63%) was obtained according to the same method as in Example 22 (1) using the crude material (0.31 g) of 4-(6-hydroxy-3-methylbenzo[d]isothiazol-7-yl)benzonitrile obtained in Example 105 (5).

¹H NMR (CDCl₃, 400 MHz): δ=2.77 (s, 3H), 3.19 (s, 3H), 3.36 (s, 3H), 7.31 (d, 1H, J=9Hz), 7.75 (d, 2H, J=9Hz), 7.78 (d, 2H, J=9Hz), 7.95 (d, 1H, J=9Hz).

(2) Dimethylcarbamothioic acid S-[7-(4-cyanophenyl)-3-methylbenzo[d]isothiazol-6-yl]

A title compound (brown crystal, 0.27 g, yield of 100%) was obtained according to the same method as in Example 27 (2) using dimethylcarbamothioic acid O-[7-(4-cyanophenyl)-3-methylbenzo[d]isothiazol-6-yl] (0.27 g, 0.73 mmol) obtained in the above-described example.

¹H NMR (CDCl₃, 400 MHz): δ=2.76 (s, 3H), 2.96 (s, 6H), 7.56 (d, 1H, J=9Hz), 7.69 (d, 2H, J=9Hz), 7.76 (d, 2H, J=9Hz), 7.92 (d, 1H, J=9Hz).

(3) Ethyl 2-[[7-(4-cyanophenyl)-3-methylbenzo[d]isothiazol-6-yl]thio]-2-methylpropanoate A title compound (colorless oil material, 150 mg, yield of 52%) was obtained according to the same method as in Examples 22 (3) and 1 (3) using dimethylcarbamothioic acid S-[7-(4-cyanophenyl)-3-methylbenzo[d]isothiazol-6-yl] (0.27 g, 0.73 mmol) obtained in the above-described example.

¹H NMR (CDCl₃, 400 MHz): δ=1.22 (t, 3H, J=7Hz), 1.34 (s, 6H), 2.76 (s, 3H), 4.05 (d, 2H, J=7Hz), 7.59 (d, 1H, J=9Hz), 7.63 (d, 2H, J=9Hz), 7.79 (d, 2H, J=9Hz), 7.87 (d, 1H, J=9Hz).

EXAMPLE 108

2-[[7-(4-Cyanophenyl)-3-methylbenzo[d]isothiazol-6-yl]thio]-2-methylpropanoic acid

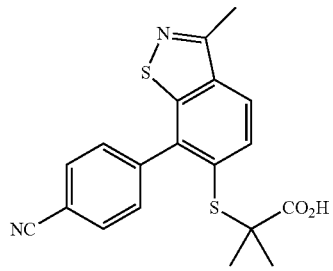

A title compound (white crystal, 85 mg, yield of 61%) was obtained according to the same method as in Example 26 using ethyl 2-[[7-(4-cyanophenyl)-3-methylbenzo[d]isothiazol-6-yl]thio]-2-methylpropanoate (150 mg, 0.38 mmol) obtained in Example 107.

$^1$H NMR (CDCl$_3$, 400 MHz): δ=1.38 (s, 6H), 2.77 (s, 3H), 7.59 (d, 2H, J=8Hz), 7.74 (d, 1H, J=8Hz), 7.77 (d, 2H, J=8Hz), 7.89 (d, 1H, J=8Hz).

EXAMPLE 109

Ethyl 5-[6-[[1-(t-butoxy)-2-methyl-1-oxopropan-2-yl]thio]-3-methylbenzo[d]isothiazol-7-yl]picolinate

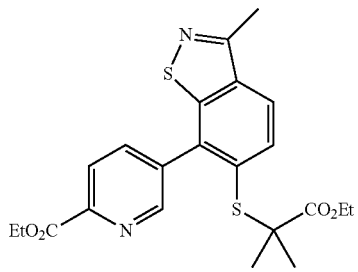 [SMILES: CCOC(=O)c1ccc(-c2c(SC(C)(C)C(=O)OCC)ccc3c(C)nsc23)cn1]

(1) 5-(6-Methoxy-3-methylbenzo[d]isothiazol-7-yl)picolinonitrile

A title compound (white crystal, 67 mg, yield of 62%) was obtained according to the same method as in Example 1 (1) using 7-bromo-6-methoxy-3-methylbenzo[d]isothiazole (100 mg, 0.39 mmol) obtained in Example 105 (3) and (6-cyanopyridin-3-yl)boronic acid (69 mg, 0.47 mmol).

$^1$H NMR (CDCl$_3$, 400 MHz): δ=2.74 (s, 3H), 3.95 (s, 3H), 7.23 (d, 1H, J=9Hz), 7.82 (dd, 1H, J=1Hz, 8Hz), 7.96 (d, 1H, J=9Hz), 8.10 (dd, 1H, J=2Hz, 8Hz), 8.98 (d, 1H, J=1Hz).

(2) Dimethylcarbamothioic acid O-[7-(6-cyanopyridin-3-yl)-3-methylbenzo[d]isothiazol-6-yl]

A title compound (185 mg, yield of 69%) was obtained according to the same method as in Examples 18 (2) and 22 (1) using 5-(6-methoxy-3-methylbenzo[d]isothiazol-7-yl)picolinonitrile (0.21 g, 0.75 mmol) obtained in the above-described example.

$^1$H NMR (CDCl$_3$, 400 MHz): δ=2.79 (s, 3H), 3.22 (s, 3H), 3.36 (s, 3H), 7.32 (d, 1H, J=8Hz), 7.83 (d, 1H, J=8Hz), 8.00 (d, 1H, J=9Hz), 8.15 (dd, 1H, J=2Hz, 7Hz), 8.93-8.94 (m, 1H).

(3) Dimethylcarbamothioic acid S-[7-(6-cyanopyridin-3-yl)-3-methylbenzo[d]isothiazol-6-yl]

A title compound (yellow amorphous, 140 mg, yield of 76%) was obtained according to the same method as in Example 27 (2) using dimethylcarbamothioic acid O-[7-(6-cyanopyridin-3-yl)-3-methylbenzo[d]isothiazol-6-yl] (184 mg, 0.52 mmol) obtained in the above-described example.

$^1$H NMR (CDCl$_3$, 400 MHz): δ=2.79 (s, 3H), 2.9-3.0 (m, 6H), 7.73 (d, 1H, J=8Hz), 7.83 (d, 1H, J=8Hz), 7.9-8.1 (m, 2H), 8.80-8.81 (m, 1H).

(4) Ethyl 5-[6-[[1-(t-butoxy)-2-methyl-1-oxopropan-2-yl]thio]-3-methylbenzo[d]isothiazol-7-yl]picolinate A title compound (yellow oil material, 76 mg, yield of 46%) was obtained according to the same method as in Examples 22 (3) and 23 using dimethylcarbamothioic acid S-[7-(6-cyanopyridin-3-yl)-3-methylbenzo[d]isothiazol-6-yl] (138 mg, 0.39 mmol) obtained in the above-described example.

$^1$H NMR (CDCl$_3$, 400 MHz): δ=1.30 (s, 6H), 1.46 (s, 9H), 1.51 (t, 3H, J=7Hz), 2.77 (s, 3H), 4.55 (q, 2H, J=7Hz), 7.72 (d, 1H, J=8Hz), 7.90 (d, 1H, J=8Hz), 7.97 (dd, 1H, J=2Hz, 9Hz), 8.29 (d, 1H, J=8Hz), 8.86 (d, 1H, J=2Hz).

EXAMPLE 110

2-[[7-[6-(Ethoxycarbonyl)pyridin-3-yl]-3-methylbenzo[d]isothiazol-6-yl]thio]-2-methylpropanoic acid

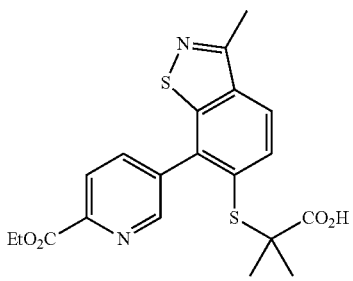 [SMILES: CCOC(=O)c1ccc(-c2c(SC(C)(C)C(=O)O)ccc3c(C)nsc23)cn1]

A title compound (pale brown crystal, 30 mg, yield of 47%) was obtained according to the same method as in Example 6 using ethyl 5-[6-[[1-(t-butoxy)-2-methyl-1-oxopropan-2-yl]thio]-3-methylbenzo[d]isothiazol-7-yl]picolinate (74 mg, 0.17 mmol) obtained in Example 109.

$^1$H NMR (DMSO-d$_6$, 400 MHz): δ=1.28 (s, 6H), 1.38 (t, 3H, J=7Hz), 2.76 (s, 3H), 4.40 (q, 2H, J=7Hz), 7.79 (d, 1H, J=8Hz), 8.11 (dd, 1H, J=2Hz, 8Hz), 8.20 (d, 2H, J=8Hz), 8.77 (d, 1H, J=2Hz).

EXAMPLE 111

Ethyl 1-[[7-(4-cyanophenyl)-3-methylbenzo[d]iso-thiazol-6-yl]thio]cyclobutan-1-carboxylate

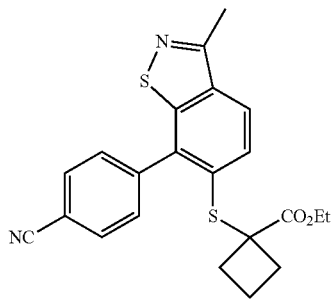 [SMILES: CCOC(=O)C1(Sc2ccc3c(C)nsc3c2-c2ccc(C#N)cc2)CCC1]

4-(6-Mercapto-3-methylbenzo[d]isothiazol-7-yl)benzonitrile (43 mg, 0.15 mmol) and sodium carbonate (48 mg, 0.46 mmol) were dissolved in dimethylformamide (1.5 mL), ethyl 1-bromocyclobutan-1-carboxylate (49 μL, 0.30 mmol) was added thereto, and the solution was stirred at 60° C. for 17 hours. The reaction solution was allowed to be cooled to room temperature, diluted with ethyl acetate, and washed with water and brine. The organic layer was dried over sodium sulfate and filtered, and then the solvent was distilled off under reduced pressure. The obtained residue was purified by silica gel column chromatography (NH silica, ethyl acetate:hexane=1:9) to obtain a title compound (light yellow crystal, 20 mg, yield of 33%).

$^1$H NMR (CDCl$_3$, 400 MHz): δ=1.14 (t, 3H, J=8Hz), 1.8-2.0 (m, 2H), 2.0-2.1 (m, 2H), 2.6-2.7 (m, 2H), 2.78 (s, 3H), 4.04 (q, 2H, J=8Hz), 7.52 (d, 1H, J=9Hz), 7.58 (d, 2H, J=9Hz), 7.79 (d, 2H, J=9Hz), 7.86 (d, 1H, J=9Hz).

EXAMPLE 112

1-[[7-(4-Cyanophenyl)-3-methylbenzo[d]isothiazol-6-yl]thio]cyclobutan-1-carb oxylic acid

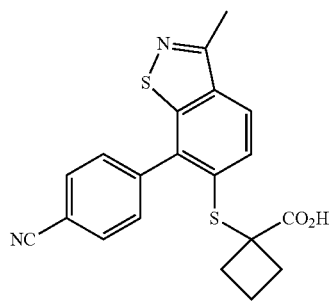 [SMILES: Cc1nsc2c(-c3ccc(C#N)cc3)c(SC3(C(=O)O)CCC3)ccc12]

Ethyl 1-[[7-(4-cyanophenyl)-3-methylbenzo[d]isothiazol-6-yl]thio]cyclobutan-1-carboxylate (20 mg, 0.049 mmol) obtained in Example 111 was dissolved in methanol (1 mL) and tetrahydrofuran (1 mL), 2 M sodium hydroxide aqueous solution (1 mL) was added thereto, and the solution was stirred at room temperature for 1 hour. The solvent is distilled off under reduced pressure, 3 M hydrochloric acid was added thereto, extraction was carried out using ethyl acetate, and the organic layer was washed with water and brine. The organic layer was dried over sodium sulfate and filtered, and then the solvent was distilled off under reduced pressure. The obtained residue was purified by preparative thin-layer chromatography (methanol:chloroform=5:95) to obtain a title compound (white crystal, 16 mg, yield of 86%).

$^1$H NMR (CDCl$_3$, 400 MHz): δ=1.9-2.1 (m, 4H), 2.6-2.7 (m, 2H), 2.80 (s, 3H), 7.56 (d, 1H, J=9Hz), 7.59 (d, 2H, J=8Hz), 7.78 (d, 2H, J=8Hz), 7.85 (d, 1H, J=9Hz).

EXAMPLE 113

2-[[7-(4-Cyanophenyl)benzo[d]isothiazol-6-yl]thio]-2-ethylbutanoic acid

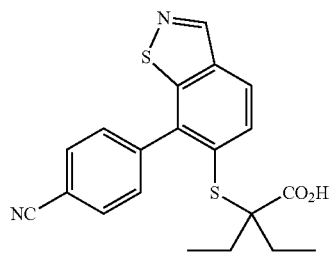 [SMILES: CCC(CC)(Sc1ccc2cnsc2c1-c1ccc(C#N)cc1)C(=O)O]

4-(6-Mercaptobenzo[d]isothiazol-7-yl)benzonitrile (101 mg, 0.376 mmol) obtained in Example 27 (3) and sodium carbonate (80 mg, 0.75 mmol) were dissolved in dimethylformamide (0.5 mL), 2-bromo-2-ethyl butanoate (113 mg, 0.579 mmol) was added thereto, and the solution was stirred at 60° C. for 4 hours and stirred at 75° C. for 2 hours. The reaction solution was allowed to be cooled to room temperature, 1 M hydrochloric acid was added thereto, extraction was carried out using ethyl acetate, and the organic layer was washed with brine. Further, the organic layer was dried over sodium sulfate and filtered, and then the solvent was distilled off under reduced pressure. The obtained residue was purified by preparative thin-layer chromatography (methanol:chloroform=1:29) to obtain a title compound (white crystal, 31 mg, yield of 21%).

$^1$H NMR (CDCl$_3$, 400 MHz): δ=0.72 (t, 6H, J=8Hz), 1.5-1.6 (m, 2H), 1.7-1.8 (m, 2H), 7.63 (d, 2H, J=8Hz), 7.73 (d, 1H, J=8Hz), 7.81 (d, 2H, J=8Hz), 7.98 (d, 1H, J=8Hz), 8.94 (s, 1H).

EXAMPLE 114

2-[[7-(4-Cyanophenyl)benzo[d]isothiazol-6-yl]thio]-3,3-dimethylbutanoic acid

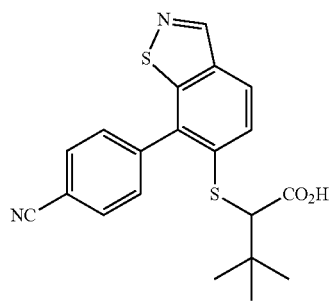 [SMILES: CC(C)(C)C(Sc1ccc2cnsc2c1-c1ccc(C#N)cc1)C(=O)O]

A title compound (white crystal, 37 mg, yield of 31%) was obtained according to the same method as in Example 113 using 4-(6-mercaptobenzo[d]isothiazol-7-yl)benzonitrile (83 mg, 0.31 mmol) obtained in Example 27 (3) and 2-bromo-3,3-dimethyl butanoate (72 mg, 0.37 mmol).

$^1$H NMR (CDCl$_3$, 400 MHz): δ=1.02 (s, 9H), 3.42 (S, 1H), 7.64 (d, 2H, J=8Hz), 7.70 (d, 1H, J=8Hz), 7.81 (d, 2H, J=8Hz), 8.01 (d, 1H, J=8Hz), 8.91 (s, 1H)

EXAMPLE 115 t-Butyl (E)-3-[[1-(4-cyanophenyl)naphthalen-2-yl]thio]-2-butenoate

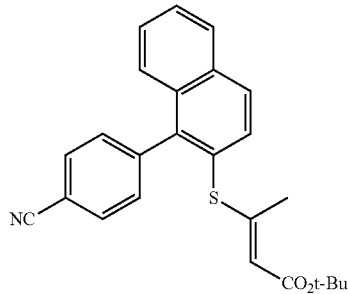 [SMILES: C/C(=C\C(=O)OC(C)(C)C)Sc1ccc2ccccc2c1-c1ccc(C#N)cc1]

4-(2-Mercaptonaphthalen-1-yl)benzonitrile (100 mg, 0.383 mmol) obtained in Example 48 (3) was dissolved in dimethylformamide (2 mL), sodium hydride (18 mg, 0.44 mmol) was added thereto, and the solution was stirred at room temperature. After 15 minutes, t-butyl 2-butynoate (86 mg, 0.61 mmol) was added to the reaction solution, and the reaction solution was stirred for 45 minutes. Next, 1 M hydrochloric acid was added to the reaction solution, extraction was carried out using ethyl acetate, and the organic layer was washed with brine. The organic layer was dried over sodium sulfate and filtered, and then the solvent was distilled off under reduced pressure. The obtained residue was purified by silica gel column chromatography (ethyl acetate:hexane=1:9) to obtain a title compound (colorless oil material, 58 mg, yield of 36%).

$^1$H NMR (CDCl$_3$, 400 MHz): δ=1.41 (s, 9H), 2.23 (s, 3H), 5.19 (s, 1H), 7.35 (d, 1H, J=8Hz), 7.40 (d, 2H, J=8Hz), 7.44 (t, 1H, J=8Hz), 7.57 (t, 1H, J=8Hz), 7.62 (d, 1H, J=8Hz), 7.76 (d, 2H, J=8Hz), 7.92 (d, 1H, J=8Hz), 7.93 (d, 1H, J=8Hz).

EXAMPLE 116

(E)-3-[[1-(4-cyanophenyl)naphthalen-2-yl]thio]-2-butenoic acid

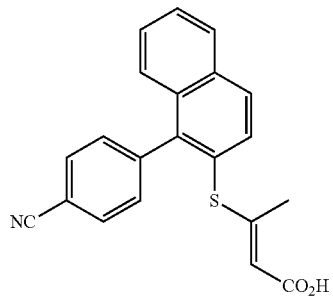 [SMILES: C/C(=C\C(=O)O)Sc1ccc2ccccc2c1-c1ccc(C#N)cc1]

t-Butyl (E)-3-[[1-(4-cyanophenyl)naphthalen-2-yl]thio]-2-butenoate (58 mg, 0.14 mmol) obtained in Example 115 was dissolved in dichloromethane (1 mL), and trifluoroacetic acid (0.2 mL) was added thereto in an ice bath. The solution was warmed to room temperature and then stirred for 10 minutes. Next, trifluoroacetic acid (0.2 mL) was added thereto in an ice bath again and the solution was warmed to room temperature. After 20 minutes, the reaction solution was concentrated under reduced pressure. The obtained residue was purified by silica gel column chromatography (ethyl acetate:hexane=1:1) to obtain a title compound (white crystal, 35 mg, 69%).

$^1$H NMR (CDCl$_3$, 400 MHz): δ=2.28 (s, 3H), 5.12 (s, 1H), 7.35 (d, 1H, J=8Hz), 7.39 (d, 2H, J=9Hz), 7.45 (t, 1H, J=8Hz), 7.59 (t, 1H, J=8Hz), 7.61 (d, 1H, J=8Hz), 7.77 (d, 2H, J=9Hz), 7.94 (d, 1H, J=9Hz), 7.96 (d, 1H, J=9Hz).

EXAMPLE 117

1-[[7-(4-Cyanophenyl)benzo[d]isothazol-6-yl]thio]cyclohexan-1-carboxylic acid

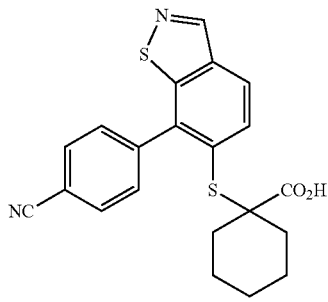 [SMILES: N#Cc1ccc(-c2c(SC3(C(=O)O)CCCCC3)ccc3cnsc23)cc1]

A title compound (white crystal, 31 mg, yield of 31%) was obtained according to the same method as in Example 113 using 4-(6-mercaptobenzo[d]isothiazol-7-yl)benzonitrile (68 mg, 0.25 mmol) obtained in Example 27 (3) and 1-bromocyclohexan-1-carboxylic acid (67 mg, 0.32 mmol).

$^1$H NMR (CDCl$_3$, 400 MHz): δ=1.25-1.26 (m, 3H), 1.5-1.6 (m, 5H), 2.00-2.02 (m, 2H), 7.62 (d, 2H, J=9Hz), 7.74 (d, 1H, J=9Hz), 7.80 (d, 2H, J=9Hz), 7.99 (d, 1H, J=9Hz), 8.94 (s, 1H).

EXAMPLE 118

Uptake of [$^{14}$C] uric acid using HEK-URAT1

(1) Experimental Method

URAT1 stably expressed HEK293 cells (HEK-URAT1) or HEK293 cells transfected with empty vector (HEK-mock) were cultured in DMEM culture medium supplemented with 10% fetal bovine serum in an incubator under conditions of 5% carbon dioxide at 37° C. Subsequently, 1×10$^5$ cells were respectively seeded in 24-well culture plate coated with poly D-lysine and the uptake test was started after the culturing for 3 days.

The uptake experiment of uric acid was performed at 37° C. The cells were washed 3 times with a solution pH 7.4 (Hanks buffer solution that does not contain chloride ions, 125 mM sodium gluconate, 4.8 mM potassium gluconate, 1.2 mM KH$_2$PO$_4$, 1.2 mM MgSO$_4$, 1.3 mM calcium gluconate, 25 mM HEPES, 5.6 mM glucose, and 12.4 mM tris) which was warmed to 37° C. for uptake experiment and equilibrated at 37° C. for 10 minutes. After a buffer solution was removed from the cells, 0.5 mL of an uptake solution containing 5 μM [$^{14}$C] uric acid with or without a test compound was respectively added and the cells were incubated for 2 minutes. The cell uptake was stopped by adding an ice-cold Hanks buffer solution without chloride ions and the cells were washed 3 times. The cells were lysed with 0.1 N sodium hydroxide and the radioactivity was measured using LSC6100 (Aloka Co., Ltd. Tokyo). Each uptake into HEK-URAT1 was acquired by subtracting uptake into HEK-mock cells from the value of HEK-URAT1, converting the result to per mg protein of cells, and setting the value from uptake without the test compound as 100%. The uptake in each condition was performed in triplicate and each value was represented by average±standard deviation.

(2) Test Results

The test results are listed in Table 1.

TABLE 1

| Test compound | % control (10 μM) | IC50 (μM) |
| --- | --- | --- |
| Example 2 | 45.4 | 2.06 |
| Example 4 | 15.1 | 0.79 |
| Example 6 | 5.4 | |
| Example 7 | 29.5 | |
| Example 8 | 61.3 | |
| Example 10 | 27.1 | |
| Example 15 | 50.1 | 3.44 |
| Example 17 | 59.3 | |
| Example 19 | 15.6 | |
| Example 21 | 48.7 | |
| Example 24 | 7.4 | 0.17 |
| Example 26 | 11.6 | |
| Example 28 | 0.1 | |
| Example 37 | 78.6 | |
| Example 45 | 36.5 | 1.58 |

It was evident that the compound of the present invention had an excellent URAT1 inhibitory action from the results of Table 1.

EXAMPLE 119

Uptake of [$^{14}$C] uric acid using HEK-URAT1

(1) Experimental Method

The URAT1 inhibitory action was measured according to the same method as in Example 118.

(2) Test Results

The test results are listed in Tables 2 and 3.

TABLE 2

| Example No. | % control (10 μM) | IC$_{50}$ (μM) |
| --- | --- | --- |
| 58 | 12.0 | N.T. |
| 60 | 69.2 | N.T. |
| 62 | 49.0 | N.T. |
| 64 | 30.1 | N.T. |
| 66 | 1.8 | 0.0215 |
| 68 | <0.1 | 0.0262 |
| 70 | 6.4 | N.T. |
| 72 | <0.1 | 0.012 |
| 74 | 6.8 | N.T. |
| 76 | 12.7 | N.T. |
| 78 | 3.2 | 0.104 |
| 80 | 29.2 | N.T. |
| 82 | <0.1 | 0.106 |
| 84 | 2.3 | 0.205 |
| 86 | 12.1 | N.T. |
| 88 | 3.8 | N.T. |
| 90 | 3.6 | 0.161 |

TABLE 3

| Example No. | % control (10 μM) | IC$_{50}$ (μM) |
| --- | --- | --- |
| 112 | 13.8 | 2.433 |
| 113 | <0.1 | 0.021 |
| 114 | 5.8 | 0.474 |
| 116 | 1.3 | 0.025 |
| 117 | 2.7 | 0.296 |

It was evident that the compound of the present invention had an excellent URAT1 inhibitory action from the results of Tables 2 and 3.

The invention claimed is:

1. A compound represented by the following Formula (I), a tautomer or stereoisomer of the compound, or a pharmaceutically acceptable salt or solvate thereof:

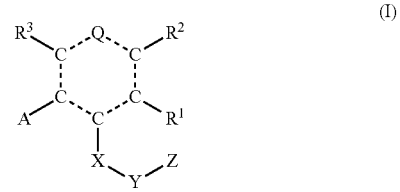

(I)

in the formula, a dotted line represents a single bond or a double bond,

Q represents CR$^8$, NR$^9$, or N, if Q represents CR$^8$, then R$^3$ and R$^8$ are bonded to each other to form a naphthalene ring or a quinoline ring together with a ring formed of dotted lines, or a combination of R$^1$ and R$^2$, R$^2$ and R$^8$, or R$^3$ and R$^8$ are bonded to each other to form a 5-membered heteroaryl ring containing 1 to 3 heteroatoms, as a ring constituent element, selected from a nitrogen atom, an oxygen atom, and a sulfur atom together with two carbon atoms to which the combination is bonded, and the heteroaryl ring forms a fused ring together with the ring formed of dotted lines, where, the ring formed of dotted lines is a ring in which the number of double bonds in the ring is the maximum, if Q represents N, then R$^1$ and R$^2$ are bonded to each other to form a quinoline ring together with the ring formed of dotted lines, if Q represents NR$^9$, then R$^3$ and R$^9$ or R$^2$ and R$^9$ are bonded to each other to form an imidazo[1,2-a]pyridine ring together with the ring formed of dotted lines, any of R$^1$, R$^2$, R$^3$, and R$^8$ that do not bond to constitute a ring may be the same as or different from each other and represent a hydrogen atom, a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, an alkenyl group having 2 to 8 carbon atoms, an alkynyl group having 2 to 8 carbon atoms, an alkylamino group having 1 to 8 carbon atoms, a dialkylamino group having 2 to 12 carbon atoms, an alkyloxycarbonyl group in which the number of carbon atoms of the alkyl group is in a range of 1 to 8, a hydroxy group, an amino group, a carboxyl group, a nitro group, a cyano group, CONR'R", SR', or SO$_2$NR'R", where, R' and R" may be the same as or different from each other and represent a hydrogen atom or an alkyl group having 1 to 8 carbon atoms, when one or more of $R^1$, $R^2$, $R^3$, and $R^8$ bond to constitute a ring, the ring may have 1 to 4 substituents which are the same as the substituent for $R^1$ in the case where $R^1$, $R^2$, $R^3$, and $R^8$ do not bond to constitute a ring, the substituents being the same or different from each other, A represents a phenyl group, a naphthyl group, a pyridyl group, a pyrimidyl group, a pyrazyl group, a pyridazyl group, a quinolyl group, or an isoquinolyl group which may have 1 to 5 substituents same as that of $R^1$ in the case where $R^1$ does not form a ring, the substituents may be the same as or different from each other, where, A is bonded to the ring formed of dotted lines through a carbon atom constituting the ring of the A group, X represents a sulfur atom, Y represents an alkylene chain having 1 to 8 carbon atoms, where, the alkylene chain may be substituted with 1 to 4 same or different groups selected from an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a 3- to 7-membered cycloalkyl group, or a 4- to 7-membered saturated hetero ring having one or two heteroatoms, as a ring constituent element, selected from an oxygen atom, a sulfur atom, and a nitrogen atom, the alkylene chain may be a linear or branched alkylene chain, the branched alkylene chain may have a 3- to 7-membered ring formed by side chains bonded to same carbon atom or different carbon atoms, together with the or each carbon atom to which the side chains are bonded, and the alkylene chain may have a double bond in the chain thereof in a case where the alkylene chain is an alkylene chain having 2 to 8 carbon atoms, Z represents $CO_2H$, $CON(R^{12})(R^{13})$, $CO_2(R^{14})$, $SO_2N(R^{15})(R^{16})$, or a tetrazolyl group, where, $R^{12}$, $R^{14}$, and $R^{15}$ represent a hydrogen atom, an alkyl group having 1 to 8 carbon atoms, an alkyl group having 1 to 8 carbon atoms substituted with 1 to 3 halogen atoms, and $R^{13}$ and $R^{16}$ represent a hydrogen atom, an alkyl group having 1 to 8 carbon atoms, an alkyl group having 1 to 8 carbon atoms substituted with 1 to 3 halogen atoms, a phenyl group which may have a substituent, a pyridyl group which may have a substituent, a pyridazyl group, a pyrimidyl group, or a pyrazyl group, or a 5-membered heteroaryl ring and contains 1 to 3 heteroatoms, as a ring constituent element, selected from a nitrogen atom which may have a substituent, an oxygen atom, and a sulfur atom, and wherein ethyl 3-[[1-(2-fluorophenylnaphthalen-2-yl]thio]propanoate is excluded.

2. The compound, a tautomer or stereoisomer of the compound, or a pharmaceutically acceptable salt or solvate thereof according to claim 1, wherein A represents a phenyl group, a naphthyl group, or a pyridyl group which may have a substituent selected from a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a nitro group, and a cyano group.

3. The compound, a tautomer or stereoisomer of the compound, or a pharmaceutically acceptable salt or solvate thereof according to claim 1, wherein A is represented by the following Formula (II),

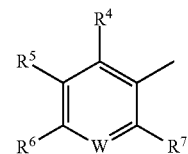

(II)

where, $R^4$ and $R^5$ may form a benzene ring together with two carbon atoms to which $R^4$ and $R^5$ are bonded, or may be the same as or different from each other and represent a hydrogen atom, a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group, where, the benzene ring may have 1 to 4 same or different substituents selected from a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, and a cyano group, $R^6$ and $R^7$ may be the same as or different from each other and represent a hydrogen atom, a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group, W represents $CR^{10}$ or N, where, $R^{10}$ represents any of the groups represented by $R^6$ described above, and "—" represents a bond, in the case where $R^4$ and $R^5$ form a benzene ring, the group A contains a maximum of 5 substituents.

4. The compound, a tautomer or stereoisomer of the compound, or a pharmaceutically acceptable salt or solvate thereof according to claim 3, wherein $R^4$ and $R^5$ may form a benzene ring together with two carbon atoms to which $R^4$ and $R^5$ are bonded, or may be the same as or different from each other and represent a hydrogen atom, a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, or a cyano group, where, the benzene ring may have 1 to 4 same as or different substituents selected from a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, and a cyano group, and $R^6$ and $R^7$ may be the same as or different from each other and represent a hydrogen atom, a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, or a cyano group.

5. The compound, a tautomer or a stereoisomer of the compound, or a pharmaceutically acceptable salt or solvate thereof according to claim 1, wherein Q represents $CR^8$, the ring formed of dotted lines represents a benzene ring, and $R^3$ and $R^8$ are bonded to each other to form a naphthalene ring together with two carbon atoms to which $R^3$ and $R^8$ are bonded.

6. The compound, a tautomer or a stereoisomer of the compound, or a pharmaceutically acceptable salt or solvate thereof according to claim 1, wherein Q represents $CR^8$, the ring formed of dotted lines represents a benzene ring, and $R^3$ and $R^8$ are bonded to each other to form a 5-membered heteroaryl ring containing 1 to 3 heteroatoms, as a ring constituent element, selected from a nitrogen atom, an oxygen atom, and a sulfur atom together with two carbon atoms to which $R^3$ and $R^8$ are bonded.

7. The compound, a tautomer or a stereoisomer of the compound, or a pharmaceutically acceptable salt or solvate thereof according to claim 1, wherein Q represents $CR^8$, the ring formed of dotted lines represents a benzene ring, and $R^3$ and $R^8$ are bonded to each other to form thiazole or isothiazole together with two carbon atoms to which $R^3$ and $R^8$ are bonded.

8. The compound, a tautomer or stereoisomer of the compound, or a pharmaceutically acceptable salt or solvate thereof according to claim 1, wherein, in a case where $R^1$, $R^2$, $R^3$, and $R^8$ do not constitute a ring, $R^1$, $R^2$, $R^3$, and $R^8$ may be the same as or different from each other and represent a hydrogen atom, a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group.

9. The compound, a tautomer or stereoisomer of the compound, or a pharmaceutically acceptable salt or solvate thereof according to claim 1, wherein, in a case where $R^1$, $R^2$, $R^3$, and $R^8$ do not constitute a ring, $R^1$, $R^2$, $R^3$, and $R^8$ may be the same as or different from each other and represent a hydrogen atom, a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, or a cyano group.

10. The compound, a tautomer or stereoisomer of the compound, or a pharmaceutically acceptable salt or solvate thereof according to claim 1, wherein, in a case where $R^1$, $R^2$, $R^3$, and $R^8$ do not constitute a ring, $R^1$, $R^2$, $R^3$, and $R^8$ may be the same as or different from each other and represent a hydrogen atom, a halogen atom, an alkyl group having 1 to 8 carbon atoms, or an alkyl group having 1 to 8 carbon atoms substituted with 1 to 3 halogen atoms.

11. The compound, a tautomer or stereoisomer of the compound, or a pharmaceutically acceptable salt or solvate thereof according to claim 1, wherein the substituent in a case where one or more of $R^1$, $R^2$, $R^3$ and $R^8$ constitute a ring represents 1 to 4 same as or different groups selected from a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group.

12. The compound, a tautomer or stereoisomer of the compound, or a pharmaceutically acceptable salt or solvate thereof according to claim 1, wherein the substituent in a case where one or more of $R^1$, $R^2$, $R^3$ and $R^8$ constitute a ring represents 1 to 4 same as or different groups selected from a halogen atom, an alkyl group having 1 to 8 carbon atoms, a 3- to 7-membered ring cycloalkyl group, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, or a cyano group.

13. The compound, a tautomer or stereoisomer of the compound, or a pharmaceutically acceptable salt or solvate thereof according to claim 1, wherein the substituent in a case where one or more of $R^1$, $R^2$, $R^3$ and $R^8$ constitute a ring represents 1 to 4 same as or different groups selected from a halogen atom, an alkyl group having 1 to 8 carbon atoms, or an alkyl group having 1 to 8 carbon atoms substituted with 1 to 3 halogen atoms.

14. The compound, a tautomer or stereoisomer of the compound, or a pharmaceutically acceptable salt or solvate thereof according to claim 3,
wherein $R^4$ and $R^5$ may be the same as or different from each other and represent a hydrogen atom, a halogen atom, or an alkyl group having 1 to 8 carbon atoms.

15. The compound, a tautomer or stereoisomer of the compound, or a pharmaceutically acceptable salt or solvate thereof according to claim 3,
wherein $R^6$ and $R^7$ may be the same as or different from each other and represent a hydrogen atom, a halogen atom, an alkyl group having 1 to 8 carbon atoms, or a cyano group.

16. The compound, a tautomer or stereoisomer of the compound, or a pharmaceutically acceptable salt or solvate thereof according to claim 3,
wherein $R^6$ represents a cyano group.

17. The compound, a tautomer or stereoisomer of the compound, or a pharmaceutically acceptable salt or solvate thereof according to claim 3,
wherein W represents $CR^{10}$.

18. The compound, a tautomer or stereoisomer of the compound, or a pharmaceutically acceptable salt or solvate thereof according to claim 17,
wherein $R^{10}$ represents a hydrogen atom, a halogen atom, or an alkyl group having 1 to 8 carbon atoms.

19. The compound, a tautomer or stereoisomer of the compound, or a pharmaceutically acceptable salt or solvate thereof according to claim 1,
wherein Y represents an alkylene chain having 1 to 8 carbon atoms, and
where, the alkylene chain may be substituted with 1 to 4 same or different groups selected from an alkyl group having 1 to 8 carbon atoms, an alkoxy group having 1 to 8 carbon atoms, an alkyl group having 1 to 8 carbon atoms substituted with 1 to 3 halogen atoms, or an alkoxy group having 1 to 8 carbon atoms substituted with 1 to 3 halogen atoms.

20. The compound, a tautomer or stereoisomer of the compound, or a pharmaceutically acceptable salt or solvate thereof according to claim 1,
wherein Y represents $C(C_{1-3}\text{ alkyl})_2$.

21. The compound, a tautomer or stereoisomer of the compound, or a pharmaceutically acceptable salt or solvate thereof according to claim 1,
wherein Y represents CH=CH.

22. The compound, a tautomer or stereoisomer of the compound, or a pharmaceutically acceptable salt or solvate thereof according to claim 1,
wherein Y represents $C(C_{1-3}\text{ alkyl})$=CH.

23. The compound, a tautomer or stereoisomer of the compound, or a pharmaceutically acceptable salt or solvate thereof according to claim 1,
wherein Y is represented by the following Formula (V):

$$\overset{R^{01}\ R^{02}}{\underset{|}{\overset{\vee}{\underset{C}{}}}}$$ (V)

in the formula, $R^{01}$ and $R^{02}$ may be the same as or different from each other and represent an alkyl group having 1 to 8 carbon atoms or $R^{01}$ and $R^{02}$ are bonded to each other to form a 3- to 7-membered ring together with carbon atoms to which $R^{01}$ and $R^{02}$ are bonded, and "—" represents a bond.

24. The compound, a tautomer or stereoisomer of the compound, or a pharmaceutically acceptable salt or solvate thereof according to claim 1,
wherein Z represents $CO_2H$, $CON(R^{12})(R^{13})$, $CO_2(R^{14})$, $SO_2N(R^{15})(R^{16})$, or a tetrazolyl group,
where, $R^{12}$, $R^{14}$, and $R^{15}$ represent a hydrogen atom, an alkyl group having 1 to 8 carbon atoms, or an alkyl group having 1 to 8 carbon atoms substituted with 1 to 3 halogen atoms, and
$R^{13}$ and $R^{16}$ represent a hydrogen atom, an alkyl group having 1 to 8 carbon atoms, an alkyl group having 1 to 8 carbon atoms substituted with 1 to 3 halogen atoms, a phenyl group which may have a substituent, or a pyridyl group which may have a substituent.

25. The compound, a tautomer or stereoisomer of the compound, or a pharmaceutically acceptable salt or solvate thereof according to claim 1,
wherein Z represents $CO_2H$.

26. A compound represented by the following Formula (III), a tautomer or stereoisomer of the compound, or a pharmaceutically acceptable salt or solvate thereof:

(III)

in the formula, $R^{1a}$, $R^{2a}$, $R^{6a}$, and $R^{7a}$ a may be the same as or different from each other and represent a hydrogen atom, a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group,
$R^{3a}$ and $R^{8a}$ form a benzene ring or a 5-membered heteroaryl ring containing 1 to 3 heteroatoms, as a ring constituent element, selected from a nitrogen atom, an oxygen atom, and a sulfur atom together with two carbon atoms to which $R^{3a}$ and $R^{8a}$ are bonded,
where, the benzene ring and the heteroaryl ring may have 1 to 4 same or different substituents selected from a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, and a cyano group,
$R^{4a}$ and $R^{5a}$ form a benzene ring together with two carbon atoms to which $R^{4a}$ and $R^{5a}$ are bonded or represent any of the groups represented by $R^{1a}$ described above,
where, the benzene ring may have 1 to 4 same or different substituents selected from a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, and a cyano group, $W^a$ represents $CR^{10a}$ or N, where, $R^{10a}$ represents any of the groups represented by $R^{1a}$, $X^a$ represents a sulfur atom, $Y^a$ represents an alkylene chain having 1 to 8 carbon atoms, where, the alkylene chain may be substituted with 1 to 4 groups selected from an alkyl group having 1 to 8 carbon atoms, an alkoxy group having 1 to 8 carbon atoms, an alkyl group having 1 to 8 carbon atoms substituted with 1 to 3 halogen atoms, or an alkoxy group having 1 to 8 carbon atoms substituted with 1 to 3 halogen atoms, the alkylene chain may be a linear or branched alkylene chain, and the branched alkylene chain may have a 3- to 7-membered ring formed by side chains bonded to same carbon atom or different carbon atoms, together with the or each carbon atom to which the side chains are bonded, and may have a double bond in the chain thereof in a case where the alkylene chain is an alkylene chain having 2 to 8 carbon atoms, $Z^a$ represents $CO_2H$, a tetrazolyl group, or $SO_2NR^{15a}R^{16a}$, and where, $R^{15a}$ and $R^{16a}$ may be the same as or different from each other and represent a hydrogen atom, an alkyl group having 1 to 8 carbon atoms, or an alkyl group having 1 to 8 carbon atoms substituted with 1 to 3 halogen atoms.

27. The compound, a tautomer or stereoisomer of the compound, or a pharmaceutically acceptable salt or solvate thereof according to claim 26, wherein $R^{1a}$, $R^{2a}$, $R^{6a}$, and $R^{7a}$ may be the same as or different from each other and represent a hydrogen atom, a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, or a cyano group, $R^{3a}$ and $R^{8a}$ form a benzene ring or a 5-membered heteroaryl ring containing 1 to 3 heteroatoms, as a ring constituent element, selected from a nitrogen atom, an oxygen atom, and a sulfur atom together with two carbon atoms to which $R^{3a}$ and $R^{8a}$ are bonded, where, the benzene ring and the heteroaryl ring may have 1 to 4 substituents selected from a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, and a cyano group, $R^{4a}$ and $R^{5a}$ from a benzene ring together with two carbon atoms to which $R^{4a}$ and $R^{5a}$ are bonded or represent any of the groups represented by $R^{1a}$ described above, and where, the benzene ring may have 1 to 4 substituents selected from a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, and a cyano group.

28. The compound, a tautomer or stereoisomer of the compound, or a pharmaceutically acceptable salt or solvate thereof according to claim 26, wherein $R^{1a}$, $R^{2a}$, $R^{6a}$, and $R^{7a}$ may be the same as or different from each other and represent a hydrogen atom, an alkyl group having 1 to 8 carbon atoms, an alkoxy group having 1 to 8 carbon atoms, or a cyano group.

29. The compound, a tautomer or stereoisomer of the compound, or a pharmaceutically acceptable salt or solvate thereof according to claim 26, wherein $R^{6a}$ represents a cyano group.

30. The compound, a tautomer or stereoisomer of the compound, or a pharmaceutically acceptable salt or solvate thereof according to claim 26, wherein $R^{3a}$ and $R^{8a}$ form a benzene ring together with two carbon atoms to which $R^{3a}$ and $R^{8a}$ are bonded.

31. The compound, a tautomer or stereoisomer of the compound, or a pharmaceutically acceptable salt or solvate thereof according to claim 26, wherein the benzene ring formed by $R^{3a}$ and $R^{8a}$ together with two carbon atoms to which $R^{3a}$ and $R^{8a}$ are bonded may be substituted with 1 to 4 groups selected from an alkyl group having 1 to 8 carbon atoms, an alkoxy group having 1 to 8 carbon atoms, or a cyano group.

32. The compound, a tautomer or stereoisomer of the compound, or a pharmaceutically acceptable salt or solvate thereof according to claim 26, wherein $R^{3a}$ and $R^{8a}$ form a 5-membered heteroaryl ring containing 2 heteroatoms, as a ring constituent element, selected from a nitrogen atom, an oxygen atom, and a sulfur atom together with two carbon atoms to which $R^{3a}$ and $R^{8a}$ are bonded.

33. The compound, a tautomer or stereoisomer of the compound, or a pharmaceutically acceptable salt or solvate thereof according to claim 26, wherein $R^{3a}$ and $R^{8a}$ form thiazole or isothiazole together with two carbon atoms to which $R^{3a}$ and $R^{8a}$ are bonded.

34. The compound, a tautomer or stereoisomer of the compound, or a pharmaceutically acceptable salt or solvate thereof according to claim 33, wherein the thiazole or isothiazole formed by $R^{3a}$ and $R^{8a}$ together with two carbon atoms to which $R^{3a}$ and $R^{8a}$ are bonded may be substituted with an alkyl group having 1 to 8 carbon atoms, an alkoxy group having 1 to 8 carbon atoms, or a cyano group.

35. The compound, a tautomer or stereoisomer of the compound, or a pharmaceutically acceptable salt or solvate thereof according to claim 26, wherein $R^{4a}$ and $R^{5a}$ may be the same as or different from each other and represent a hydrogen atom, an alkyl group having 1 to 8 carbon atoms, an alkoxy group having 1 to 8 carbon atoms, or a cyano group.

36. The compound, a tautomer or stereoisomer of the compound, or a pharmaceutically acceptable salt or solvate thereof according to claim 26, wherein $W^a$ represents $CR^{10a}$.

37. The compound, a tautomer or stereoisomer of the compound, or a pharmaceutically acceptable salt or solvate thereof according to claim 26, wherein $Y^a$ represents $C(C_{1-3} \text{alkyl})_2$.

38. The compound, a tautomer or stereoisomer of the compound, or a pharmaceutically acceptable salt or solvate thereof according to claim 26, wherein $Y^a$ is represented by the following Formula (VI):

(VI)

in the formula, $R^{a01}$ and $R^{a02}$ may be the same as or different from each other and represent an alkyl group having 1 to 8 carbon atoms or $R^{a01}$ and $R^{a02}$ are bonded to each other to form a 3- to 7-membered ring together with carbon atoms to which $R^{a01}$ and $R^{a02}$ are bonded, and "—" represents a bond.

39. The compound, a tautomer or stereoisomer of the compound, or a pharmaceutically acceptable salt or solvate thereof according to claim 26, wherein $Z^a$ represents $CO_2H$.

40. A compound represented by the following Formula (IV), a tautomer or stereoisomer of the compound, or a pharmaceutically acceptable salt or solvate thereof:

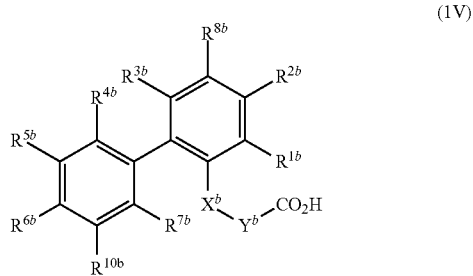

(IV)

in the formula, $R^{1b}, R^{2b}, R^{4b}, R^{5b}, R^{6b}, R^{7b}$, and $R^{10b}$ may be the same as or different from each other and represent a hydrogen atom, a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, or a cyano group, $R^{3b}$ and $R^{8b}$ represent a 5-membered heteroaryl ring containing, as ring constituent elements, two heteroatoms which are one nitrogen atom and one oxygen atom or one nitrogen atom and one sulfur atom, together with two carbon atoms to which $R^{3b}$ and $R^{8b}$ are bonded, where, the heteroaryl ring may have a substituent selected from a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, an alkylsulfanyl group having 1 to 8 carbon atoms, a nitro group, and a cyano group, $X^b$ represents an oxygen atom or a sulfur atom, $Y^b$ represents an alkylene chain having 1 to 8 carbon atoms, and where, the alkylene chain may be substituted with 1 to 4 groups selected from an alkyl group having 1 to 8 carbon atoms, an alkoxy group having 1 to 8 carbon atoms, an alkyl group having 1 to 8 carbon atoms substituted with 1 to 3 halogen atoms, or an alkoxy group having 1 to 8 carbon atoms substituted with 1 to 3 halogen atoms, the alkylene chain may be a linear or branched alkylene chain, and the branched alkylene chain may have a 3- to 7-membered ring formed by side chains bonded to same carbon atom or different carbon atoms, together with the or each carbon atom to which the side chains are bonded and may have a double bond in the chain thereof in a case where the alkylene chain is an alkylene chain having 2 to 8 carbon atoms.

41. The compound, a tautomer or stereoisomer of the compound, or a pharmaceutically acceptable salt or solvate thereof according to claim 40, wherein $R^{1b}, R^{2b}, R^{4b}, R^{5b}, R^{6b}, R^{7b}$, and $R^{10b}$ may be the same as or different from each other and represent a hydrogen atom, a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, or a cyano group, $R^{3b}$ and $R^{8b}$ represent a 5-membered heteroaryl ring containing, as a ring constituent element, two heteroatoms which are one nitrogen atom and one oxygen atom or one nitrogen atom and one sulfur atom, together with two carbon atoms to which $R^{3b}$ and $R^{8b}$ are bonded, and where, the heteroaryl ring may have a substituent selected from a halogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a hydroxy group, an amino group, a carboxyl group, a mercapto group, a nitro group, and a cyano group.

42. The compound, a tautomer or stereoisomer of the compound, or a pharmaceutically acceptable salt or solvate thereof according to claim 40, wherein $R^{1b}, R^{2b}, R^{4b}, R^{5b}, R^{6b}, R^{7b}$, and $R^{10b}$ may be the same as or different from each other and represent a hydrogen atom, an alkyl group having 1 to 8 carbon atoms, an alkoxy group having 1 to 8 carbon atoms, or a cyano group.

43. The compound, a tautomer or stereoisomer of the compound, or a pharmaceutically acceptable salt or solvate thereof according to claim 40, wherein $R^{6b}$ represents a cyano group.

44. The compound, a tautomer or stereoisomer of the compound, or a pharmaceutically acceptable salt or solvate thereof according to claim 40, wherein $R^{3b}$ and $R^{8b}$ form thiazole or isothiazole together with two carbon atoms to which $R^{3b}$ and $R^{8b}$ are bonded.

45. The compound, a tautomer or stereoisomer of the compound, or a pharmaceutically acceptable salt or solvate thereof according to claim 44, wherein the thiazole or isothiazole formed by $R^{3b}$ and $R^{8b}$ together with two carbon atoms to which $R^{3b}$ and $R^{8b}$ are bonded may be substituted with a substituent selected from an alkyl group having 1 to 8 carbon atoms, an alkoxy group having 1 to 8 carbon atoms, and a cyano group.

46. The compound, a tautomer or stereoisomer of the compound, or a pharmaceutically acceptable salt or solvate thereof according to claim 40,
wherein $X^b$ represents a sulfur atom.

47. The compound, a tautomer or stereoisomer of the compound, or a pharmaceutically acceptable salt or solvate thereof according to claim 40,
wherein $Y^b$ represents $C(C_{1-3}$ alkyl$)_2$.

48. The compound, a tautomer or stereoisomer of the compound, or a pharmaceutically acceptable salt or solvate thereof according to claim 40,
wherein $Y^b$ is represented by the following Formula (VII):

(VII)

in the formula, $R^{b01}$ and $R^{b02}$ may be the same as or different from each other and represent an alkyl group having 1 to 8 carbon atoms or $R^{b01}$ and $R^{b02}$ are bonded to each other to form a 3- to 7-membered ring together with carbon atoms to which $R^{b01}$ and $R^{b02}$ are bonded.

49. A compound selected from the following compounds, a tautomer or stereoisomer of the compound, or a pharmaceutically acceptable salt or solvate thereof:
ethyl 2-[[4'-cyano-(1,1'-binaphthalene)-2-yl]oxy]-2-methyl propanoate,
2-[[4'-cyano-(1,1'-binaphthalene)-2-yl]oxy]-2-methyl propanoic acid,
ethyl 2-[[4'-cyano-(1,1'-binaphthalene)-2-yl]thio]-2-methyl propanoate,
2-[[4'-cyano-(1,1'-binaphthalene)-2-yl]thio]-2-methyl propanoic acid,
t-butyl (E)-3-[[1-(4-cyanophenyl)naphthalen-2-yl]oxy]acrylate,
(E)-3-[[1-(4-cyanophenyl)naphthalen-2-yl]oxy]acrylic acid,
(Z)-3-[[1-(4-cyanophenyl)naphthalen-2-yl]oxy]acrylic acid,
2-methyl-2-[[1-(pyridin-3-yl)naphthalen-2-yl]oxy]propanoic acid,
methyl (E)-3-[[1-(pyridin-3-yl)naphthalen-2-yl]oxy]acrylate,
(E)-3-[[1-(pyridin-3-yl)naphthalen-2-yl]oxy]acrylic acid,
(Z)-3-[[1-(pyridin-3-yl)naphthalen-2-yl]oxy]acrylic acid,
ethyl 2-[[5-(4-cyanophenyl)quinolin-6-yl]oxy]-2-methyl propanoate,
2-[[5-(4-cyanophenyl)quinolin-6-yl]oxy]-2-methyl propanoic acid,
ethyl 2-[[5-(4-cyanophenyl)quinolin-6-yl]thio]-2-methyl propanoate,
2-[[5-(4-cyanophenyl)quinolin-6-yl]thio]-2-methyl propanoic acid,
ethyl 2-[[7-(4-cyanophenyl)benzo[d]oxazol-6-yl)oxy]-2-methyl propanoate,
2-[[7-(4-cyanophenyl)benzo[d]oxazol-6-yl]oxy]-2-methyl propanoic acid,
ethyl 2-[[7-(4-cyanophenyl)benzo[d]thiazol-6-yl]oxy]-2-methyl propanoate,
2-[[7-(4-cyanophenyl)benzo[d]thiazol-6-yl]oxy]-2-methyl propanoic acid,
t-butyl (E)-3[7-(4-cyanophenyl)benzo[d]thiazol-6-yl]oxy]acrylate,
(E)-3-[[7-(4-cyanophenyl)benzo[d]thiazol-6-yl]oxy]acrylic acid,
ethyl 2-[[7-(4-cyanophenyl)benzo[d]thiazol-6-yl]thio]-2-methyl propanoate,
t-butyl 2-4[7-(4-cyanophenyl)benzo[d]thiazol-6-yl]thio]-2-methyl propanoate,
2[7-(4-cyanophenyl)benzo[d]thiazol-6-yl]thio]-2-methyl propanoic acid,
ethyl 2-[[7-(4-cyanophenyl)benzo[d]isothiazol-6-yl]oxy]-2-methyl propanoate,
2-[[7-(4-cyanophenyl)benzo[d]isothiazol-6-yl]oxy]-2-methyl propanoic acid,
ethyl 2-[[7-(4-cyanophenyl)benzo[d]isothiazol-6-yl]thio]-2-methyl propanoate,
2[7-(4-cyanophenyl)benzo[d]isothiazol-6-yl]thio]-2-methyl propanoic acid,
ethyl 2-[[4-(4-cyanophenyl)benzo[c][1,2,5]thiadiazol-5-yl]oxy]-2-methyl propanoate,
2-[[4-(4-cyanophenyl)benzo[c][1,2,5]thiadiazol-5-yl]oxy]-2-methyl propanoic acid,
ethyl 2-[[4-(4-cyanophenyl)benzo[c][1,2,5]thiadiazol-5-yl]thio]-2-methyl propanoate,
2-[[4-(4-cyanophenyl)benzo[c][1,2,5]thiadiazol-5-yl]thio]-2-methyl propanoic acid,
2-[[4-(4-cyanophenyl)-1H-indol-5-yl]oxy]-2-methyl propanoic acid,
ethyl 2-[[6-(4-cyanophenyl)benzo[d]thiazol-5-yl]oxy]-2-methyl propanoate,
2-[[6-(4-cyanophenyl)benzo[d]thiazol-5-yl]oxy]-2-methyl propanoic acid,
ethyl 2-[[6-(4-cyanophenyl)benzo[d]thiazol-7-yl]oxy]-2-methyl propanoate,
2-[[6-(4-cyanophenyl)benzo[d]thiazol-7-yl]oxy]-2-methyl propanoic acid,
ethyl 2-[[6-(4-cyanophenyl)benzo[d]thiazol-7-yl]thio]-2-methyl propanoate,
2-[[6-(4-cyanophenyl)benzo[d]thiazol-7-yl]thio]-2-methyl propanoic acid,
ethyl 2-[[8-(4-cyanophenyl)imidazo[1,2-a]pyridin-7-yl]thio]-2-methyl propanoate,
2-[[8-(4-cyanophenyl)imidazo[1,2-a]pyridin-7-yl]thio]-2-methyl propanoic acid,
ethyl 2-[[6-(4-cyanophenyl)imidazo[1,2-a]pyridin-7-yl]oxy]-2-methyl propanoate,
2-[[6-(4-cyanophenyl)imidazo[1,2-a]pyridin-7-yl]oxy]-2-methyl propanoic acid,
ethyl 2-[[3-(4-cyanophenyl)quinolin-4-yl]thio]-2-methyl propanoate,
2-[[3-(4-cyanophenyl)quinolin-4-yl]thio]-2-methyl propanoic acid,
ethyl (E)-3-[[1-(4-cyanophenyl)naphthalen-2-yl]oxy]-2-butenoate,
(E)-3-[[1-(4-cyanophenyl)naphthalen-2-yl]oxy]-2-butenoic acid,
t-butyl 2-[[1-(4-cyanophenyl)naphthalen-2-yl]thio]-2-methyl propanoate,
2-[[1-(4-cyanophenyl)naphthalen-2-yl]thio]-2-methyl propanoic acid,
t-butyl (E)-3-[[1-(4-cyanophenyl)naphthalen-2-yl]thio]acrylate,
(E)-3-[[1-(4-cyanophenyl)naphthalen-2-yl]thio]acrylic acid, 2-[[7-(4-cyanophenyl)benzo[d]thiazol-6-yl]thio]-2-methyl propanamide,
2-[[7-(4-cyanophenyl)benzo[d]thiazol-6-yl]thio]-N-(5-fluoropyridin-2-yl)-2-methyl propanamide,
2-[[7-(4-cyanophenyl)benzo[d]thiazol-6-yl]thio]-2-methyl-N-(1,3,4-thiadiazol-2-yl)propanamide,
t-butyl 2-[[4-(4-cyanophenyl)benzo[d]thiazol-5-yl]oxy]-2-methyl propanoate, and
2-[[4-(4-cyanophenyl)benzo[d]thiazol-5-yl]oxy]-2-methyl propanoic acid.

50. A compound selected from the following compounds, a tautomer or stereoisomer of the compound, or a pharmaceutically acceptable salt or solvate thereof:
    ethyl (E)-3-[[1-(4-cyanophenyl)naphthalen-2-yl]oxy]-2-pentenoate,
    (E)-3-[[1-(4-cyanophenyl)naphthalen-2-yl]oxy]-2-pentenoic acid,
    t-butyl 2-[[7-(4-cyanophenyl)-2-(trifluoromethyl)benzo[d]thiazol-6-yl]thio]-2-methyl propanoate,
    2-[[7-(4-cyanophenyl)-2-(trifluoromethyl)benzo[d]thiazol-6-yl]thio]-2-methyl propanoic acid,
    ethyl 2-[[7-(4-cyanophenyl)-2-methyl benzo[d]thiazol-6-yl]thio]-2-methyl propanoate,
    2-[[7-(4-cyanophenyl)-2-methyl benzo[d]thiazol-6-yl]thio]-2-methyl propanoic acid,
    t-butyl 2-methyl-2-[[7-[4-(trifluoromethoxy)phenyl]benzo[d]thiazol-6-yl]thio]propanoate,
    2-methyl-2-[[7-[4-(trifluoromethoxy)phenyl]benzo[d]thiazol-6-yl]thio]propanoic acid,
    ethyl 1-[[7-(4-cyanophenyl)benzo[d]isothiazol-6-yl]thio]cyclobutan-1-carboxylate,
    1-[[7-(4-cyanophenyl)benzo[d]isothiazol-6-yl]thio]cyclobutan-1-carboxylic acid,
    methyl 1-[[7-(4-cyanophenyl)benzo[d]isothiazol-6-yl]thio]cyclopentan-1-carboxylate,
    1-[[7-(4-cyanophenyl)benzo[d]isothiazol-6-yl]thio]cyclopentan-1-carboxylic acid,
    methyl 2-[[7-(4-cyanophenyl)benzo[d]isothiazol-6-yl]thio]-3-methyl butanoate,
    2-[[7-(4-cyanophenyl)benzo[d]isothiazol-6-yl]thio]-3-methyl butanoic acid,
    ethyl 2-methyl-2-[[7-(4-nitrophenyl)benzo[d]isothiazol-6-yl]thio]propanoate,
    2-methyl-2[[7-(4-nitrophenyl)benzo[d]isothiazol-6-yl]thio]propanoic acid,
    t-butyl 2-methyl-2-[[7-(p-tolyl)benzo[d]isothiazol-6-yl]thio]propanoate,
    2-methyl-2-[[7-(p-tolyl)benzo[d]isothiazol-6-yl]thio]propanoic acid,
    t-butyl 2-[[7-(4-isopropylphenyl)benzo[d]isothiazol-6-yl]thio]-2-methyl propanoate,
    2-[[7-(4-isopropylphenyl)benzo[d]isothiazol-6-yl]thio]-2-methyl propanoic acid,
    t-butyl 2-methyl-2-[[7[4-(trifluoromethyl)phenyl]benzo[d]isothiazol-6-yl]ithio]propanoate,
    2-methyl-2-[[7-4-(trifluoromethyl)phenylTenzo[d]isothiazol-6-yl]thio]propanoic acid,
    t-butyl 2-methyl-2-[[7-[4-(trifluoromethoxy)phenyl]benzo[d]isothiazol-6-yl]ithio]propanoate,
    2-methyl-2-[[7-[4-(trifluoromethoxy)phenyl]benzo[d]isothiazol-6-yl]thio]propanoic acid,
    t-butyl 2-[[7-(4-chlorophenyl)benzo[d]isothiazol-6-yl]thio]-2-methyl propanoate,
    2-[[7-(4-chlorophenyl)benzo[d]isothiazol-6-yl]thio]-2-methyl propanoic acid,
    t-butyl 2-[[7-(3-cyanophenyl)benzo[d]isothiazol-6-yl]thio]-2-methyl propanoate,
    2-[[7-(3-cyanophenyl)benzo[d]isothiazol-6-yl]thio]-2-methyl propanoic acid,
    ethyl 2-[[7-(4-cyano-2-methylphenyl)benzo[d]isothiazol-6-yl]thio]-2-methyl propanoate,
    2-[[7-(4-cyano-2-methylphenyl)benzo[d]isothiazol-6-yl]thio]-2-methyl propanoic acid,
    t-butyl 2-[[7-(4-cyano-3-methylphenyl)benzo[d]isothiazol-6-yl]thio]-2-methyl propanoate,
    2[[7-(4-cyano-3-methylphenyl)benzo[d]isothiazol-6-yl]thio]-2-methyl propanoic acid,
    t-butyl 2-[[7-(4-cyano-3-fluorophenyl)benzo[d]isothiazol-6-yl]thio]-2-methyl propanoate,
    2-[[7-(4-cyano-3-fluorophenyl)benzo[d]isothiazol-6-yl]thio]-2-methyl propanoic acid,
    t-butyl 2-[[7-(4-fluoronaphthalen-1-yl)benzo[d]isothiazol-6-yl]thio]-2-methyl propanoate,
    2[[7-(4-fluoronaphthalen-1-yl)benzo[d]isothiazol-6-yl]thio]-2-methyl propanoic acid,
    t-butyl 2-[[7-(4-cyanonaphthalen-1-yl)benzo[d]isothiazol-6-yl]thio]-2-methyl propanoate,
    2-[[7-(4-cyanonaphthalen-1-yl)benzo[d]isothiazol-6-yl]thio]-2-methyl propanoic acid,
    t-butyl 2-methyl-2-[[7-(pyridin-3-yl)benzo[d]isothiazol-6-yl]thio]propanoate,
    2-methyl-2-[[7-(pyridin-3-yl)benzo[d]isothiazol-6-yl]thio]propanoic acid,
    ethyl 2-methyl-2[[7-(pyridin-4-yl)benzo[d]isothiazol-6-yl]thio]propanoate,
    2-methyl-2-[[7-(pyridin-4-yl)benzo[d]isothiazol-6-yl]thio]propanoic acid,
    ethyl 2-methyl-2[[7-[6-(methylthio)pyridin-3-yl]benzo[d]isothiazol-6-yl]thio]propanoate,
    2-methyl-2-[[7-[6-(methylthio)pyridin-3-yl]benzo[d]isothiazol-6-yl]thio]propanoic acid,
    t-butyl 2-[[7-(4-cyanophenyl)-4-fluorobenzo[d]isothiazol-6-yl]thio]-2-methyl propanoate,
    2-[[7-(4-cyanophenyl)-4-fluorobenzo[d]isothiazol-6-yl]thio]-2-methyl propanoic acid,
    t-butyl 2-[[7-(4-cyanophenyl)-5-fluorobenzo[d]isothiazol-6-yl]thio]-2-methyl propanoate,
    2-[[7-(4-cyanophenyl)-5-fluorobenzo[d]isothiazol-6-yl]thio]-2-methyl propanoic acid,
    ethyl 2-[[7-(4-cyanophenyl)-3-methylbenzo[d]isothiazol-6-yl]oxy]-2-methyl propanoate,
    2-[[7-(4-cyanophenyl)-3-methylbenzo[d]isothiazol-6-yl]oxy]-2-methyl propanoic acid,
    ethyl 2-[[7-(4-cyanophenyl)-3-methylbenzo[d]isothiazol-6-yl]thio]-2-methyl propanoate,
    2-[[7-(4-cyanophenyl)-3-methylbenzo[d]isothiazol-6-yl]thio]-2-methyl propanoic acid,
    t-butyl 5-[6-[[1-(t-butoxy)-2-methyl-1-oxopropan-2-yl]thio]-3-methylbenzo[d]isothiazol-7-yl]picolinate, and
    2-[[7-[6-(ethoxycarbonyl)pyridin-3-yl]-3-methylbenzo[d]isothiazol-6-yl]thio]-2-methyl propanoic acid.

51. A compound selected from the following compounds, a tautomer or stereoisomer of the compound, or a pharmaceutically acceptable salt or solvate thereof:
    ethyl 5-[6-[[1-(t-butoxy)-2-methyl-1-oxopropan-2-yl]thio]-3-methylbenzo[d]isothiazol-7-yl]picolinate,
    ethyl 1-[[7-(4-cyanophenyl)-3-methylbenzo[d]isothiazol-6-yl]thio]cyclobutan-1-carboxylate,
    1-[[7-(4-cyanophenyl)-3-methylbenzo[d]isothiazol-6-yl]thio]cyclobutan-1-carboxylic acid,
    2-[[7-(4-cyanophenyl)benzo[d]isothiazol-6-yl ]thio]-2-ethyl butanoic acid,
    2-[[7-(4-cyanophenyl)benzo[d]isothiazol-6-yl]thio]-3,3-dimethyl butanoic acid, t-butyl (E)-3-[[1-(4-cyanophenyl)naphthalen-2-yl]thio]-2-butenoate, (E)-3-[[1-(4-cyanophenyl)naphthalen-2-yl]thio]-2-butenoic acid, and 1-[[7-(4-cyanophenyl)benzo[d]isothiazol-6-yl]thio]cyclohexan-1-carboxylic acid.

52. A pharmaceutical composition comprising the compound, a tautomer or stereoisomer of the compound, or a pharmaceutically acceptable salt or solvate thereof according to claim 1 as an active component.

53. A URAT1 inhibitor comprising the compound, a tautomer or stereoisomer of the compound, or a pharmaceutically acceptable salt or solvate thereof according to claim 1 as an active component.

54. A therapeutic agent for gout or hyperuricemia comprising the compound, a tautomer or stereoisomer of the compound, or a pharmaceutically acceptable salt or solvate thereof according to claim 1 as an active component.

55. A method of treating gout or hyperuricemia in human comprising:

a process of administering an effective amount of the compound, a tautomer or stereoisomer of the compound, or a pharmaceutically acceptable salt or solvate thereof according to claim 1 to said human.

56. A method of screening a substance having a URAT1 inhibitory action, the method comprising:

culturing URAT1 stably expressed HEK293 cells or HEK293 cells transfected with empty vector, at 37±1° C., subsequently adding an uptake solution pH7.4±0.1 at 37±1° C., the uptake solution containing [$^{14}$C] uric acid with the compound, a tautomer or stereoisomer of the compound, or a pharmaceutically acceptable salt or solvate thereof according to claim 1, further incubating the cells at 37±1° C. for 2 to 10 minutes, stopping the reaction, washing the cells, lysing the cells, and measuring the radioactivity.

* * * * *